(12) United States Patent
Ranum et al.

(10) Patent No.: US 7,527,931 B2
(45) Date of Patent: May 5, 2009

(54) IDENTIFICATION OF A GENE ASSOCIATED WITH SPINOCEREBELLAR ATAXIA TYPE 5 AND METHODS OF USE

(75) Inventors: Laura P. W. Ranum, St. Paul, MN (US); Yoshio Ikeda, St. Paul, MN (US); Katherine A. Dick, Minneapolis, MN (US); John W. Day, Minneapolis, MN (US); Lawrence J. Schut, Maple Lake, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 11/359,951

(22) Filed: Feb. 22, 2006

(65) Prior Publication Data
US 2006/0286568 A1 Dec. 21, 2006

Related U.S. Application Data

(60) Provisional application No. 60/655,172, filed on Feb. 22, 2005.

(51) Int. Cl.
*C07H 21/04* (2006.01)
*C12Q 1/68* (2006.01)

(52) U.S. Cl. .................... 435/6; 435/91.1; 435/91.2; 536/23.1; 536/24.3

(58) Field of Classification Search .................. None
See application file for complete search history.

(56) References Cited

U.S. PATENT DOCUMENTS

| | | | |
|---|---|---|---|
| 4,988,617 A | 1/1991 | Landegren et al. | |
| 5,190,856 A | 3/1993 | Borresen | |
| 5,324,631 A | 6/1994 | Helentjaris et al. | |
| 5,496,699 A | 3/1996 | Sorenson | |
| 5,633,365 A | 5/1997 | Stokke et al. | |
| 5,639,611 A | 6/1997 | Wallace et al. | |
| 5,665,549 A | 9/1997 | Pinkel et al. | |
| 2003/0092019 A1* | 5/2003 | Meyer et al. ............... | 435/6 |

OTHER PUBLICATIONS

Ranum et al. (Genetics of Movement Disorders, Chapter 7, pp. 75-80, 2003).*
Chen et al. (J. of Molecular Neuroscience, vol. 17, 2001, pp. 59-70).*
Stankewich et al. (PNAS, vol. 95, pp. 14158-14163, Nov. 1998).*
Ioannidis (Nature Genetics, vol. 29, pp. 306-309, Nov. 2001).*
Hirschhorn et al. (Genetics in Medicine. vol. 4, No. 2, pp. 45-61, Mar. 2002).*
Ikeda et al. (Nature Genetics, vol. 38, No. 2, pp. 184-190, Feb. 2006).*
Zuhlke et al (J. Neurol, vol. 254, pp. 1649-1652, 2007).*
Lorenzo et al., "Spinocerebellar ataxia type 20 is genetically distinct from spincocerebellar ataxia type5," *Neurology*, Dec. 12, 2006;67(11):2084-2085.
Adams et al., "The Southeast Collaboratory for Structural Genomics: A High-Throughput Gene to Structure Factory," 2003. *Acc. Chem. Res.* 36:191-198.
Apfeld et al., "Cell Nonautonomy of *C. elegans daf*-2 Function in the Regulation of Diapause and Life Span," 1998. *Cell*, 95:199-210.
Bass. "The Short Answer," 2001. *Nature*. 411:428-429.
Bernard et al., "The F Plasmid CcdB Protein Induces Efficient ATP-dependent DNA Cleavage by Gyrase," 1993. *J. Mol. Biol.* 234:534-541.
Bernard et al., "The 41 carboxy-terminal resides of the miniF plasmid CcdA protein are sufficient to antagonize the killer activity of the CcdB protein," 1991. *Mol. Gen Genet.* 226:297-304.
Brenner. "Target selection for structural genomics," 2000. *Nature Structural Biology. Structural Genomics Supplement*. p. 967-969.
Brenner et al., "Expectations from structural genomics," 2000. *Protein Science.* 9:197-200.
Burk et al., "Spinocerebellar ataxia type 5," 2004. *Neurology*, 62:327-329.
Burley. "An Overview of Structural Genomics," Nov. 2000. Nature Structural Biology. Structural Genomics Supplement. pp. 932-934.
Chance et al., "Structural Genomics: A Pipeline for Providing Structures for the Biologist," 2002. *Protein Science.* 11:723-738.
Chayen. "Protein crystallization for genomics: throughput versus output," 2003. *Journ. Of Structural and Functional Genomics.* 4:115-120.
Cherry et al., "Genetic and Physical Maps of *Saccharomyces cerevisiae*," 1997. *Nature.* 387:67-73.
Christendat et al., "Structural Proteomics of an Archaeon," 2000. *Nature Structural Biology.* vol. 7, No. 10, pp. 903-909.
Cormack et al., "FACS-optimized mutants of the green fluorescent protein (GFP)," 1996. *Gene*, 173:33-38.
de Graaff et al., "Hotspot for deletions in the CGG repeat region of FMR1 in fragile X patients," 1995. *Hum. Mol. Genet* 4:45-49.
Dolinski et al., "Changing perspectives in yeast research nearly a decade after the genome sequence," 2005. *Genome Res.* 15:1611-1619.
Elshorst et al., "NMR Solution Structure of a Complex of Calmodulin with a Binding Peptide of the $Ca^{2+}$Pump," 1999. *Biochemistry*, 38:12320-12332.
Falconer et al., "Chemical Treatment of *Escherichia coli*: 1. Extraction of Intracellular Protein from Uninduced Cells," 1997. *Biotechnology and Bioengineering*, 63:5:454-458.

(Continued)

Primary Examiner—Jeanine A Goldberg
(74) Attorney, Agent, or Firm—Mueting Raasch & Gebhardt, P.A.

(57) ABSTRACT

The present invention provides methods that include analyzing an SCA5 polynucleotide, and determining whether the SCA5 polynucleotide includes a mutation. The methods may be used to identify a subject that is at risk or not at risk for developing spinocerebellar ataxia type 5. The present invention also provides isolated polynucleotides having a mutation present in an SCA5 polynucleotide.

9 Claims, 33 Drawing Sheets

OTHER PUBLICATIONS

Fire et al., "Potent and specific genetic interference by double-stranded RNA in *Caenorhabditis elegans*," 1998. *Nature.* 39:806-811.

Gauthier et al., "Huntingtin Controls Neurotrophic Support and Survival of Neurons by Enhancing BDNF Vesicular Transport along Microtubules," 2004. *Cell.* 118:127-138.

GenBank Accession No. NM_006946.6 6 pages, Aug. 20, 2006.

GenBank Accession No. AB008567.9 pages, Sep. 9, 1998.

Gold et al., "RoRα Coordinates Reciprocal Signaling in Cerebellar Development through *Sonic hedgehog* and Calcium-Dependent Pathways," 2003. *Neuron* 40:1119-1131.

Gonczy et al., "Functional genomic analysis of cell division in *C. elegans* using RNAi of genes on chromosome III," *Nature.* 408:331-336. 2000.

Gordon et al., "Consed: A Graphical Tool for Sequence Finishing," 1998. *Genome Res.* 8:195-202.

Hafezparast et al., "Mutations in Dynein Link Motor Neuron Degeneration to Defects in Retrograde Transport," 2003. *Science.* 300:808-812.

Harding. "Clinical Features and Classification of Inherited Ataxias," 1993. *Adv. Neurol* 61:1-14.

Holleran et al., "βIII Spectrin Binds to the Arp 1 Subunit of Dynactin," 2001. *J. Biol. Chem.*, 276:36598-36605.

Huang et al., "Climbing Fiber Activation of EAAT4 Transporters and Kainate Receptors in Cerebellar Purkinje Cells," 2004. *Journ. Of Neurosci* 24:103-111.

Huynh et al., "Expansion of the polyQ repeat in ataxin-2 alters its Golgi localization, disrupts the Golgi complex and causes cell death," 2003. *Hum. Mol. Genet.* 12:1485-1496.

Jackson et al., "Modulation of the neuronal glutamatge transporter EAAT4 by two interacting proteins," 2001. *Nature.* 410:89-83.

Kamath et al., "Genome-wide RNAi screening in *Caenorhabditis elegans*," 2003. *Methods.* pp. 313-321.

Kessler et al., "Study of Calmodulin Binding to the Alterntively Spliced C-Terminal Domain of the Plasma Membrane $CA^{2+}$ Pump," 1992. *Biochemistry.* 31:11785-11792.

Knight et al., "Dominatly inherited ataxia and dysphonia with dentate calcification: spinocerebellar ataxia type 20," 2004. *Brain*, 127:1172-1181.

Krawczak et al., "Gene deletions causing human genetic disease: mechanisms of mutagenesis and the role of the local DNA sequence environment," 1991. *Hum. Genet.* 86:425-441.

Lalouette et al., "Hotfoot Mouse Mutations Affect the δ2 Glutamate Receptor Gene and Are Allelic to Lurcher," 1998. *Genomics.* 50:9-13.

Landy. "Dynamic, Structural, and Regulatory Aspects of λ Site-Specific Recombination," 1989. *Annu. Rev. Biochem.* 58:913-949.

Lee et al., 2001. "Biochemical and morphological characterization of an intracellular membrane compartment containing AMPA receptors," *Neuropharmacology*, 41:680-692.

Lin et al., "Polyglutamine expansion down-regulates specific neuronal genes before pathologic changes in SCA1," 2000. *Nat. Neurosci.* 3:157-163.

Liquori et al., "Myotonic Dystrophy Type 2 Caused by a CCTG Expansion in Intron 1 of *ZNF9*," 2001. *Science* 293:864-867.

Liquori et al., "Spinocerebellar Ataxia Type 5," in The Cerebellum and its Disorders (eds. Manto, M.U.& Pandolfo, M.) 445-450 (Cambridge Univ. Press, Cambridge). 2002.

Liu et al., "The High-throughput protein-to-structure pipeline at SECSG," 2005. *Acta Cryst.* D61:679-684.

Lopez-Correa et al., "Recombination hotspot in JF1 microdeletion patients," 2001. *Hum. Mol. Genet* 10:1387-1392.

Maragakis et al. 1997. Paper presented at the 27th Ann. Mt. of the Soc. for Neuroscience, New Orleans, LA. Oct. 25-30, 1997.

Maragakis et al., "Glutamate transporters: animal models to neurologic disease," 2004. *Neurobiol. Dis.* 15:461-473.

Matz et al., "Fluorescent proteins from nonbioluminescent Anthozoa species," 1999. *Nature Biotechnology.* 17:969-973.

McKusick., "The defect in Marfan syndrome," 1991. *Nature* 352:279-281.

Nagai et al., "A variant of yellow fluorescent protein with fast and efficient maturation for cell-biological applications," 2002. *Nature Biotechnology.* 20:87-90.

Norvell et al., "Structural genomics programs at the US National Institute of General Medical Sciences," 2000. *Nature Structural Biology. Structural Genomics Supplement.* p. 931.

Novina et al., "The RNAi revolution," 2004. *Nature.* 430:161-164.

O'Hara et al., "Characterization of a new β-spectrin gene which is predominantly expressed in brain," 1998. *Brain Res. Mol. Brain Res.*, 57:181-192.

Papadopoulos et al. "Monoallelic mutation analysis (MAMA) for identifying germline mutations," 1995. *Nat. Genet.* 11:99-102.

Park et al., "Mutations with Dominant Effects on the Behavior and Morphology of the Nematode *Caenorhabditis elegans*," 1986. *Genetics*, 113:821-852.

Parkinson et al., "Mutant β-spectrin 4 causes auditory and motor neuropathies in quivering mice," 2001. *Nat. Genet.* 29:61-65.

Puls et al., "Mutant dynactin in motor neuron disease," 2003. *Nat. Genet.* 33:455-456.

Raiteri et al., "Coexistence and function of different neurotransmitter transporters in the plasma membrane of CNS neurons," 2002. *Prog. Neurobiol.* 68:287-309.

Ranum et al., "Spinocerebellar ataxia type 5 in a family descended from the grandparents of President Lincoln maps to chomosone 11," 1994. *Nature Genetics*, 8:280-284.

Ranum et al., "Pathogenic RNA repeats: an expanding role in genetic disease," 2004. *Trends Genet.* 20:506-512.

Rost. "Marrying structure and genomics," 1998. *Structure.* 6:259-263.

Rual et al., "ORFeome projects: gateway between genomics and omics," 2004. *Current Opinion in Chemical Biology.* 80:20-25.

Salmon et al., "The antidote and autoregulatory functions of the F plasmid CcdA protein: a genetic and biochemical survey," 1994. *Mol. Gen. Genet.* 244:530-538.

Sambrook et al., *Molecular Cloning: A Laboratory Manual*, Cold Spring Harbor Laboratory Press, Cold Spring Harbor, NY, 1989. Copyright Page and Table of Contents.

Sasaki et al., "Evidence for high specificity and efficiency of multiple recombination signals in mixed DNA cloning by the Multisite Gateway system," 2004. *Journ. Of Biotechnology.* 107:233-243.

Sasaki et al., "Multi-gene gateway clone design for expression of multiple heterologous genes in living cells: Eukaryotic clones containing two and three ORF multi-gene cassettes expressed from a single promotor," 2005. *Journ. Of Biotechnology.* 14 pages.

Schols et al., "Autosomal dominant cerebellar ataxias: clinical features, genetics, and pathogenesis," 2004. *Lancet Neurol.*, 3:291-304.

Serra et al., "Gene profiling links SCA1 pathophysiology to glutamate signaling in Purkinje cells of transgenic mice," 2004. *Hum. Mol. Genet.* 13:2535-2543.

Sharp et al., "RNA interference—2001," *Genes & Development*, 15:485-490.

Silva et al., "RNA-interference-based functional genomics in mammalian cells: reverse genetics coming of age," 2004. *Oncogene*, 23:8401-8409.

Sørensen et al., "Advanced genetic stragegies for recombinant protein expression in *Escherichia coli*," 2005. *Journ. Of Biotechnology.* 115:113-128.

Stabach et al., "Identification and Characterization of βV Spectrin, a Mammalian Ortholog of *Drosophila* $β_H$ Spectrin," 2000. *J. Biol. Chem.* 275:21385.

Stankewich et al., "A Widely expressed βIII spectrin associated with Golgi and cytoplasmic vesicles," 1998. *Proc. Nat. Acad. Sci. USA*, 95:14158-14163.

Stevanin et al., "Clinical and MRI findings in spinocerebellar ataxia type 5," 1999. *Neurology*, 53:1355-1357.

Stevanin et al., Spinocerebelar Ataxia with Sensor Neuropathy (SCA25) Maps to Chromosome 2p, 2004. *Ann.Neurol*, 55:97-104.

Stokin et al. "Axonopathy and Transport Deficits Early in the Pathogenesis of Alzheimer's Disease," 2005. *Science*, 307:1282-1288.

Timmons et al., "Specific interference by ingested dsRNA," 1998. *Nature*, 395:854.

vanHaaften et al., "Genomic instability and cancer: scanning the *Caenorhabditis elegans* genome for tumor suppressors," 2004. *Oncogene.* 23:8366-8375.

Walhout et al., "Gateway Recombinational Cloning: Application to the Cloning of Large Numbers of Open Reading Frames or ORFeomes," 2000. *Methods in Enzymology*, 328:575-593.

Wianny et al., "Specific interference with gene function by double-stranded RNA in early mouse development," 2000. *Nature Cell Biology.* 2:70-75.

Willingham et al., "RNAi and HTS: exploring cancer by systematic loss-of-function," 2004. *Oncogene*, 23:8392-8400.

Worth et al., "Autosomal Dominant Cerebellar Ataxia Type III: Linkage in a Large British Family to a 7.6-cM Region on Chromosome 15q14-21.3," 1999. *Am. J. Hum. Genet.* 65:420-426.

Yahata et al., "Multi-gene Gateway clone design for expression of multiple heterologous genes in living cells: Conditional gene expression at near physiological levels," 2005. *Journ. Of Biotechnology.* 118:123-143.

Yan et al., "Conversion of diploidy to haploidy," 2000. *Nature* 403:723-724.

Zhang et al., "An Enhanced Green Fluorescent Protein Allows Sensitive Detection of Gene Transfer in Mammalian Cells," 1996. *Biochem. And Biophy. Research Comm.* 227:707-711.

Zuo et al. "Neurodegeneration in Lurcher mice caused by mutation in δ2 glutamate receptor gene," 1997. *Nature*, 388:769-773.

* cited by examiner

Fig. 3A
American SCA5 mutation

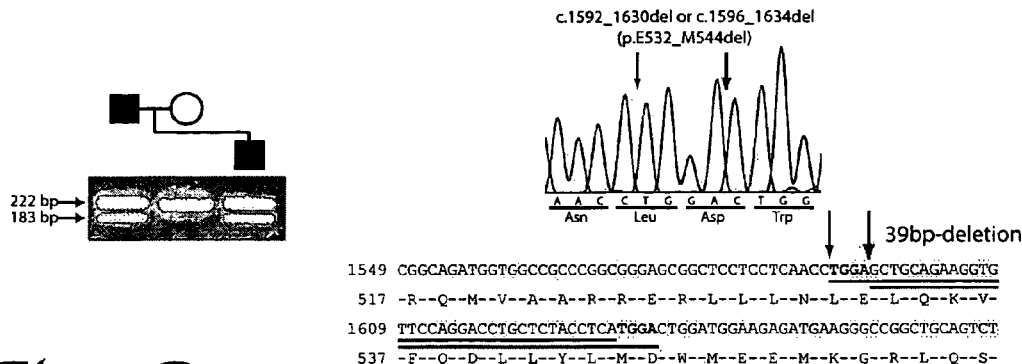

Fig. 3B
French SCA5 mutation

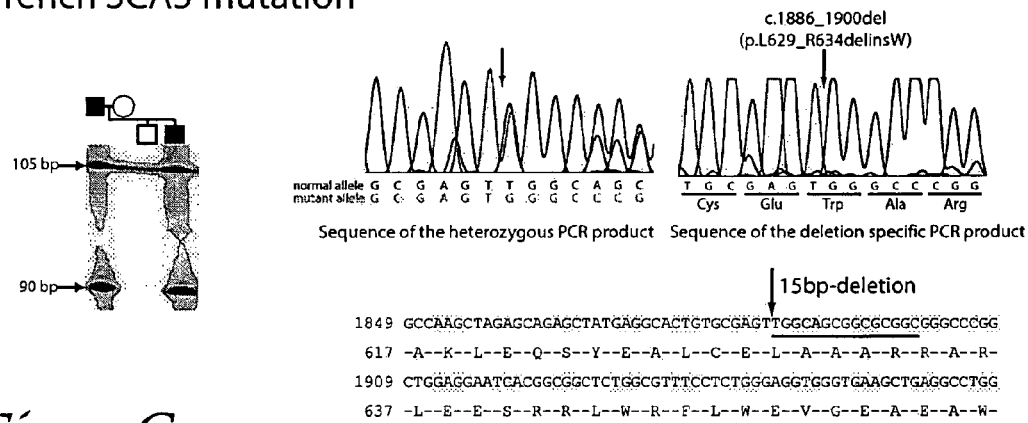

Fig. 3C
German SCA5 mutation

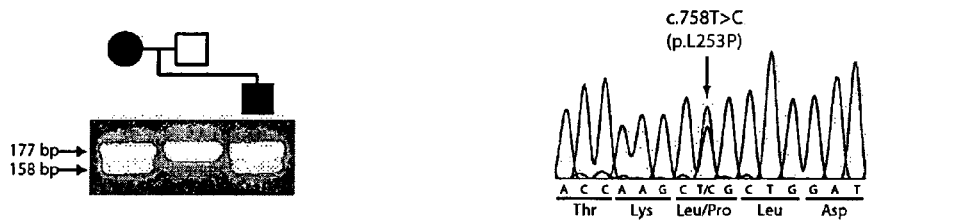

Conservation of calponin homology domain and leucine 253 among human beta spectrins

```
SPTBN1   SNAHYNLQNAFNLAEQHLGLTKLLDPEDISVDHPDEKSIITYVVTYYHYFSKMKALAVEG
SPTBN2   CNAHYNLQNAFNLAEKELGLTKLLDPEDVNVDQPDEKSIITYVATYYHYFSKMKALAVEG
SPTB     SNARHNLEHAFNVAERQLGIIPLLDPEDVFTENPDEKSIITYVVAFYHYFSKMKVLAVEG
SPTBN4   SNANYNLQRAFRTAEQHLGLARLLDPEDVNMEAPDEKSIITYVVSFYHYFSKMKALAVEG
SPTBN5   DRPLHNLAFAFLVAEQELGIAQLLDPEDVAAAQPDERSIMTYVSLYYHYCSRLHQGQTVQ
```

Evolutionary conservation of calponin homology domain and leucine 253 among species

```
Mouse   Spnb3       LKKCNAHYNLQNAFNLAEKELGLTKLLDPEDVNVDQPDEKSIITYVATYYHYFSKMKA
Rat     Spnb3       LKKCNAHYNLQNAFNLAEKELGLTKLLDPEDVNVDQPDEKSIITYVATYYHYFSKMKA
Dog     SPTBN2      LKKCNAHYNLQNAFNLAEKELGLTKLLDPEDVNVDQPDEKSIITYVATYYHYFSKMKA
Human   SPTBN2      LKKCNAHYNLQNAFNLAEKELGLTKLLDPEDVNVDQPDEKSIITYVATYYHYFSKMKA
Chimp   SPTBN2      LKKCNAHYNLQNAFNLAEKELGLTKLLDPEDVNVDQPDEKSIITYVATYYHYFSKMKA
Worm    unc-70      LQKSNALYNLQSAFDTAENQLGLAKFLDAEDVNVDQPDEKSIITYVVTYYHYFNKLKQ
Fly     beta-Spec   LSKTNAIHNLNNAFDVAEDKLGLAKLLDAEDVFVEHPDEKSIITYVVTYYHYFSKLKQ
```

Fig. 6A

```
CCACTGAGCAGCCAACCGCAGCCTCTGGCCACAAGGAGAGCGGAGCACAGgtagggcaag
............................................

aagacagaaggccccggtggtgagtggagggcttggtggtccctggacacccctcactgg ccacattctccttgcagGAGCAGGAAGCCGCCTACCACCATGAGCAGCACGCTGTCACCC
                  ....................-M--S--S--T--L--S--P-

ACAGACTTTGACAGCTTGGAAATCCAGGGCCAGTACAGTGACATCAACAACCGCTGGGAC
-T--D--F--D--S--L--E--I--Q--G--Q--Y--S--D--I--N--N--R--W--D-

CTTCCTGACTCGGACTGGGACAATGACAGCAGCTCGGCCCGCCTCTTTGAGAGGTCTCGC
-L--P--D--S--D--W--D--N--D--S--S--S--A--R--L--F--E--R--S--R-

ATTAAGGCTCTGGCAGgtgaggtcagaggagggtcgaggtgggggatgctggaggaggc
-I--K--A--L--A- tttgtcagctcgtcatgaagagccctttaactttatgggaagactgacttttctttctaa gtgggagacccagagcactctatcaattccctggtccccacatccagcctcaagaatagg ctccaggccattcagaactttccccagctcttccccccaagcatagagacgcttcactgg cccctggactggctgagctgactaaaacagcttccctctctggcctcagcccccgggtca tgtcccttcatccttcggcactctcgctcttgccactcctttctccgcctacctctccct tacctgtcatgcccttgttgtgtcttctttgatttccactgtcatttcccacacctgttc ccagtctattattcccctctgctccctctccacctgttccttccacctgccacctgttac tcccattatctcatctgcctgttccctgaagcaggttccctccacccgctgctgctggtt tctgcagccgcccattctccctggtgtgctctctgcctgccttggctcctactcttccct gcagcccagggcctgggctctccgctctgagcggaaactcgtccaacggcctccctgtct tccgggggaggagttgtcatggcaacaagagtgcggctgccacctgacaccaccagtggc tggcatggggctgactcacccacacaccccaaggccacctacccgtctggcttcctcct ccatcccactcttgtcattgccattgacctgctggctgcccagcccagcccaacccaacc cagtctgaggggtcccagctactctcaccgagaggtggtgctccgagtgggggtgggggt tggccactagaagaagagagactccaagggggaggttcccaaacctggccacatgtttta caggatcacccagggatgttttttacaaatacaggtttccaagcccctccctagacacaa taagttagaatcttggtccagaactcaggattttcaaaagctccccaagtgattctttt gagccagctcagcaccagtctgaggaccccttgtggcagccatagcttcccaggacccc
```

Fig. 6B ttctcatttctcctgggcctctctgtccttctggttgggtcttcaggccggctgtgaaa cactcctaccagtgtgtctatacatcagagaagacagaaggtgtgggttatggagaatgt catgtttgggggaaaatgttcctggcactctggttttggattcatgtagcctctagaactg tcatgatgtctatgtgtgtacaacatgtgccacccaccatgtttgcacacatgacaaatg rs11602953
ccatccaggactgtccaccatgcctgtgtacataggacacatgcctcccaggactctcacc atgcctgtgtacataggacacatgccacccaggactgtcaccatgtctggctgcacataa cttgggccacccagcactgtcaccatgtctgtgcacacatctgtgtgacctcgtgctctc attgggtgtttatctccaccactgaactgggctctcctgaagaggcagctctgcatggga tttgcctagcactgtgtctccagccagtaggtgtcaaataaacactgaatgaatgaagat gaggaagggcaagtgtaggctgcacatgacaaacgctgaagcccagaggaagggcgcctg gtatatgtgcccagcagcggggcgtctgggggcagggatggcctggtggaggatggccct ggtgggccagagggcagggaaggggctggcactggaggtggtgataagcaagtggaaagg atggtaacagccctcgtttcacagatgagggagtgaaggaaaatgcctcgcacagtgcct ggcttttcctctttgaggatttcctcgtttccagatttctctttgtctgtttctgagctg gggctcaaagcccacacatcctggagaaggacctcccagagtcacccagagaggggtcgc cctcgctgttcctgcaaacctctgggaaacaggagtttgcattgggggcccctctcgtgg gtcctgtgcattgttaggtaacttggggcctgatgggcgggtcttgaaggcgctggcagt gccctcctccgccgccccgcagggcctggccctgccccgccggccacactccgcctctc tcccctccccaacactgtccaacctgtttgtctggagccgcctgtctcctctcaccgcag ccaggcgtgcccccactctctgtctcaggagttcgggacaccccgtaactctttttgcca ctccttgaaattcccaccattcttgaatcccctgacgctggactccagcctgaggttcca rs551708
ctggggaacagaaactggcccctgccagcggggagcatggactctgggccctgggctct rs7118311
gtaactagcagctggcagcatgaatgggaacggagtgagcagggtgcacgggaacggcct gcatgaggccagcgagttttactatgaggctgtggaaggggcccacaaccccgggggcct cctgctttcaccagctgctttcatcaaccctgctcagtatgccagcgtgctggaaggacg cttcaaacagctgcaaggtgaggcccggggggccccctgtggggacgactgtgcctgggcg agagggacctgggtgtggggagagtggccggagctgaggacctggcacaggacacagtgt gactccagtgtttgtgttgggagacaacgtgatgcagcttagaggggataattacaagag

Fig. 6C rs11820790
gccggaaaatacacagatgtcaacggaatggggaaaggcttggacctgctggcagggacc gtgtatgatggcatgggtgggtgtgactgccgggccttggggtgctgcatggagcaaagg caactagccatggagggcgtgggggtgccagcacctggggaggcgccagcagtgcctctg aggtggatccggatctggcggtggagcgctggccaggacagttaggggaggcggaggggt gagccaggcccagggacctggagattgtgttttccaggcctctgagcgtgtgtctgaatg tgtacacgggggcagtgtgtgtggaagcaaagggagtgtctcgaaggagaggatctgtgc aaacaggcccaggtagatgtctgcgcaggtgtgttcactctggcacaagtgcttaggt gtgtttttgggaatcactgttgtgtgtgtgtgtaaggatctagggatgctgtgggcgt cttgtgacgtgacacttggtttctggtgcttggctttgcccattttcctcctagttgcca ctaattctgtgtcttctgactgtgtgccaaaatggcctcaccccagggtgcccagcagta gggcagtgcccctggatccagcaatggcctgtgaccacgctcctcctggctcagatggg gcctgtagacctgccgggaggccccaaggcaccttggtttcatgggtgctggggagcatg gggccgtcccatgttattaggaccccaggtttggtgccagtatagtggctggaggtgaaa gacacggagcgacgtgggtgtgttgctgtgtcttatgggtgaggtgcttaggaatgtgag rs4930389
attaagggatgagtctttccggtttctgagatgctggtgctgagacggaagcaaaagtga ctcttcagaccccagccacttgggttgggtccttgcacagggctctctgtgggaaagtgg cagaaatcctcatcaccagagcagtttctgatgctttcactttgtcacttagaacgttct taatttttattttcctacggaacctagtatttacttcccctcttcagtagctcccctccc ctgtgggctgggcagcagggcattgcctaactttttttgagattggtacctaactctgc ctggcttttttccccatgtttcctggcctcactgttttcccagttcccaactctcaac atcttgttcttctaagcaatggggtgtttatgtcctggaactggatccccttgcagccag ctgaatgtactgtccccaaccccagaagcagaggagcctgccttttctttaagttatcc aaggacagtaagctgactcaggaggcctgcagcctctataccatcaagtcctaatgaccg cttggaagagccgctgcaataattttagcccacaccttctcctttgtctgcaaccaaaag agaacagccatacctcccaccggcctgggcagctcttgctctccttcgggccagatcaca ccactttataacagcagctcaccaaggagccattttgtgccaggcaccaactagttgttt rs5792396
tatataccttatctcatttaatcaacacaatgacctgttgaagtagaaagtgatgttccc attttacagatgagacattggggctctgatgaatgaagtcacttgaccagcattccactg

Fig. 6D

```
cttccacgactgccccatcccagcccctccctgcatgtccatggtttctgaggatgaaa
                            rs658538
ggtcttcatcctttcttctcaaagcctattttcttttcttttcttttcttttttttttt gagacggagtcttgctctgtcgcccaggctggagtgcagtggcacaatctcggctccctg caagctcccctcccaggttcacgtcagtctgcctcagcctcccgagtagctgggactac
                            rs657696
aggcgcccgccactatgcccggctaattttttgtaattttagtagagacggggtttcacc
                                        rs10702473
gtgttagccaggatggtctcgatctcctgaccttgtgatccgcc-cgccttggcttcccaa agtgctgggattacaggcatgagccaccacacccaaccttcgcctattttctgtctttca
                                   rs9666734
tctttcttctttaccttgcttatgagctcattgcaagttacgggctttcctcccggtcat cttccttcccttcctcctccttagaggaccccgcttcccatctctcaggcttctccatcc cccacccctgccaactggtgtttagaagcaggcatactgaactcgagggacagaaataaa cccatgttgccaccacagATGAACGAGAAGCTGTGCAGAAGAAAACCTTCACCAAGTGG
                   D--E--R--E--A--V--Q--K--K--T--F--T--K--W-

GTAAACTCGCACCTGGCCCGGGTCACGTGCCGGGTGGGGGACCTGTACAGCGACCTCCGG
-V--N--S--H--L--A--R--V--T--C--R--V--G--D--L--Y--S--D--L--R-

GACGGACGCAACCTGCTGAGGCTCCTCGAGGTGCTCTCGGGAGAGATACTGgtgagctgt
-D--G--R--N--L--L--R--L--L--E--V--L--S--G--E--I--L- rs12805133
ggtcatgaagggaagtgggggggcct-tagaaaagtgtccaaggggaccagctggaagaac
                                                      rs11828633
agccctcagagagagtgacggcacagggcgggaagcagtggctccctctgctcagaggat gggttcatttcaagtgcctttgccacttagattacataggagcattgcttcatggagaca
        rs5792395
ggaacagtggcccattgaaaacatttcttttcccacctactctgggtgcaattaattcc cttgggaatcttaatctgcccaagcctcatctgtaagctcagctttggctccagccctgg ggctgtgcctgtctgtgttcctgaggtaggtcatggggaaggtgtgcaaagctgggccct gtgaaggctggggaagaaggtggaagcccacagtcccgtgccattttgccccgtccctc cacagCCAAAGCCTACAAAGGGCCGCATGCGGATCCACTGCCTGGAGAACGTGGACAAG
     -P--K--P--T--K--G--R--M--R--I--H--C--L--E--N--V--D--K-

GCACTGCAGTTCCTCAAGGAGCAGAAAGTGCACTTGGAAAACATGGGCTCCCATGACATT
```

GTGGACGGAAACCACCGACTGACCCTTGGGCTGGTCTGGACCATCATCCTTCGATTCCAG
-V--D--G--N--H--R--L--T--L--G--L--V--W--T--I--I--L--R--F--Q- gtaccccagcacactgtcacacagggtgtggttcctgccctggctctgcaccgcaagccg ttcctgctggcccatgacacaacaaacacaaagatggaggatctagaaccttatgtagca gctgccatggcggcgctatccaagcaccagatcagtggactcccctctttcagcagggta gaaaccagcttgggtgaatgtcacaccctgtggcaaattccctgtgttctggtctgtgt gttggtcgtgtgcaatgggaccaggaccacaggttggtccacaggagactggaagtttta ccaactggtccttcaccacagggatttgggaacttctagagggtctggtcactggcacca attccctgccataaactctgcctgcctccccaatggaacagtcaccctcctcctcctca
                    rs529203
tgccccagtgtcctcatgccatcacagcgttcctgatcaccccttccttcccgggttct gtcggcttcaccttggagagccagcttttagagaccttggagagccagctctcagaaaat gttcactcttctgcctgcagttccccacctggagggaccagcaccctccactcagacaca cccattcttcagcatcctaccctaatctgctgcctcaaatcccttgcacccagtgttttg tggtccctggcctaggttgaaaggacctcaggctatgcctgtccacccattaccacagt ctaaagagcagtttcctgccatttatctgagcatctctgataacaccaggagttcctgtc cagggactgagggccctgcttgcttccttcctagATCCAAGACATCAGTGTGGAGACA
                                    -I--Q--D--I--S--V--E--T-

GAAGACAACAAGGAGAAGAAGTCAGCCAAGGATGCCCTGCTTCTGTGGTGCCAGATGAAG
-E--D--N--K--E--K--K--S--A--K--D--A--L--L--L--W--C--Q--M--K-

ACTGCAGGgtgaggacaccctgggcgtgtggcactggagggtcagtgaccccaggctgt
-T--A--G gctgggctccaggaaccatgagctggtgactgccctggagtcatagaacagagctcagcc ctactcaccattttctgaatctctgtttatagTTATCCCAACGTCAATGTACACAACTTC
                                  --Y--P--N--V--N--V--H--N--F-

ACCACCAGCTGGAGAGATGGACTAGCTTTCAACGCCATCGTGCATAAACACCGgtgagaa
-T--T--S--W--R--D--G--L--A--F--N--A--I--V--H--K--H—R gatggggttagcaaacgcagcagagctgctgggtcggctaatgacctggggtgcacatgt ggagacagagatgagatgagctgcacagcagtcagacggaaggaatagcactcggagcag aaccagaacatgggggtgcagggctgcgcagagcacttgtgatgggaagcaggggaggtg
```

Fig. 6F gtgtggggagggctgtgagcagcagtgtgggtttgggatgcctacttctggacaaaatt rs615536
gggtcggtgacttagggataaagattggtgtgggtttcctcttcctcttcgagatctcac atgtttctgatcccttctgtcttgcctccccacccagGCCAGACCTGCTGGATTTTGAG
                                        --P--D--L--L--D--F--E-

TCTCTGAAGAAGTGTAATGCACACTATAATCTGCAGAATGCATTCAATCTGGCTGAAAAG
-S--L--K--K--C--N--A--H--Y--N--L--Q--N--A--F--N--L--A--E--K-

GAACTGGGACTTACCAAGCTGCTGGATCCCGAAGgtggggccagagctatgtgaaaaaga
-E--L--G--L--T--K--L--L--D--P--E-- ggtggtagggtagagacaggaggtggaccagtggttgccaggggctgcggaggggaaga catggagtaaccaccaactgatacaggggcttctttggtgggggaagagaatgttctgga attagaaagtggtgatggttacacaaccttgtaaatatactgaaaaacacgtggttgctc acacccagcactttgggaggccaaggcaggaggatcacttgagcctaggagtttggtacc agcctgggcaacatagtgagaccccatgactacccctccccccaaaaaaaatatatatc tttacactgaaaaccactgaattatatacattgaaaggttgaattttatggtgtgacaat rs577595
catttctcaggtttttttttttttaacaaaagactgtaggtaggaagaaaggcagccca gtgacagaaagagccctggactgtgggttgtgtcccaggcagagcacagaggagctctgt rs580024
gacatacagccagtggctagcctctctgtggctcagtttcctcatgtcttaaaagagaga attggtctctaagggctcttctgaaattctaggattctaaattaagctacatgttgctgg ccacggtggtacctgcctatagtcctagctgctagtgaggctgaggcgagaggatcactt gagcccaggagttctaggctgcagtgggttatgctgattggatatctacactaaattcag cactggtgacctcctgggagcaggggaccagcaggttacctaaggaggactgaaccagtc caggtcagaatggagcaggtcaaaactcccacactgatcagtagtgggatcacacctgtc aatagccacagtactccagcttgggcaacagcgagacccatctctatttttttaaaacaa attttaagaaaaaaaattaagctgcatgaccttccactctcacccagaactggcctgta gtcagctgaccttgctgattggttcctgtggttctggtcataatgccgatgagatcgatg rs554305
agatcagtaacagccactgggctctttttttttttttgagacggagtctcactctgttg cccagactggagtgcaatggcgcgatctcggctcactgcaacctccgcctcctgggttca agcaattctcctgcctcagcctcttgagtagctgagattacaggcgcatcccaccacgcc

Fig. 6G cggctaattttgtatttttagtagagacagggtttcaccatgttggtcaggctggtctc taactcctgacctcgtggtccgcccacctcggcctcccaatgcgctgtgataacaggtgt gagcccccgcgcctgactgcgattaggctcttatttgatacctggttctgcacttgatgt gttttaatcttcacaacaccccttttgaaatcagtactgttgttatcctcagtttatggaa gagaagatgggggcctataatgggtaagcaacttgcccaggtcctccggcagatggagct gagattggcgttcaggcagcctggctccagagcctgtttcctccgctgcctctgggaaag tggagaccaatcttggtgcaaccagaacagggaggagagaaaggctcgcctgctggaggt gctccttaagttcactgggtggatgttcactggtcttggccattttctccctgttttcca ttctacctgtagccctatcacctgggccttttactgcagaatgacaagtgtcagcgagc tagcaacagacataggcttcatgcagtgctccttggagagcctctgggtagcatggctgt aattcagaacctggaaataaagctaagcattctgtaactttccgagatgacttcagtggc tcctgcctgcccatgtatttccagaaataggcaagaggcttctggtctcatagtcttacc tttaggataaaatctggcctatttaaaagaacccacagatttcaagttatggtcagcctc agttgtgcgctggaagccaattcggcttgaaagacactcccctccttgggcccacagctg agctttaggattgaggttagaaacggcgtgatcacacctggagatggtgctgagagctgg cctctgtccccactgagctgcagggatcacagggcccatcgatctgagcatcctaggttc aggaggcttagttcataccttccgtcccactgcccctcaatccattgacttcttaaacat tattctagcctaaaagtccatgatccatccccacatagcaatgctgtttctttctttgct tttcttccccaaacaactgattttggtctccacggggaactctgggtaaaagcttccttg tgcttctggggtttgtgctctgcttggagggccttcttgtttccaggagaaggggaaaa aaagatgagcttttggtgccttttcatttgaatgggtaagttgtcattttgctctaaa aggagatggagagatgtcagccttggaggactgggcaggcccagggtttggggtaagtga tgcaagttatggatgaacttctgggaggcctgacccaaatggtcctctcttgcagACGTG
                                                        D--V-

AATGTGGACCAGCCAGATGAGAAGTCAATCATTACCTATGTGGCTACTTACTACCATTAC
-N--V--D--Q--P--D--E--K--S--I--I--T--Y--V--A--T--Y--Y--H--Y-

TTCTCCAAGATGAAGGCCCTGGCCGTGGAAGGCAAGAGAATTGGCAAGgtactgtccatg
-F--S--K--M--K--A--L--A--V--E--G--K--R--I--G--K- ggcagtaggcataaaggccagaggaggcccggctgagggtcttactgccctagtgcaag ggcagggtggagctgcaggactgggccagggaccctgtggctgggactgtcacgtccctg

Fig. 6H

```
tcttctgcctcccagGTGCTGGACCATGCCATGGAGGCAGAGCGCCTGGTGGAGAAATAC
               -V--L--D--H--A--M--E--A--E--R--L--V--E--K--Y-

GAGTCCCTGGCCTCGGAGCTGCTGCAGTGGATCGAGCAAACGATCGTGACCCTCAATGAC
-E--S--L--A--S--E--L--L--Q--W--I--E--Q--T--I--V--T--L--N--D-

CGGCAGTTGGCCAACTCCCTTAGCGGGGTCCAGAACCAGCTGCAGTCCTTCAACTCCTAC
-R--Q--L--A--N--S--L--S--G--V--Q--N--Q--L--Q--S--F--N--S--Y-

CGCACCGTGGAGAAGCCGCCCAAgtaggtgtccctggggccccaccctttccctgagctgt
-R--T--V--E--K--P--P--K gctcccacgagaggaagcctaaattagcacagccttcagggagggaaatttggcagtaca taaatgcagtggagatttcccacaccagaagcatccaaacaacatagttgatacaaaata aaattttttaatgattagtcgttttttaaaaatcatgctgtgggccgggcatggtggctca cgcctgtaatcccagcactttgggaggccaaggcgggcgcatcaccgagaccagtctggc caacatggtgaaaccccatctctactgaggtcgggagtttgagaccagcctggccaacat ggtgaaaccccgtctccactaaaattacaaaaaaattagctgggcatggtggcacacgcc tgtcatcccagctactcgggaggctgaggcaggagaaccacctgaacccgggagacagag gttgcagtgagccaagatcacgccactgcactccaacctgggtgacagagcaagactccg tctcaaaaacaaacaaacatgctgtggaaatgattgctatgatgtgttgagtcagtgcg atccatcagataagattactgatcaggtgtcatggcaacccaatcctagcataggataga ggggactggacctgacaggcaggtcacaaccggcaacatgggtgtggctggtaacgtgag aattgcagaggttcttatcatttcagtattttagcaattaactgttccaagtatgtgatt gctgttaggcaattctgttcagtacctgccaaaacgtctgtgtttatgctgtcatggagt tcttttggagttaatatatatcagctctgaaactaatattagtccagaaaacaattgttt ctatacattccagggaatgatttaaggtgtacccttaacctaggaagttgtcttctgga cattaaacaaagatgtagcttcaaggatgtttatcaacacaaccactagaaaagaaaaat aagtcatgggcagccactgaaaataatattaaagaaatgcatttattgacatggaaaggt gttcatgaaaaataagtgggggaaataggttataaaagaattattttggctgggcaccgt ggctcatgcctgtaatcccagcactttgggagactgaggcgggtggatcacttgaggtca ggagtttgagaccagcctggccagcatggtgaaaccccatctctactaaaaatacataaa ttagccaggtgtggtggtgcatgcctgtaatcccagctactcgggaggctgaggcaagag rs645307
attggcttgaacccgggaggcagaggttgcagcgaacccagatcgcaccactgcactcca gcctgggtgacaaagcaagactctgtctcaaaataaaataaaatgatgttcttttggtta
```

Fig. 6I

```
gcccatattttctggcttccacataaaaagtttatattgcttttgtaagaagaaaagcaa cacaggacacccatttggaagagtaaagagtccttgtgaccctcgtgggctttaattctg accccaacccggcctcctgcctcagGTTTACCGAGAAAGGGAACTTGGAAGTGCTGCTC
                         --F--T--E--K--G--N--L--E--V--L--L-

TTCACCATCCAGAGCAAGCTTCGGGCCAACAACCAGAAGGTCTACACGCCCCGCGAGGGC
-F--T--I--Q--S--K--L--R--A--N--N--Q--K--V--Y--T--P--R--E--G-

CGGCTCATCTCGGACATCAACAAGgtccgtggctgcccacaggccacccaccctcagggc
-R--L--I--S--D--I--N--K- aggccctggcccagatgccttgcacacatccccaaacccggggccatgtcgaccttcacc aagttctactatctgctgccccaacttgaaactcgagcactctgcccagctgcccacact gtgccagatgtgattctcccatcctctcaggcacacggctccctgtcctttgtctgact ctccatacgaggtcacataaggaaattatgccccaagttcctcagcttgttaaacctgtc cccaactcactatcccttctttatttttttcacaatattgtaagattactaaaagtaaa aataaggttcgcacacagtcctgccaacacaaaggaatcagatggtttccactgttcgtg ctccctccagtccttttccagaagcttctacatggcttcacagactcccagcgctgccct gtttcctgtttccacgcccaggcgtctcacccactgcattccacggatccaccagaccga gcttccatgggacttaccatgtgcctccagccccactgagccctccccaccctgtccctt ccactaaccctgtccccacccatagGCTTGGGAGCGGCTGGAGAAGGCGGAGCACGAG
                         -A--W--E--R--L--E--K--A--E--H--E-

CGTGAGCTGGCCCTGCGCACCGAGCTCATCCGCCAGGAGAAGCTGGAGCAGCTGGCCGCC
-R--E--L--A--L--R--T--E--L--I--R--Q--E--K--L--E--Q--L--A--A-

CGCTTCGACCGCAAGGCTGCCATGCGGGAGACCTGGCTCAGCGAGAACCAGCGCCTCGTG
-R--F--D--R--K--A--A--M--R--E--T--W--L--S--E--N--Q--R--L--V-

TCCCAGgtaggacttgaggctcctaggatgcttaggctggtcagaactgggagagagaca
-S--Q- gggtggataagaagccccgcggggtggagagacaatgaaacacaaaatccgtcacctggg taaaaaggcctagaggtccgggagccagggggccagagggtgggacaggagagagggttgg tgagacaggatggggtgggatagagagggaacttagagccaccgcatggagctgggatc ttgcaggccaagtgccctgcaggacagaggagcaggcagaggcactgtcccttggtcccc acacctcctctccctgcccccgacacagGACAACTTTGGGCTGGAGCTGGCAGCTGTC
                             -D--N--F--G--L--E--L--A--A--V-

GAGGCAGCAGTACGGAAGCACGAAGCCATTGAGACGGACATCGTGGCCTACAGCGGCCGG
-E--A--A--V--R--K--H--E--A--I--E--T--D--I--V--A--Y--S--G--R-

GTGCAGGCAGTGGACGCCGTGGCTGCAGAGCTGGCCGCCGAGCGCTACCACGACATCAAG
```

Fig. 6J

```
-V--Q--A--V--D--A--V--A--A--E--L--A--A--E--R--Y--H--D--I--K-
CGCATCGCCGCTCGGCAGCACAACGTGGCACGGCTCTGGGACTTCTTGCGGCAGATGGTG
-R--I--A--A--R--Q--H--N--V--A--R--L--W--D--F--L--R--Q--M--V-

GCCGCCCGGCGGGAGCGGCTCCTCCTCAACCTGGAGCTGCAGAAGGTGTTCCAGGACCTG
-A--A--R--R--E--R--L--L--L--N--L--E--L--Q--K--V--F--Q--D--L-

CTCTACCTCATGGACTGGATGGAAGAGATGAAGgtaccagtgaggcgtgctgggtgggt
-L--Y--L--M--D--W--M--E--E--M--K- aagagtgatcaagagtcgagggggccccacagtgggtgcgtccgcccgtctgctcggccg atctctgtggagtgtgaaccagcacagggccctgtcccagttgcagggaacaaagtaaa cagggccctgtccacatggggttcgtgtccacatggaggaggctgatgacaaacccacg gacctttccgtaaacaaaagagcaggggccataaaaccactgatgaaactggaacaggt ggtgtgaggggctggtcagacaaggcctctgagaaataccatttaagccgagaccagaa tagtgccaggagccagcacagagagctctcaggagagaatgttccgggcagaaggaacag ccggcacaggccctcggcctggatcagcatggtgtgttcaggatcagaaggaaggccggt gggctgtgagcatgaggagtgggggccatggactgagatttgggagggcacggccagccc actagggccttacaggcctggtcagggagtttggatttattcaaagtaacatggatcct ttaaagtgatttgaaggggccaggcgcagtggctcatgcctgtaatcccagctctttggg aggccaaggcaggcagatcacttgaggtcaggagttcaagaccagcctggccaacatggt gaaaccccgtgtctataaaaatacagaaattaaccaggtgcggtggtagcgcatgcctgt agtcccagctactcaggaggctgagacagcagaatcgcttgaacccaggaggcggaggtt gcagtgagccaagattgcaccactgcactccagcctaggtgatagagcaagactcagtca
                    rs11227576
aaaaaaaaaaaaaaaagcagctaggcaaggtggctcacgcctataatcctaagactttgg gaggccgaggcgggcggatcacctgaggtcaggagtccaagaccagcctggccaacatgg tgaaaccccatctctgctaaaaatacaaaaattagctgagtgtggtggcacacgcctgta atcccagctagtcaggaggctgaggaaggagaattgcttggacctgggaggtggaggttg cagtgaactgagattgtgctactgcactccagcctgcactacaggagcgagactccatct caaaataaataaataaataaagtgattagaaggttttgagagggggagagatttgattgt accttatgtttgtaaaaaagtcactttggctactctgaagaaggcctgtgggcaggcagc atgacagcgagaccgttagaggttgctgccatcttccaggcgggcagcggctaggagggt ggattggggagagatgtggaaggaaggctgctgggtgctggggcggagcggtggcggcag
```

Fig. 6K

```
gagggtgtcgatgattctgaggctgagaagattagtcacagcaaagcttccaagagcagg agttagttagaacattgttccacagcaggggagttcaggataaggaggtcggggtgccag ggcagaactggggtatctcaagtatgtgtgagcaagcaggtttctcacctgggtgcaaca cctggggccgtggagaagttggaagaaaaacgcagccaggttagcgcgtctgtgctcagg cgggcatgtgcacttcatgtgtgcctggcag
```

```
GGCCGGCTGCAGTCTCAGGACCTGGGCAGGCACCTAGCAGGAGTGGAGGACCTGCTGCAG
 -G--R--L--Q--S--Q--D--L--G--R--H--L--A--G--V--E--D--L--L--Q-

CTGCACGAGCTGGTGGAGGCAGACATCGCCGTGCAGGCCGAGAGGGTGCGGGCCGTCAGC
 -L--H--E--L--V--E--A--D--I--A--V--Q--A--E--R--V--R--A--V--S-

GCCTCTGCCCTGCGCTTCTGCAACCCAGGGAAAGgtgagaagtcagcgaaggcactggag
 -A--S--A--L--R--F--C--N--P--G--K--
```

```
agggaggggctgggaaggagcacatcaagagccgaggtggaagggttgggaaacctgggg acgggaaagatggtggccaaacgatggtgactgagctaaagccagggagggaagtccaag agagtgtggtggcagggagcagccggagggctgggttaaggctctgaccctctcctgtga
```

```
ctttctcagAGTATAGACCTTGCGACCCGCAGCTGGTGTCGGAGCGGGTGGCCAAGCTA
          E--Y--R--P--C--D--P--Q--L--V--S--E--R--V--A--K--L-

GAGCAGAGCTATGAGGCACTGTGCGAGTTGGCAGCGGCGCGGCGGGCCCGGCTGGAGGAA
 -E--Q--S--Y--E--A--L--C--E--L--A--A--A--R--R--A--R--L--E--E-

TCACGGCGGCTCTGGCGTTTCCTCTGGGAGGTGGGTGAAGCTGAGGCCTGGGTGCGGGAG
 -S--R--R--L--W--R--F--L--W--E--V--G--E--A--E--A--W--V--R--E-

CAGCAGCACCTCCTGGCCTCAGCCGACACGGGCCGAGACCTGACCGGTGCCCTCCGCCTG
 -Q--Q--H--L--L--A--S--A--D--T--G--R--D--L--T--G--A--L--R--L-

CTCAACAAGCACACAGCCCTGCGGGGCGAGATGAGCGGCCGGCTGGGGCCCCTGAAGCTC
 -L--N--K--H--T--A--L--R--G--E--M--S--G--R--L--G--P--L--K--L-

ACCCTGGAGCAGGGCCAGCAGTTGGTGGCCGAGGGTCACCCTGGGGCAAGCCAGGCCTCT
 -T--L--E--Q--G--Q--Q--L--V--A--E--G--H--P--G--A--S--Q--A--S-

GCCCGTGCAGCTGAACTCCAAGCCCAGTGGGAGCGGCTAGAGGCCCTGGCCGAGGAGCGT
 -A--R--A--A--E--L--Q--A--Q--W--E--R--L--E--A--L--A--E--E--R-

GCCCAGCGGCTGGCCCAAGCCGCCAGCCTCTACCAGTTCCAGGCCGATGCAAACGACATG
 -A--Q--R--L--A--Q--A--A--S--L--Y--Q--F--Q--A--D--A--N--D--M-

GAGGCCTGGTTGGTTGACGCACTGCGCCTGGTGTCCAGCCCCGAGCTGGGGCACGACGAG
 -E--A--W--L--V--D--A--L--R--L--V--S--S--P--E--L--G--H--D--E-

TTCTCCACGCAGGCTCTAGCCAGGCAGCATCGGGCCCTGGAGGAGGAGATTCGAAGCCAC
```

CGGCCAACCCTGGACGCCTTGAGGGAACAGGCAGCAGCCCTGCCCCCCACACTGAGCCGC
-R--P--T--L--D--A--L--R--E--Q--A--A--A--L--P--P--T--L--S--R-
            rs4930388
               R
ACGCCCGAGGTGCAGAGCCGGGTGCCCACCCTGGAGCGGCACTACGAGGAGCTGCAGGCC
-T--P--E--V--Q-=S=-R--V--P--T--L--E--R--H--Y--E--E--L--Q--A-

CGGGCAGGCGAGCGAGCGCGGGCCTTGGAGGCAGCCCTGGCGCTCTACACCATGCTCAGC
-R--A--G--E--R--A--R--A--L--E--A--A--L--A--L--Y--T--M--L--S-

GAGGCCGGGGCCTGTGGACTCTGGGTGGAGGAGAAGGAGCAGTGGCTCAACGGGCTGGCC
-E--A--G--A--C--G--L--W--V--E--E--K--E--Q--W--L--N--G--L--A-

CTGCCTGAACGCCTGGAGGACCTGGAGGTCGTGCAGCAGAGgtaggcccctcaggctcct
-L--P--E--R--L--E--D--L--E--V--V--Q--Q--R rs3741359
agtgggaccagccttgggaggtgggggtgggggggccaggatgtgggtggtgagtccctc cataaacttcctgcctcacccctttgagtcttaatggttgtccatttctagttttaacaa aaaatgttaaccatactcacaagtagagacatttcaccacaaaccccctctacacccgtca cccagattcagtcattgccaacatcttgctctatttggttctctgccttttaaaaagca aatccccaagattagcacatccctcctaccttcttcagggtgtgccctttaagaaataca aggaagcggccgggcacggtggctcacacctgtaatcccagcactttgggaggccgaggc aggcggatcacgaggtcaggagtcgagaccatcctggctaacatggtgaaacgctgtct caactaaaaatacaaaaaattagccgggcacagtgggggcgcctgtagtcccagctact cgggaggctgaggcaggagactggcatgaacctgggaggcggagcttgcagtgagccgag rs11286358
atcgtgccactgctctccagccttggcgacagagcgagactgtctcaaaaaaaaaaaaaa aaaaaagaaaagaaatacgaggaagcattcttacctacaatatattattttcaaattgtc tgtgtggacttaaaatagctgaggctttgaagttataaacctttagacagagacactaa aatagttttatttacagaataaatcttcaaatcatttattcaataataaatcttaaaaat ttttttatagaaccacaataccattatcacatagaacaaaattaggaatttctttttttt rs12807346 rs12807677
ttgagatggagtctcactctgtcacccaggctggagcgcagtggtgcgatctcggctcac tgcatgctctgcctcccgggttccagcgattctcctgcctcagcctcccaagtagctggg actacaggcacccaccaccatgcccagctaattttttgtatttttttattagtagagaca
```

Fig. 6M gggtttcaccatgttagcgaggatggtctcgatctcctgacctcgtgatccacccggctt rs7929435
ggcctcccaaagtactgggattacaggcatgagccactgcgccgggtcaggaatttcttg rs7944095
atatgatctatgatcaatgtgtaatcaaatttcctggtgtttaaaaaaatataattaggt caggcctggtggctcacacctgtaatcccagcactttgggaggccaaggcaggagtatca cttgattccaagagttcataaccagcctgggcaacatagtgagactccacctctacaaaa ttttttttttaattagccaggcatggtggcaggcgcctgtagtcccagctactggggagg ctgaggcaggaggattgcttgagcccagaggtcgaggctgcagtgagctgagatcgtgcc actgcactccaacctgggtgacagagtaagaccctgtctcaaaaaaataaataaaaataa aaatgtaattaaagattttttttagttttcaaggtatcctaatgtagaggttaacaaact gcaaccttgggccaaatccagcctgctgcctgtttctgtaaataaagttttttttggtt ttttttttttttttttttttgagacggagtcttgctctgtccccaggctggagtgcag rs565670
tggcacaatcttggctcactgcaagctccgccgcccgggttcacgccattctcctgcctc agcctcccaagtagctgggactacaggcacccgccaccacacctggctaattttttgtat rs11601857
ttttagtagagacgaggtttcaccgtgttagccaggatggtctcgatctcctgaccttgt gatccacccatctcagcctcccaaagtgctgggattacaggcgtgagccaccatgcccgg tctgtaaataaagttttactggaacagagctacactcgcccttttgcgtattgcccgtgg ctgctttcaggctacagcagcagggctgaatagttgccgcagcagctgcatggctcacga agcctataatatttaccatcaagcccttcacagaaaacatttgcagaccctgccctatta gaacatcaaatgtcggccaggcgaggtggctcacgcctgtaatcccagcactttgggagg ccaaggcgggtggagcatgaggtcaggagttcaagaccagcctggccaagatagtgaaac acccgtctccaccaaaaatacaaaaattagctaggcttggtggcgggcacctgtaatccc rs12418602
agctattcgggaagcggaggcagaaaattgcttgaacccgggaggcggaggttgcagtga gtcgagattgcaccactacactccagcctgggtgacagagcgagactccatctcaaaaac aaaacataaaatgtccctggaagaagttatccttcacattttcatcactcagacaaatat ttttggttattacttcattttctaacacatattagtgggatgagacccagataggcagct aaggggggaagtcccaggaggctgagcagctctgataaagggttggccccatgccagggtc tagtttgacttgtgtgtctgttcctgacctttacctttcaccatcttttgagcatttcta

Fig. 6N

```
gcgatgacagttattctgcttgttttgggggagttgtgggttccttccttgatgcacaga tactatgaacctcataggctgagaggcagagagactcctgcagataagcctcctggtgaa ggagacaccctcctgggtgtttaagagaggtggacttaggtggactgggcacatcgctgc ctcccacaattcacgcctggctcttccaccctctcagGTTCGAGACCCTGGAGCCTGAA
                                     --F--E--T--L--E--P--E-

ATGAACACCCTTGCAGCACAAATCACCGCGGTGAATGACATTGCCGAGCAGTTACTGAAG
-M--N--T--L--A--A--Q--I--T--A--V--N--D--I--A--E--Q--L--L--K-

GCCAACCCCCCAGGCAAAGACCGCATTGTCAACACCCAGGAGCAGCTCAACCACAGgtgg
-A--N--P--P--G--K--D--R--I--V--N--T--Q--E--Q--L--N--H--R rs2276140    rs532439
gtttgggagggcaggaccaggaaactgacagaaaaatgaagcaatggggatggcagtgag aggcaggttttgtagggcctggaagggtggctacaaaggaggaagcaaaccagtctggaa rs2276139
tatgttggggaaggaaaaaggatgaaagagatgagagaggggggtcaaggtggtctgaagc rs11227575
ggctgctggccagaaagggaggagtgaaggggagctaccaagagagagagaagcagggaa gaagcttccaaacaggcctggccagggcaggaagctgaaccttcccccctgctctcagGTGG
                                                         --W-

CAGCAGTTTCGGCGTCTGGCAGACGGCAAGAAGGCAGCTCTCACCTCAGCCCTGAGCATC
-Q--Q--F--R--R--L--A--D--G--K--K--A--A--L--T--S--A--L--S--I-

CAGAACTACCACTTAGAGTGCACGGAGACCCAGGCCTGGATGAGAGAGAAGACCAAAGTC
-Q--N--Y--H--L--E--C--T--E--T--Q--A--W--M--R--E--K--T--K--V-

ATCGAGTCCACCCAGGGCCTAGGCAACGATCTGGCTGGGGTGCTGGCCCTGCAGCGCAAG
-I--E--S--T--Q--G--L--G--N--D--L--A--G--V--L--A--L--Q--R--K-

CTGGCCGGCACGGAGCGGGACCTGGAGGCCATCGCCGCCCGGGTGGGCGAACTGACTCGA
-L--A--G--T--E--R--D--L--E--A--I--A--A--R--V--G--E--L--T--R-
                                              rs506028
                                              Y
GAGGCAAATGCCCTGGCTGCCGGCCATCCCGCTCAGGCAGKGGCCATCAACGCCCGGCTG
-E--A--N--A--L--A--A--G--H--P--A--Q--A-=V=-A--I--N--A--R--L-

AGAGAGGTGCAGACCGGCTGGGAGGACCTCAGGGCCACCATGCGGCGTCGAGAAGAGTCG
-R--E--V--Q--T--G--W--E--D--L--R--A--T--M--R--R--R--E--E--S-

CTGGGGGAGGCGCGGCGGCTGCAGGACTTCTTGCGCAGCTTGGATGACTTCCAGGCCTGG
-L--G--E--A--R--R--L--Q--D--F--L--R--S--L--D--D--F--Q--A--W-
```

Fig. 6O

```
CTAGGCCGCACTCAGACTGCTGTGGCCTCTGAAGAAGGGCCGGCCACCCTGCCTGAGGCA
-L--G--R--T--Q--T--A--V--A--S--E--E--G--P--A--T--L--P--E--A-

GAGGCCCTCCTGGCCCAACATGCAGCCCTGCGGGGAGAGGTGGAGCGGGCCCAGAGCGAG
-E--A--L--L--A--Q--H--A--A--L--R--G--E--V--E--R--A--Q--S--E-

TATAGCCGGCTGCGAGCCCTGGGCGAGGAGGTGACCCGGGACCAGGCTGACCCCCAGTGC
-Y--S--R--L--R--A--L--G--E--E--V--T--R--D--Q--A--D--P--Q--C-

CTCTTCCTACGACAGCGACTGGAGGCCCTGGGAACTGGCTGGGAGGAGCTGGGCCGAATG
-L--F--L--R--Q--R--L--E--A--L--G--T--G--W--E--E--L--G--R--M-

TGGGAGAGCCGGCAAGGTCGCCTGGCCCAGGCCCACGGCTTCCAGGGATTCCTGCGGGAT
-W--E--S--R--Q--G--R--L--A--Q--A--H--G--F--Q--G--F--L--R--D-

GCTCGTCAGGCTGAGGGCGTGCTCAGCAGCCAGgtgaaagtccagggcaaagtcccaagc
-A--R--Q--A--E--G--V--L--S--S--Q- aggaggaagagcaaagtagggacccggggaaatgtgaaggagcaggatgggcaggaagga
                        rs11227574
catgctagcaaaatggggcagcgcagtggttcacacctgaaattccagcactttgggagg ccaaagtaggaggatcacttgaggctgagaatatccagaccaacctgggcaacatggcaa gaccttgtctctacaaaaaatttttttaagaaaatagaagaatttttttaaaaagaaaaa tgggagccagacaggatggctcacacttgtactcccagtattttgggaggccgaggcagg agaataacttgagctcaggagtttgagaccagcctgggcaacatagtgagacccccatct ctatgaaaaaaaaaattaactggacatggtggtgcatgcctgtagctccagctactggg gaggctgaggctggtggatcactggagccaggagtttgaggctgcagtgagctatgatat gccactgcactccaacctgggccacagaatgaaaccctctctcaaaaaaagaaaaagaa aaaagaaggaaaaatgagaatgaaaaagacgtgaatataatttactaaaactgactttag aagaaatagaaagcccagtttgtcatgtaactgttaaatggaatcaggagctagaagtga gatagaacaggatttgggctggggaatggaaggtccttcccacccagcttccctgtgact ttctgaggctcccatgctggctggcagcctccctgtcttcagagctctctgggctaccct ccctgtctgcttgttggtccctacctctcagatttgcccctgggtgggtccctcctaggg gggtgaattgtgctggggaaaatgagctgaatgtcatccctcccacacagGAATATGTT
                                                -E--Y--V-

CTGTCTCACACGGAGATGCCAGGGACACTCCAGGCTGCTGATGCTGCCATTAAAAAACTG
```

GAGGACTTCATGAGCACCATGGACGCCAATGGGGAACGGATCCACGGGCTCCTGGAGGCT
-E--D--F--M--S--T--M--D--A--N--G--E--R--I--H--G--L--L--E--A-

GGCCGCCAGCTGGTATCTGAAGGCAACATCCACGCCGACAAGATTCGGGAAAAGGCAGAC
-G--R--Q--L--V--S--E--G--N--I--H--A--D--K--I--R--E--K--A--D-

TCCATTGAGAGGAGgtctgatgaggacagtccatgaattagggttcccagggggggaatcg
-S--I--E--R--R gagaaacagggtgacctcaaagataaacgtggcacaggaaacccacagatggggcaggag ctgacagagaagtagaggggaagaactaagtggttggagagggctgggagattccacccc caaccagggctaaaaggaagtcaggattcctgggtagcctcattgtgctcccggaaggcg ttattcccctagaagaaatggaggcccctaggttagccaaagggtcacaatcctttcaca gcaaattccagagtttcacaagagggtgtcgttccagGCACAAGAAGAATCAAGACGCA
                                      --H--K--K--N--Q--D--A-

GCGCAGCAATTTCTGGGCCGTCTTCGGGACAACCGGGAGCAGCAGCATTTCCTGCAAGAT
-A--Q--Q--F--L--G--R--L--R--D--N--R--E--Q--Q--H--F--L--Q--D-

TGTCACGAGgtgaggctccctggggccccgggatattccctagccatccctttctcacct
-C--H--E- tgagcctagaataagtccagcacaaggtaccggagactgtgagccccttcatggcttctt cccaaggcgcccacttctcctggctcactgtggccctgcttttatgccccctctcccct cccttggaaatgtccctgttttatgtttggtccagCTGAAGCTCTGGATCGACGAGAAG
                                    -L--K--L--W--I--D--E--K-

ATGCTGACAGCCCAGGACGTGTCCTATGACGAGGCCCGCAACCTGCATACTAAGTGGCAG
-M--L--T--A--Q--D--V--S--Y--D--E--A--R--N--L--H--T--K--W--Q-

AAGCACCAGGCATTCATGGCCGAGCTGGCTGCCAACAAAGACTGGCTGGACAAGGTGGAC
-K--H--Q--A--F--M--A--E--L--A--A--N--K--D--W--L--D--K--V--D-

AAGgtgagcagtgctgtgggggctgcctctgggcagagtcccccatggtacgggggaggg
-K- cctggctccaggacgtggttttgtcatggttagagattgtggggttctggtgccacagc tccatggtggaaagttatggcctctgggaaacaaacgtctttgttggagacaaagagtgg gacagtgagtccagaaccttgataaagtacaaattagcaggtagcgaaactgcagcctgg atttaacgccataactgttcctgagttcaaagcaggatggtgctcttcagcaggctctgc
```

Fig. 6Q rs11823888
aaaccttgtctggaaagggcttgggctggatggtcaatatctgaggctttgcagtccaaa cagtttctactacaactactcatctctgtcgttgtagtgcaaaagcagcctcagagaata rs11227573
agtgaatgaatgaacatggctgtttcccaataaaactttatttgtaaaaacaggcagtgg gccagattaccccgtgggctgtatgtagtctgccaatccttattttcgagtcttgccgtc cctggttcttggtctcccacccagctgttcctcaagagtcaaggacagataaagctttat atctgctcagcaagtatccctacagaacatggtacgtgctcaacagtctgcgaggcactg cagggtctacgaaaagacactttccttttctcaagggcatgatggttgggacaaaaggag accagtgtgctttcaagtgtttccattcgttcagcaaatatttacttggtgctactatat ccaaagcattgtattaggccctgcgtggggtccgaaagggatcccatggtaggctccacc rs12419099
ctgaaggaacaacactgtagccaggatatgaggcatatatgcaggtagctaaatcgaatc cagagcagaatctgatgagtgctgtgagagtggccccgttgaagcctggggaataaggag agaggagatatggaaattctagaagcagcaacatccagggcagtccatggaggatgagta gaatttggacaagtggagatatggaggaaaagatgtttccaggtagagaaaaccaaacag aaaaccagtggtaggcagtgcctgtttgggagcaaggggggtgagtgagtccagcagcagc acagaatgtgtgcagggccccatggaagaagaggtgggagagaagccccgggaagtcctg accaccacatgcgtgtgcttccaagtgttgattgtgctcagggttgtgaagctacccagg cagtgctagcctttgatgctctccatcctgacagccacagccacctgcaaaatggcctga aggcagtgtctgggtttgtgttcccctagaagcagaccctgaaacagtgattctagggag gtgtccccgggaatgatcagtaggggggtggagccatgagaagggacagaagtcatgcca rs11825713
gttaccccatgggcatcaggagcccaaccctcatggggcattctgcgggggtgtagatg gaacacagaacacagcactctcacagccacggcacaaggatgctgtgtgtttatccatca gctccctgtctgtcactggttgagggctgcttctgggcttgttaactctgtggctcttcc aatttgccttccacacagttcaagagagcacacttccctcaccacccagacacagaaat cctcaagcagaaaagctggaagtggggaaaccaggtgggactcaacttgctatcactgaa gtgaagagtaatgagttgagaaatacaaaatgatggcaaataactcaagtcaatgtgcag tgtggtgccagaaaccacaggcaccaaggaacccaaactaaagagagtgcaagggcttcc tcgttgaaatgctgtttgagctgggtcttgaaggaggagtgggggttcatcagcagtgagg

Fig. 6R gaacagcagtttagaagggattttaaacctccgtgaagagtgtgtcgataagaacacaca aggacttggaattattgcccacacttcaggtctctactgcccgtaaggcccctggtctgc tctcagcctctaaagttcaggctaatttgggcactttgacattttctgtcctgccttcca

```
gGAAGGGCGAGAGCTCACCCTTGAGAAGCCAGAGCTGAAAGCCCTGGTGTCGGAGAAGCTG
 -E--G--R--E--L--T--L--E--K--P--E--L--K--A--L--V--S--E--K--L-

AGAGACCTGCACAGGCGCTGGGACGAGCTGGAGACCACCACCCAAGCCAAGGCCCGCAGC
 -R--D--L--H--R--R--W--D--E--L--E--T--T--T--Q--A--K--A--R--S-

CTCTTTGATGCCAACCGAGCTGAGCTGTTTGCCCAGAGCTGCTGTGCCCTGGAGAGCTGG
 -L--F--D--A--N--R--A--E--L--F--A--Q--S--C--C--A--L--E--S--W-

CTGGAGAGCCTGCAGGCCCAGCTGCACTCGGATGACTACGGCAAGGACCTCACCAGCGTC
 -L--E--S--L--Q--A--Q--L--H--S--D--D--Y--G--K--D--L--T--S--V-

AACATCCTGCTCAAGAAGCAGCAGgtgtgctgtgggcctttgatggggatggtgaacagc
 -N--I--L--L--K--K--Q--Q-
``` agaagaaaggggctgcagctttcaagatttgggaggccagctgaggcctggcagataaca ccttcactagcatttcccagagtcatttctttgggcagccagtatcagaatctctaggga tatgtcgcagtcagggttagagttaggagacagaccccctaataatttgacgatgagaac ttcagtaaaaagaaatattaattaggccaggcacagtggctcatgcctgtaatctcagca ctttgggaggccaaggcaggcaggtcgcttgaggtcaggagttcaagaccagcctggcca acatggtgaaaccccgtctctactaaaaatacaaaaattagccaggcgtggtggcgcacg cctgttatcccagctacttgggaggctgagggctgagggaggaggatagcttgaacccag gagacagaggttgcagtgagccgtgatcatgccatcgcactccagcctgggcaagcctct gtctcaaaaaaaaaaacagaagtataaattagtaaaaggtggtaaagagaactctatagc aggggtcagaaaacttttttcagtaaagcaccagatagtaaattttggggcttcatggg tcgtaaggtctatgtcacagcccttcaactctgcccttgtaaggaaaagcagctgcggat tatatgtaaaataaggggtatggccaggtgtggtggctcacacatgtaatcccaacactt tgggaggccgaggtggccggatcacttgagtccaggagttttgagactagcctgggcaac atggcaaaaccccatctctacaaaaactacaaaaattagctgggcgtggtggtggtgtgt gcctgtagtcccagctactcaggaggctgaggtgagaagattgtttgagcctggagagtc gaggctgcagtgggctgtgatcgtgccactgcactgcagcctgggtggcagagcgagact

Fig. 6S tgtctcaaaaaatttttaaaaaggggtgcagctgtggtccaataaaaactttataaggc taggcagtgggctggacttgctggtccctgctctgaagaatgcagaatgggaagtgtagg gagcagctgacacctctggggttgaggagtcccccaggaaggagcaagatggctgagtct cagacctccttggagagggcggaggcccactgaatggcctggaaatttgctggggtatca caggccagagcatgtctgaagccagcaagccaaggctggccagcaggaagtggccactag agtgcagcaaaacttgccagagagtaagagccaccggatctcttgcgcactgtggacagt tttgctgtaggaggaagaaaagcaccttggaaccgtggaatgccccacatctgctaggca ttgtggtgtccctccagcgccctctgctgacaaggcctagattgtgcctgctggcaaagg aggaatgtttccaggggccagttccagtgtctcaaagcagggccacgatggattggggat ggagagacaatgaattgataatgggcacagttatcacactaccctggatttttaatttc aatcttttagattcgcgggtgtgggtgcaggtttgttataagttatattgtgtgatgctg aagtttggggtgtaattgaacccatcacccatgtagtgagcacagtacccaatagggatt ttttcaacccctgcccttggattcttgtgcatataaagttcgagatccactgatccagcc catgagggatgctctccctgggtgagctgcagtgatgagcagccacagtgggctggata gagactggttggtgtctctgctgggcatgaaggcggaaatgcagagctaacatgtccttc ctcctggcggtttgcagATGCTGGAATGGGAGATGGCTGTGAGAGAGAAGGAGGTGGAG
      -M--L--E--W--E--M--A--V--R--E--K--E--V--E-
   rs471334
    Y
GCAATCCAGGCCCAGGCCAAAGCACTGGCCCAGGAGGACCAGGGTGCAGGGGAGGTGGAG
-A--I--Q--A--Q-=A=-K--A--L--A--Q--E--D--Q--G--A--G--E--V--E-

AGAACCTCGAGGGCCGTGGAGGAGAAGTTCAGGGCCTTGTGCCAGCCCATGCGGGAACGC
-R--T--S--R--A--V--E--E--K--F--R--A--L--C--Q--P--M--R--E--R-

TGCCGGCGCCTGCAGGCTTCTCGCGAGCAGCACCAGTTCCACCGCGATGTGGAAGATGAG
-C--R--R--L--Q--A--S--R--E--Q--H--Q--F--H--R--D--V--E--D--E-

ATTgtgagtcactggggccaaggacggcaagctgcccccagccatgtggttctccagcct
-I- ccctcctggatgccagggagatgccagcagggctctattccctcttctctttggcattga ccatctcccctatagggagacttggagatgcctcccagaaccagagatgactgttcccca cacacagggcggtagccccaggtgtccccactcccactaatcagtccctgctgcttgcct tgccctctgggcctccactgaccccctcttcctcttccagTTGTGGGTGACAGAGCGGCTG
                -L--W--V--T--E--R--L-

Fig. 6T

```
CCCATGGCCAGCTCCATGGAGCATGGCAAGGACCTGCCCAGCGTCCAGCTTCTCATGAAG
-P--M--A--S--S--M--E--H--G--K--D--L--P--S--V--Q--L--L--M--K-

AAAAACCAGgtgaggcagaggctgaaggcaaaagagaagttcccaggagcctgcccagac
-K--N--Q- ttggacgtgttttttcttaagaccaggccccctcgatgctgagtgtaaccctggacttc agtggctgtctttcctcaccttgggagggtgggtcctctcagtaggagatagtgggggct gggcggctgacgggtgttaccatcgcacccccaggctaggagagggagcagaggacccag gaaggagagaggcacaggggtgaagggtggtctccgggagcacgtggggctggggcagga ctttcagcattttctcttctgtggccatgggcag ACCCTGCAGAAAGAGATTCAGGGCCATGAGCCCCGGATCGCGGACCTGAGGGAGCGGCAG
-T--L--Q--K--E--I--Q--G--H--E--P--R--I--A--D--L--R--E--R--Q-

CGTGCTCTAGGTGCAGCAGCAGCAGGTCCAGAGCTGGCTGAGCTGCAGGAAATGTGGAAA
-R--A--L--G--A--A--A--A--G--P--E--L--A--E--L--Q--E--M--W--K-

CGCCTGGGCCACGAGCTGGAACTTCGAGGGAAGCGACTGGAGGATGCCCTGCGAGCCCAG
-R--L--G--H--E--L--E--L--R--G--K--R--L--E--D--A--L--R--A--Q-

CAGTTCTACCGCGATGCCGCCGAGGCGGAGGCCTGGATGGGCGAGCAGGAATTACACATG
-Q--F--Y--R--D--A--A--E--A--E--A--W--M--G--E--Q--E--L--H--M-

ATGGGCCAGGAGAAGGCCAAGgtgagggccaggacagagcccagtgtatgtgaccagttc
-M--G--Q--E--K--A--K- tgccctccctgacctgatgctggatgccactgtcccttcccccagGATGAGCTGAGTGCC
                                              -D--E--L--S--A-
                      rs639938
                          R
CAGGCAGAGGTGAAGAAGCACCAGGTGCTGGAGCAAGCCCTGGCCGACTACGCGCAGACC
-Q--A--E--V--K--K--H--Q--V--L--E--Q--A--L--A--D--Y--A--Q--T-

ATCCACCAGCTGGCGGCCAGCAGCCAGGACATGATTGACCACGAGCACCCAGAGAGgtgg
-I--H--Q--L--A--A--S--S--Q--D--M--I--D--H--E--H--P--E--S rs11227572
gtgcagcggcagcccggcccagcctgggggtggagccggctgcaggaacaggaaggtgca gggaatgtggagccttcagtgctgtgtgcacggagccttctagaaagctggaacacaggg tgggcgagctgttgggagactcagagggacagggctccacagaacagaccggaggtcaga gctacaccccctaagtcccacagtgcctccctcactcttcttgcagCACTCGGATATCCATC
                                               --T--R--I--S--I-
```

Fig. 6U

```
CGCCAAGCCCAGGTGGACAAGCTGTATGCCGGCCTGAAGGAGCTGGCTGGAGAGCGGCGG
 -R--Q--A--Q--V--D--K--L--Y--A--G--L--K--E--L--A--G--E--R--R-

GAGCGCCTGCAGGAGCACCTCCGGCTGTGCCAGCTCCGCCGCGAGCTGGATGACCTGGAA
 -E--R--L--Q--E--H--L--R--L--C--Q--L--R--R--E--L--D--D--L--E-

CAGTGGATCCAGGAGCGCGAGGTGGTGGCGGCCTCCCACGAGCTGGGCCAGGACTACGAG
 -Q--W--I--Q--E--R--E--V--V--A--A--S--H--E--L--G--Q--D--Y--E-

CATGTGACTgtgagtgtagggagggcacccagctcagatcaaccgtgggaagagtggagg
 -H--V--T- acccacagggagactaggacctagtcccaggcagagcactgaggggctaaggggcaagac caggctgagcaggcactgtcctcctggttttgaggtatatgatttgaagaggccgggcat aggctcacacctgtaatcctagcaccttgggaggctgagatgggaggattgcttgagtcc aggagttcaagaccagcctgggcaacatagtgagaccccccatctctacaaaaaaattt tttttattagccaggcacagccgtgcatgcctgtaggcccaactacttaggaggctgag gtgggaggatctcttgagcctgggaggtcgacactgcagtgattgcgctagtgcactcca gagcaagaccctatcatctctaaatacatacacacacacaatttgaagaattgtacag aaaggggacatgaagctgagctgagacaagggcaaacaggaaattatcactcacactttt caacagaattcaacaaaacggagtatgatccaccccccgacagtttggggcttggacc ctcagtcgtacagaaatatggaccatagttagggtatccttgtctgaagcctaagggtcc caagcaccttgaaacgcctttgctgggggtggagggagtctgtcaaatacagggtcagtg ggaagcagctgcacctactccttaaccacagggaagaaacctgtcccggcccccatgcag cggggagaggtgggttctgagtttggagtggaggactcgctccatcaggcagggaccaca tcccctaacatcacggcatggtctgtccatctgcttcctctaccagATGCTCCGAGACAAA
                                               -M--L--R--D--K-

TTCCGAGAGTTCTCCCGGGACACAAGCACCATCGGTCAGGAGCGCGTAGATAGCGCCAAT
 -F--R--E--F--S--R--D--T--S--T--I--G--Q--E--R--V--D--S--A--N-

GCGCTGGCCAATGGGCTCATTGCTGGGGGCCATGCTGCACGGGCCACCGTGGCCGAGTGG
 -A--L--A--N--G--L--I--A--G--G--H--A--A--R--A--T--V--A--E--W-
               rs623022
                  Y
AAGGACAGTCTCAAĢGAGGCCTGGGCTGACCTGCTTGAGCTGCTGGACACACGGGGTCAG
 -K--D--S--L--N--E--A--W--A--D--L--E--L--L--D--T--R--G--Q-

GTGCTGGCCGCGGCGTACGAGCTGCAGCGCTTCCTGCACGGGGCACGCCAAGCCCTGGCG
```

CGGGTGCAGCACAAGCAGCAGCAGCTTCCGGACGGGACTGGCCGCGACCTCAACGCTGCC
-R--V--Q--H--K--Q--Q--Q--L--P--D--G--T--G--R--D--L--N--A--A-

GAGGCCCTGCAGCGCCGACACTGTGCCTACGAGCATGACATTCAGGCCCTCAGCCCCCAG
-E--A--L--Q--R--R--H--C--A--Y--E--H--D--I--Q--A--L--S--P--Q-
                                                                rs12804382
gtctgacccaagcatgaggaggtgggggaggcttagaggaggccatgggggaaatgccgg ggagagttcccaggagctagggtagagctcagaaatgctgggaggacggcactctttcga gggccatttcgagatgaggaaattgctccaagaaaacatctctgtttggccaggcgcggt ggctctcgcctgtaatcccagcactttgggaggccgaggagggcggatcatctgagattg ggagttcgagaccagcctgaccaacatggagaaaccccttctctactaaaaatacaaaat tagccaggcatggtggcgcatgcctgtaatcctagctactcaggaggctgaggcaggaga atcacttgaacccaggaggcggaggttgcagtgagctgagatccctccactgcactccag cctgggcaacaagagcgaaactccgtctcaaaagaaagaaaacatctctggcaggggac atctagccactgcattcacacttttgatgacaagccccttgagagcccatgatgtcttc aggggttcccagtggccaggagactcttcatgctgcgctaaatcagcctgttagtgcttc ccaggcttgagctctaggctcacactcagtaagcatggatccttccttcaaccactagaa cccatcagcccctgcctgaatccccttttcaggctaagtagcacgttctagcaatctcca aggtctatacatcctagacaggcctctgaaagttcaactggccaatggctcttttccag atcctcccccagttaagcccaggtgtctagatgagacccaacagggcagagtgtggccag cccctgccttcatctttcccagcaccccactccctggctcctcccccctgcttcttttggt gtgagacaggcaggaggtgagagtggcagccaggactgaggcaggctgcggctccttgga gtcccccgctctgcctgactctgacccggggctccgcagGTCCAGCAGGTGCAGGACGAC
                                         -V--Q--Q--V--Q--D--D-

GGCCACCGGCTCCAGAAGGCCTACGCTGGAGACAAGGCTGAGGAGATCGGCCGCCACATG
-G--H--R--L--Q--K--A--Y--A--G--D--K--A--E--E--I--G--R--H--M-

CAGGCCGTGGCCGAGGCCTGGGCCCAGCTTCAGGGAAGCTCTGCCGCCCGCCGGCAGCTG
-Q--A--V--A--E--A--W--A--Q--L--Q--G--S--S--A--A--R--R--Q--L-

CTGCTGGACACCACAGACAAGTTCCGCTTCTTCAAGGCTGTCCGGGAACTGATGCTCTGG
-L--L--D--T--T--D--K--F--R--F--F--K--A--V--R--E--L--M--L--W-
```

Fig. 6W

```
ATGGATGAGGTCAACCTGCAGATGGATGCCCAGGAGCGTCCCCGgtgagaatcccagggc
 -M--D--E--V--N--L--Q--M--D--A--Q--E--R--P--R tcagggcctccacggggttgtgtggctgggctgtgatggggctgtgggcagcaggtgatgc tgtttctgcctccccccagGGATGTGTCCTCCGCGGATCTAGTCATCAAGAACCAGCAA
                    --D--V--S--S--A--D--L--V--I--K--N--Q--Q-

GGCATCAAGGCAGAGATAGAGGCCCGGGCAGACCGCTTCTCCTCCTGCATCGACATGGGG
-G--I--K--A--E--I--E--A--R--A--D--R--F--S--S--C--I--D--M--G-

AAGGAGCTGCTGGCCAGGAGCCACTATGCGGCCGAGGAGgtgggtgaggcctgggtggcc
-K--E--L--L--A--R--S--H--Y--A--A--E--E- gggccattctcactgtgcagtgctgaacgctgacttcttggtggctttctgcttcctctc attctctctttgcaagaaaccctttcattctctcccctcagtgccattcacgggtttctcg cattctggaaatctctccccagaaccgtctgcctcttgacatcagaaatcactggtcctg ggccaggcatggtggctcacgcctgtaatcccagcactttgggaggcccaggcgggcaga tcacctgaggtcacgagttcgagaccagcctggcctccatgggttgtgtggctgggctgt
                 rs508996
gatgaaacatggtgaaacccc gtttccactaaaaacacaaaaattagccgggcgtggtgg cgggcacctgtaatcccagctactcggaggctgaggcaggagaattgcttgaacctggga ggtggaggttgcagtgagctgagattgcgccactgcattccagccttggtgataagagcg aaactccgtctcaaaaaaagaaagaaagaaagaaatcacctgtcccctggatgactcc ccaggggccgtggaaagatctcacatcctggtgctaactcatatctctgcccccgcccc cagATCTCAGAGAAGCTGTCTCAGCTGCAGGCACGGCGCCAGGAGACAGCTGAGAAGTGG
   -I--S--E--K--L--S--Q--L--Q--A--R--R--Q--E--T--A--E--K--W-

CAGGAGAAGATGGACTGGCTTCAGCTGGgtgagctgccaaggggggccccaggccctgtgg
-Q--E--K--M--D--W--L--Q--L-- ggagtgggggggcatcctgcaccctgtgggttccagagtaggtgagactaggaaccctggg tgtgaaactcacgatgcccaatcttcgtgctgcctggcacagctctggggcagtggcttt
                 rs2276138
ctctgtgtccctgttcttgaggttgcc atggccactgtgccctgccagtggccactctga
                 rs2276137
cccaccatcttcctgcaacccc cgatcctgccagTTTTGGAGGTGCTTGTGTTTGGAAGA
                                    V--L--E--V--L--V--F--G--R-

GATGCAGGGATGGCAGAGGCCTGGCTCTGCAGCCAGGAGCCACTGGTGCGCAGCGCTGAG
-D--A--G--M--A--E--A--W--L--C--S--Q--E--P--L--V--R--S--A--E-
```

Fig. 6X

```
CTGGGTTGCACGGTCGACGAAGTTGAGAGCCTCATCAAGCGGCACGAGGCCTTCCAGAAG
-L--G--C--T--V--D--E--V--E--S--L--I--K--R--H--E--A--F--Q--K-

TCAGCAGTGGCCTGGGAGGAGCGATTCTGTGCGCTGGAGAAGCTTACTGCGgtgagggac
-S--A--V--A--W--E--E--R--F--C--A--L--E--K--L--T--A-
                                                              rs2276136
acaggaccccggatgcccactccaacctgctcccctgacctgtgctggcttctgcttgga gaagacatgtcttctctcttcccactgcaccagtggcccccagatgtgagctgagagtgc cattgtcaccacacctttaggaggtgtcagttcccctgggtgatgccgagacaccttctc ccgctttgtttcttgtccccaccatcttctcaaattctgttctcctcttatcatatttca tcaaattagagttgagacatttcagctctccctgtttccctggccctcttacacgcaacc ttctacacgctgaatgcagcattttttgacagCTAGAGGAGCGGGAGAAGGAGCGAAAG
                                -L--E--E--R--E--K--E--R--K-

AGAAAGAGGGAGGAGGAGGAGCGGCGGAAACAGCCGCCTGCTCCCGAACCCACAGCCAGT
-R--K--R--E--E--E--R--R--K--Q--P--P--A--P--E--P--T--A--S-

GTGCCTCCAGGGGACCTGGTGGGCGGCCAGACAGCTTCTGACACCACCTGGGACGGgtga
-V--P--P--G--D--L--V--G--G--Q--T--A--S--D--T--T--W--D--G gagccaggatgcctgggtaggaggaggcggctgagcccaggccacccagggactaatgat tctgtgttgcctttggtcatcccagAACCCAGCCACGGCCACCACCATCCACACAAGCA
                          --T--Q--P--R--P--P--P--S--T--Q--A-

CCCAGTGTTAATGGAGTCTGCACAGATGGAGAGCCCTCACAGgtgacccactgtccctc
-P--S--V--N--G--V--C--T--D--G--E--P--S--Q- tgtgccccatcggagtcgtagcccctccaccccgcacatccttttacagattcttgtc cttgcagCCCCTGCTGGGACAACAGAGACTTGAGCACAGCAGCTTCCCCGAAGGGCCGgt
       -P--L--L--G--Q--Q--R--L--E--H--S--S--F--P--E--G--P- gagttcccctgcaagtgtggtgttgataactgtgaggcgaagggtccagagggggtggtg agtgcgggtgggggagtactggggatgggatgggagagggcagaggctcacaggcagctt gggggcaggaagaccaactcctggacacggagcttcctggcacccaggttagggatctcc cgtctcaaacctttgacactgacactgattccccccagGGACCTGGCTCAGGGGACGAA
                                       -G--P--G--S--G--D--E-

GCCAATGGGCCCCGGGGAGAGAGGCAGACCCGGACTCGGGGCCCGGCCCCATCTGCAATG
-A--N--G--P--R--G--E--R--Q--T--R--T--R--G--P--A--P--S--A--M-
```

Fig. 6Y

```
CCCCAGAGCAGGTCTACCGAGTCAGCCCATGCTGCCACCCTGCCGCCTCGAGGCCCAGAG
-P--Q--S--R--S--T--E--S--A--H--A--A--T--L--P--P--R--G--P--E-

CCATCTGCCCAGGAGCAGATGGAGGGGATGCTGTGCCGCAAGCAGGAGATGGAGGCCTTC
-P--S--A--Q--E--Q--M--E--G--M--L--C--R--K--Q--E--M--E--A--F-

GGGAAGAAGGCTGCCAACAGgtacagcctctctggagcctgctctcagagggcacttccc
-G--K--K--A--A--N--R cagagcctctgcccagatagagggagggatgcccttagagtacatcttctgggcaaagg gtaggacttgggaccagagcggggcctcaggggaggaccagagggtgtgaagaccgtggc ctaaagatgggagcagaactggaagtcctaggacacccaagagggctccaggttgcgggc gccactgaggccggccagtcagcaccgcgtccctcgcagGTCCTGGCAGAACGTGTACTGT
                                        --S--W--Q--N--V--Y--C-

GTCCTGCGGCGTGGGAGCCTCGGCTTTTACAAGGATGCCAAGGCAGCCAGCGCGGGAGTG
-V--L--R--R--G--S--L--G--F--Y--K--D--A--K--A--A--S--A--G--V-

CCATACCACGGAGAAGTGCCTGTCAGCCTGGCCAGGGCCCAGGGCAGCGTCGCCTTTGAT
-P--Y--H--G--E--V--P--V--S--L--A--R--A--Q--G--S--V--A--F--D-

TACCGAAAGCGCAAACATGTCTTCAAGCTGGGgtaggaacagggaacagtgctctcggga
-Y--R--K--R--K--H--V--F--K--L--G tgggaggagagttgggagtgacacaggtgagccatgagtcaggtccagagggaggggagt tcctgtaaggagcctgagtggagtaaccaggccagccacttggggatagtgtagatgagg gaggcggagattctggttgtctccacaccaaggggagcaggagaaccaagacccaggcct gacggctgccaatgtcaaggtgaaaaattacccagggtgggaaatccaaaggtagggatc tgggaagacctccaggggcctgtccctgcctgccagcaagcagccggagcaggaggcccg ggctggggtggaagtgagctcccctgcctctggggccagtcagaaaggatgtgcttctg cacagtctggggaagctgaagaatgtgcagagcgtgtctggtccggctctgagggctgca gccagatgtcccagcctggtgttgggtcatgattacgctctcaccagcagctacctggca gatccggattctcagctctgccctgtggcctctctctcccaacagCTTACAGGATGGAAAA
                                              --L--Q--D--G--K-

GAATATTTATTCCAGGCCAAGGATGAGgtgagctgtccttcgtgttcctctctgtccgtg
-E--Y--L--F--Q--A--K--D--E- ccattccagaagcttccagctgcagactccccttctttccctgtcctccctctttttcct ggtcttgtcctttgtggtaagactggatgtgtgcgacggccgcaccaggccgcactccct
```

Fig. 6Z

```
gtctaagccggccacattctcctaatagcatgaaacagtcagctcactttctgcctcctc ctcttacacttccctgctgtccactgcggccaactcagcacagtgtccttgaagctgatt gagggtctttccatccacagGCAGAGATGAGCTCGTGGCTACGGGTGGTGAATGCAGCC
                    -A--E--M--S--S--W--L--R--V--V--N--A--A-

ATTGCCACAGCGTCTTCTGCCTCTGGAGAGCCTGAAGAGCCGGTGGTGCCCAGCACCACC
-I--A--T--A--S--S--A--S--G--E--P--E--E--P--V--V--P--S--T--T-

CGGGGCATGACCCGGGCCATGACCATGCCCCCAGTGTCACCCGTCGGGGCTGAGGGGCCT
-R--G--M--T--R--A--M--T--M--P--P--V--S--P--V--G--A--E--G--P-

GTTGTGCTCCGCAGCAAAGACGGCAGAGAACGAGAGCGAGAAAAACGCTTCAGCTTCTTT
-V--V--L--R--S--K--D--G--R--E--R--E--R--E--K--R--F--S--F--F-

AAGAAGAACAAGTAGTTGGGGGCAAGGTCCCCAGGCCAACTCCCTCCCTCCGTTCAGGAAA
-K--K--N--K--*-.............................................

CTGCCAGGGACAGTCGACAGGGACCGCCCTCTTGTCAGGACAACTGCCTGCTGCTAGGGT
............................................................

CTGTTGCCAAGGTCAACCCATCACCAGGAACTGTCACTGGGGACGAGTCCATGTTCCCAA
............................................................
rs693564
       R
GGSCAGCCCTTCTCTTCTGCTGTTTAATTCCAGACTGGTGGTGGGACCCAGGTAACCCCC
............................................................

TCTCCCACCCCCGCCGACTTCTCCCCTTTCCCCAGCCTCGTGCCTCTGTCCCTCACCACG
............................................................

GTGTGGACAGTGCCGCACCCTCAACATAGGCCATGTGGGGAGTGGCTGCCCCTGCCTCAG
............................................................
             rs11828658
                    Y
GGTCATTCTCCTGCCATGSGAGGGCACTCGCCTTCTGCCTTCTGGTTCCTCACCCCTCAG
............................................................

ACCAGCCAGGAACCTCTCAGAGCTGAAGCAGGCCCTGGGGGCAGAAGTGCCAGATGACAG
............................................................

TCAGAGGCGCAGGAGCCCTCCCTCCCCACCCCCACCCTGTAACTCCAGCTGCCACTCCAT
............................................................
   rs1064352                    rs12575562
       Y                            Y
CTCCAGSTGCTCTCAATGGCTTCCAGGTGTGTTGTSCGGGGACAGCCACCGCCTTGAGTC
............................................................
```

Fig. 6AA

TGGCCAAGGAGGTGATTAAACAGCTCAGCTTCTC

SEQUENCE LISTING

```
<160> NUMBER OF SEQ ID NOS: 77

<210> SEQ ID NO 1
<211> LENGTH: 36147
<212> TYPE: DNA
<213> ORGANISM: Homo sapiens
<220> FEATURE:
<221> NAME/KEY: CDS
<222> LOCATION: (160)..(316)
<220> FEATURE:
<221> NAME/KEY: CDS
<222> LOCATION: (5419)..(5570)
<220> FEATURE:
<221> NAME/KEY: CDS
<222> LOCATION: (6005)..(6178)
<220> FEATURE:
<221> NAME/KEY: CDS
<222> LOCATION: (6993)..(7084)
<220> FEATURE:
<221> NAME/KEY: CDS
<222> LOCATION: (7229)..(7309)
<220> FEATURE:
<221> NAME/KEY: CDS
<222> LOCATION: (7654)..(7769)
<220> FEATURE:
<221> NAME/KEY: CDS
<222> LOCATION: (10371)..(10483)
<220> FEATURE:
<221> NAME/KEY: CDS
<222> LOCATION: (10631)..(10818)
<220> FEATURE:
<221> NAME/KEY: CDS
<222> LOCATION: (12381)..(12498)
<220> FEATURE:
<221> NAME/KEY: CDS
<222> LOCATION: (13101)..(13259)
<220> FEATURE:
<221> NAME/KEY: CDS
<222> LOCATION: (13582)..(13884)
<220> FEATURE:
<221> NAME/KEY: CDS
<222> LOCATION: (15563)..(15716)
<220> FEATURE:
<221> NAME/KEY: CDS
<222> LOCATION: (15932)..(16802)
<220> FEATURE:
<221> NAME/KEY: CDS
<222> LOCATION: (19679)..(19816)
<220> FEATURE:
<221> NAME/KEY: CDS
<222> LOCATION: (20118)..(20874)
<220> FEATURE:
<221> NAME/KEY: CDS
<222> LOCATION: (21792)..(21994)
```

```
<220> FEATURE:
<221> NAME/KEY: CDS
<222> LOCATION: (22318)..(22408)
<220> FEATURE:
<221> NAME/KEY: CDS
<222> LOCATION: (22615)..(22761)
<220> FEATURE:
<221> NAME/KEY: CDS
<222> LOCATION: (24860)..(25123)
<220> FEATURE:
<221> NAME/KEY: CDS
<222> LOCATION: (27037)..(27261)
<220> FEATURE:
<221> NAME/KEY: CDS
<222> LOCATION: (27539)..(27628)
<220> FEATURE:
<221> NAME/KEY: CDS
<222> LOCATION: (27954)..(28214)
<220> FEATURE:
<221> NAME/KEY: CDS
<222> LOCATION: (28300)..(28430)
<220> FEATURE:
<221> NAME/KEY: CDS
<222> LOCATION: (28660)..(28864)
<220> FEATURE:
<221> NAME/KEY: CDS
<222> LOCATION: (29742)..(30116)
<220> FEATURE:
<221> NAME/KEY: CDS
<222> LOCATION: (31116)..(31360)
<220> FEATURE:
<221> NAME/KEY: CDS
<222> LOCATION: (31456)..(31594)
<220> FEATURE:
<221> NAME/KEY: CDS
<222> LOCATION: (32219)..(32303)
<220> FEATURE:
<221> NAME/KEY: CDS
<222> LOCATION: (32550)..(32746)
<220> FEATURE:
<221> NAME/KEY: CDS
<222> LOCATION: (33088)..(33230)
<220> FEATURE:
<221> NAME/KEY: CDS
<222> LOCATION: (33320)..(33395)
<220> FEATURE:
<221> NAME/KEY: CDS
<222> LOCATION: (33481)..(33531)
<220> FEATURE:
<221> NAME/KEY: CDS
<222> LOCATION: (33752)..(33972)
<220> FEATURE:
<221> NAME/KEY: CDS
<222> LOCATION: (34232)..(34405)
<220> FEATURE:
<221> NAME/KEY: CDS
<222> LOCATION: (34959)..(35001)
<220> FEATURE:
<221> NAME/KEY: CDS
<222> LOCATION: (35295)..(35525)

<400> SEQUENCE: 1
ccactgagca gccaaccgca gcctctggcc acaaggagag cggagcacag gtagggcaag       60
aagacagaag gccccggtgg tgagtggagg gcttggtggt ccctggacac ccctcactgg      120
ccacattctc cttgcaggag caggaagccg cctaccacc atg agc agc acg ctg         174
                                             Met Ser Ser Thr Leu
                                              1               5 tca ccc aca gac ttt gac agc ttg gaa atc cag ggc cag tac agt gac        222
Ser Pro Thr Asp Phe Asp Ser Leu Glu Ile Gln Gly Gln Tyr Ser Asp
             10                  15                  20 atc aac aac cgc tgg gac ctt cct gac tcg gac tgg gac aat gac agc        270
Ile Asn Asn Arg Trp Asp Leu Pro Asp Ser Asp Trp Asp Asn Asp Ser
         25                  30                  35
```

| | |
|---|---|
| agc tcg gcc cgc ctc ttt gag agg tct cgc att aag gct ctg gca g<br>Ser Ser Ala Arg Leu Phe Glu Arg Ser Arg Ile Lys Ala Leu Ala<br>40                            45                      50 | 316 |
| gtgaggtcag aggagggtcg aggtgggggg atgctggagg aggctttgtc agctcgtcat | 376 |
| gaagagccct ttaactttat gggaagactg acttttcttt ctaagtggga gacccagagc | 436 |
| actctatcaa ttccctggtc cccacatcca gcctcaagaa taggctccag gccattcaga | 496 |
| actttcccca gctcttcccc ccaagcatag agacgcttca ctggcccctg gactggctga | 556 |
| gctgactaaa acagcttccc tctctggcct cagcccccgg gtcatgtccc ttcatccttc | 616 |
| ggcactctcg ctcttgccac tcctttctcc gcctacctct cccttacctg tcatgccctt | 676 |
| gttgtgtctt ctttgatttc cactgtcatt tcccacacct gttcccagtc tattattccc | 736 |
| ctctgctccc tctccacctg ttccttccac ctgccacctg ttactcccat tatctcatct | 796 |
| gcctgttccc tgaagcaggt tccctccacc cgctgctgct ggtttctgca gccgcccatt | 856 |
| ctccctggtg tgctctctgc ctgccttggc tcctactctt ccctgcagcc cagggcctgg | 916 |
| gctctccgct ctgagcggaa actcgtccaa cggcctccct gtcttccggg ggaggagttg | 976 |
| tcatggcaac aagagtgcgg ctgccacctg acaccaccag tggctggcat ggggctgact | 1036 |
| cacccacaca ccccaaggcc acctaccccg tctggcttcc tcctccatcc cactcttgtc | 1096 |
| attgccattg acctgctggc tgcccagccc agcccaaccc aacccagtct gaggggtccc | 1156 |
| agctactctc accgagaggt ggtgctccga gtgggggtgg gggttggcca ctagaagaag | 1216 |
| agagactcca aggggaggt tcccaaacct ggccacatgt tttacaggat cacccaggga | 1276 |
| tgttttttac aaatacaggt ttccaagccc ctccctagac acaataagtt agaatcttgg | 1336 |
| tccagaactc aggattttc aaaagctccc caagtgattc ttttgagcca gctcagcacc | 1396 |
| agtctgagga ccccttgtg gcagccatag cttcccagga ccccttctca ttttctcctg | 1456 |
| ggcctctctg tccttctggt tgggtcttca ggccggctgt gaaacactcc taccagtgtg | 1516 |
| tctatacatc agagaagaca gaaggtgtgg gttatggaga atgtcatgtt tggggaaaat | 1576 |
| gttcctggca ctctggtttt ggattcatgt agcctctaga actgtcatga tgtctatgtg | 1636 |
| tgtacaacat gtgccaccca ccatgtttgc acacatgaca aatgccatcc aggactgtca | 1696 |
| ccaygcctgt gtacatagga cacatgcctc ccaggactct caccatgcct gtgtacatag | 1756 |
| gacacatgcc acccaggact gtcaccatgt ctggctgcac ataacttggg ccacccagca | 1816 |
| ctgtcaccat gtctgtgcac acatctgtgt gacctcgtgc tctcattggg tgtttatctc | 1876 |
| caccactgaa ctgggctctc ctgaagaggc agctctgcat gggatttgcc tagcactgtg | 1936 |
| tctccagcca gtaggtgtca aataaacact gaatgaatga agatgaggaa gggcaagtgt | 1996 |
| aggctgcaca tgacaaacgc tgaagcccag aggaagggcg cctggtatat gtgcccagca | 2056 |
| gcggggcgtc tgggggcagg gatggcctgg tgaggatgg ccctggtggg ccagagggca | 2116 |
| gggaaggggc tggcactgga ggtggtgata agcaagtgga aaggatggta acagccctcg | 2176 |
| tttcacagat gagggagtga aggaaaatgc ctcgcacagt gcctggcttt tcctctttga | 2236 |
| ggatttcctc gtttccagat ttctctttgt ctgtttctga gctggggctc aaagccaca | 2296 |
| catcctggag aaggacctcc cagagtcacc cagagagggg tcgccctcgc tgttcctgca | 2356 |
| aacctctggg aaacaggagt ttgcattggg ggccctctc gtgggtcctg tgcattgtta | 2416 |
| ggtaacttgg ggcctgatgg gcgggtcttg aaggcgctgg cagtgccctc ctccgccgcc | 2476 |
| ccgcagggcc tggccctgcc ccgccggcc acactccgcc tctctccct ccccaacact | 2536 |
| gtccaacctg tttgtctgga gccgcctgtc tcctctcacc gcagccaggc gtgcccccac | 2596 |

```
tctctgtctc aggagttcgg gacaccccgt aactcttttt gccactcctt gaaattccca    2656
ccattcttga atccctgac gctggactcc agcctgaggt tccactgggg aacagaaact     2716 ggcccctgc crgcggggag catgactct gggccctggg ctctgtaact agcagctggc      2776
agcatgaatg ggaacggagt gagsagggtg cacgggaacg gcctgcatga ggccagcgag    2836
ttttactatg aggctgtgga aggggcccac aaccccgggg gcctcctgct ttcaccagct    2896
gctttcatca accctgctca gtatgccagc gtgctggaag gacgcttcaa acagctgcaa    2956
ggtgaggccc gggggccccc tgtggggacg actgtgcctg ggcgagaggg acctgggtgt    3016
ggggagagtg gccggagctg aggacctggc acaggacaca gtgtgactcc agtgtttgtg    3076
ttgggagaca acgtgatgca gcttagaggg gataattaca agaggccgga aaatayacag    3136
atgtcaacgg aatggggaaa ggcttggacc tgctggcagg gaccgtgtat gatggcatgg    3196
gtgggtgtga ctgccggcc ttggggtgct gcatggagca aaggcaacta gccatggagg     3256 gcgtggggt gccagcacct ggggaggcgc cagcagtgcc tctgaggtgg atccggatct     3316
ggcggtggag cgctgccag gacagttagg ggaggcggag gggtgagcca ggcccaggga     3376
cctggagatt gtgttttcca ggcctctgag cgtgtgtctg aatgtgtaca cggggcagt    3436 gtgtgtggaa gcaaagggag tgtctcgaag gagaggatct gtgcaaacag gcccaggtag    3496
atgtctgcgc aggtgtgtgt tcactctggc acaagtgctt aggtgtgttt ttgggaatca    3556
ctgttgtgtg tgtgtgtgta aggatctagg gatgctgtgg gcgtcttgtg acgtgacact    3616
tggtttctgg tgcttggctt tgcccatttt cctcctagtt gccactaatt ctgtgtcttc    3676
tgactgtgtg ccaaaatggc ctcacccag ggtgcccagc agtagggcag tgccctgga     3736 tccagcaatg gcctgtgacc cacgctcctc ctggctcaga tggggcctgt agacctgccg    3796
ggaggcccca aggcaccttg gtttcatggg tgctggggag catggggccg tccatgtta    3856 ttaggacccc aggtttggtg ccagtatagt ggctggaggt gaaagacacg gagcgacgtg    3916
ggtgtgttgc tgtgtcttat gggtgaggtg cttaggaatg tgagattaag ggatgagtct    3976
ttccggtttc tgasatgctg gtgctgagac ggaagcaaaa gtgactcttc agaccccagc    4036
cacttgggtt gggtccttgc acagggctct ctgtgggaaa gtggcagaaa tcctcatcac    4096
cagagcagtt tctgatgctt tcactttgtc acttagaacg ttcttaattt ttattttcct    4156
acggaaccta gtatttactt cccctcttca gtagctcccc tcccctgtgg gctgggcagc    4216
agggcattgc ctaactttt tttgagattg gtacctaact ctgcctggct ttttttcccc    4276
catgtttcct ggcctcactg ttttcccagt tcccaactct caacatcttg ttcttctaag    4336
caatggggtg tttatgtcct ggaactggat cccttgcag ccagctgaat gtactgtccc     4396 caaccccag aagcagagga gcctgccttt tctttaagtt atccaaggac agtaagctga     4456
ctcaggaggc ctgcagcctc tataccatca gtcctaatg accgcttgga agagccgctg     4516
caataatttt agcccacacc ttctcctttg tctgcaacca aaagagaaca gccatacctc    4576
ccaccggcct gggcagctct tgctctcctt cgggccagat cacaccactt tataacagca    4636
gctcaccaag gagccatttt gtgccaggca ccaactagtt gttttatata ccttatctca    4696
tttaatcaac acaatgacct gttgaagtag aaagtgatgt tcccatttta cagatgagac    4756
attggggctc tgatgaatga agtcacttga ccagcattcc actgcttcca cgactgcccc    4816
atcccagccc ctccctgcat gtcccatggt ttctgaggat gaaaggtctt catcctttct    4876
tctcaaagcc tattttcttt tytttctctt tctttttttt tttgagacg gagtcttgct    4936
```

-continued

```
ctgtcgccca ggctggagtg cagtggcaca atctcggctc cctgcaagct cccctccca    4996 ggttcacgtc agtctgcctc agcctcccga gtagctggga ctacaggcgc cgccactat    5056 gcccggctaa tttttkgtaa ttttagtaga cgggtttt caccgtgtta gccaggatgg     5116
tctcgatctc ctgaccttgt gatccgcccg ccttggcttc ccaaagtgct gggattacag   5176
gcatgagcca ccacacccaa ccttcgccta ttttctgtct ttcatctttc ttctttacct   5236
tgcttatgag ctcattgcaa gttacgggcy ttcctcccgg tcatcttcct tcccttcctc   5296
ctccttagag gaccccgctt cccatctctc aggcttctcc atcccccacc cctgccaact   5356
ggtgtttaga agcaggcata ctgaactcga gggacagaaa taaacccatg ttgccaccac   5416
```

| | | | |
|---|---|---|---|
| ag at gaa cga gaa gct gtg cag aag aaa acc ttc acc aag tgg gta | | | 5462 |
| Asp Glu Arg Glu Ala Val Gln Lys Lys Thr Phe Thr Lys Trp Val | | | |
| 55 60 65 | | | |
| | | | |
| aac tcg cac ctg gcc cgg gtc acg tgc cgg gtg ggg gac ctg tac agc | | | 5510 |
| Asn Ser His Leu Ala Arg Val Thr Cys Arg Val Gly Asp Leu Tyr Ser | | | |
| 70 75 80 | | | |
| | | | |
| gac ctc cgg gac gga cgc aac ctg ctg agg ctc ctc gag gtg ctc tcg | | | 5558 |
| Asp Leu Arg Asp Gly Arg Asn Leu Leu Arg Leu Leu Glu Val Leu Ser | | | |
| 85 90 95 | | | |
| | | | |
| gga gag ata ctg gtgagctgtg gtcatgaagg gaagtggggg ggcctwagaa | | | 5610 |
| Gly Glu Ile Leu | | | |
| 100 | | | |

```
aagtgtccaa ggggaccagc tggaagaaca gccctcagag agagtgacgg cacagggcgg   5670
gaagcagtgg ctccctctgc tcagagratg ggttcatttc aagtgccttt gccacttaga   5730
ttacatagga gcattgcttc atggagacag gaacagtggc cccattgaaa acatttcttt   5790
tcccacctac tctgggtgca attaattccc ttgggaatct taatctgccc aagcctcatc   5850
tgtaagctca gctttggctc cagccctggg gctgtgcctg tctgtgttcc tgaggtaggt   5910
catggggaag gtgtgcaaag ctgggccctg tgaaggctgg ggaagaaggt ggaagcccac   5970
```

| | | | |
|---|---|---|---|
| agtcccgtgc cattttgccc ccgtccctcc acag cca aag cct aca aag ggc cgc | | | 6025 |
| Pro Lys Pro Thr Lys Gly Arg | | | |
| 105 110 | | | |
| | | | |
| atg cgg atc cac tgc ctg gag aac gtg gac aag gca ctg cag ttc ctc | | | 6073 |
| Met Arg Ile His Cys Leu Glu Asn Val Asp Lys Ala Leu Gln Phe Leu | | | |
| 115 120 125 | | | |
| | | | |
| aag gag cag aaa gtg cac ttg gaa aac atg ggc tcc cat gac att gtg | | | 6121 |
| Lys Glu Gln Lys Val His Leu Glu Asn Met Gly Ser His Asp Ile Val | | | |
| 130 135 140 | | | |
| | | | |
| gac gga aac cac cga ctg acc ctt ggg ctg gtc tgg acc atc atc ctt | | | 6169 |
| Asp Gly Asn His Arg Leu Thr Leu Gly Leu Val Trp Thr Ile Ile Leu | | | |
| 145 150 155 | | | |
| | | | |
| cga ttc cag gtaccccagc acactgtcac acagggtgtg gttcctgccc | | | 6218 |
| Arg Phe Gln | | | |
| 160 | | | |

```
tggctctgca ccgcaagccg ttcctgctgg cccatgacac aacaaacaca agatggagg    6278 atctagaacc ttatgtagca gctgccatgg cggcgctatc caagcaccag atcagtggac    6338
tcccctcttt cagcagggta gaaaccagct gggtgaatg tcacacccct gtggcaaatt    6398
ccctgtgttc tggtctgtgt gttggtcgtg tgcaatggga ccaggaccac aggttggtcc    6458
acaggagact ggaagtttta ccaactggtc cttcaccaca gggatttggg aacttctaga    6518
gggtctggtc actggcacca attccctgcc ataaactctg cctgcctccc caatggaac     6578 agtcaccctc ctcctcctca tgccccagtg tcctcatgcy atcacagcgt tcctgatcac    6638
cccttccctt cccgggttct gtcggcttca ccttggagag ccagcttta gagaccttgg    6698
```

```
agagccagct ctcagaaaat gttcactctt ctgcctgcag ttccccacct ggagggacca      6758
gcaccctcca ctcagacaca cccattcttc agcatcctac cctaatctgc tgcctcaaat      6818
cccttgcacc cagtgttttg tggtccctgg cctaggttga aaggacctca ggctatgcct      6878
gtccacccca ttaccacagt ctaaagagca gtttcctgcc atttatctga gcatctctga      6938
taacaccagg agttcctgtc cagggactga gggccctgct tgcttccttc ctag atc        6995
                                                              Ile caa gac atc agt gtg gag aca gaa gac aac aag gag aag aag tca gcc        7043
Gln Asp Ile Ser Val Glu Thr Glu Asp Asn Lys Glu Lys Lys Ser Ala
        165                 170                 175 aag gat gcc ctg ctt ctg tgg tgc cag atg aag act gca gg                 7084
Lys Asp Ala Leu Leu Leu Trp Cys Gln Met Lys Thr Ala Gly
    180                 185                 190 gtgaggacac cctgggcgtg tggcactgga gggtcagtga cccccaggct gtgctgggct      7144
ccaggaacca tgagctggtg actgccctgg agtcatagaa cagagctcag ccctactcac      7204 catttctga atctctgttt atag t tat ccc aac gtc aat gta cac aac ttc       7256
                             Tyr Pro Asn Val Asn Val His Asn Phe
                                         195                 200 acc acc agc tgg aga gat gga cta gct ttc aac gcc atc gtg cat aaa       7304
Thr Thr Ser Trp Arg Asp Gly Leu Ala Phe Asn Ala Ile Val His Lys
            205                 210                 215 cac cg  gtgagaagat ggggttagca aacgcagcag agctgctggg tcggctaatg        7359
His Arg acctggggtg cacatgtgga gacagagatg agatgagctg cacagcagtc agacggaagg    7419
aatagcactc ggagcagaac cagaacatgg gggtgcaggg ctgcgcagag cacttgtgat    7479
gggaagcagg ggaggtggtg tggggagggg ctgtgagcag cagtgtgggt ttgggatgcc    7539
tacttctgga caaaattggg tcggtgactt agggataaag attggtgtgg gtttcctctt    7599
cctcttcrag atctcacatg tttctgatcc cttctgtctt gcctccccac ccag g cca    7657
                                                                Pro
                                                                220 gac ctg ctg gat ttt gag tct ctg aag aag tgt aat gca cac tat aat       7705
Asp Leu Leu Asp Phe Glu Ser Leu Lys Lys Cys Asn Ala His Tyr Asn
            225                 230                 235 ctg cag aat gca ttc aat ctg gct gaa aag gaa ctg gga ctt acc aag       7753
Leu Gln Asn Ala Phe Asn Leu Ala Glu Lys Glu Leu Gly Leu Thr Lys
            240                 245                 250 ctg ctg gat ccc gaa g gtggggccag agctatgtga aaaagaggtg gtagggtaga   7809
Leu Leu Asp Pro Glu
            255 gacaggaggt ggaccagtgg ttgccagggg ctgcggaggg ggaagacatg gagtaaccac    7869 caactgatac aggggcttct ttggtggggg aagagaatgt tctggaatta gaaagtggtg    7929 atggttacac aaccttgtaa atatactgaa aaacacgtgg ttgctcacac ccagcacttt    7989 gggaggccaa ggcaggagga tcacttgagc ctaggagttt ggtaccagcc tgggcaacat    8049 agtgagaccc catgactacc cctcccccc aaaaaaaata tatatcttta cactgaaaac     8109 cactgaatta tatacattga aaggttgaat tttatggtgt gacaatcatt tctcaggttt    8169 tttttttttt taacaaaaga ctgtaggtag gaaraaaggc agcccagtga cagaaagagc    8229 cctggactgt gggttgtgtc ccaggcagag cacagaggag ctctgtgaca tacagccagt    8289 ggctagcctc tctgtggctc agttycctca tgtcttaaaa gagagaattg gtctctaagg    8349 gctcttctga aattctagga ttctaaatta agctacatgt tgctggccac ggtggtacct    8409
```

```
gcctatagtc ctagctgcta gtgaggctga ggcgagagga tcacttgagc ccaggagttc    8469
taggctgcag tgggttatgc tgattggata tctacactaa attcagcact ggtgacctcc    8529
tgggagcagg ggaccagcag gttacctaag gaggactgaa ccagtccagg tcagaatgga    8589
gcaggtcaaa actcccacac tgatcagtag tgggatcaca cctgtcaata gccacagtac    8649
tccagcttgg gcaacagcga gacccatctc tattttttta aaacaaattt ttaagaaaaa    8709
aaattaagct gcatgacctt ccactctcac ccagaactgg cctgtagtca gctgaccttg    8769
ctgattggtt cctgtggttc tggtcataat gccgatgaga tcgatgagat cagtaacagc    8829
cmctgggctc ttttttttt ttttgagacg gagtctcact ctgttgccca gactggagtg    8889
caatggcgcg atctcggctc actgcaacct ccgcctcctg ggttcaagca attctcctgc    8949
ctcagcctct tgagtagctg agattacagg cgcatcccac cacgcccggc taattttgt    9009 attttagta gagacagggt ttcaccatgt tggtcaggct ggtctctaac tcctgacctc    9069
gtggtccgcc cacctcggcc tcccaatgcg ctgtgataac aggtgtgagc cccgcgcct    9129 gactgcgatt aggctcttat ttgatacctg gttctgcact tgatgtgttt taatcttcac    9189 aacaccctt tgaaatcagt actgttgtta tcctcagttt atggaagaga agatgggggc    9249
ctataatggg taagcaactt gcccaggtcc tccggcagat ggagctgaga ttggcgttca    9309
ggcagcctgg ctccagagcc tgtttcctcc gctgcctctg ggaaagtgga gaccaatctt    9369
ggtgcaacca gaacagggag gagagaaagg ctcgcctgct ggaggtgctc cttaagttca    9429
ctgggtggat gttcactggt cttggccatt ttctccctgt tttccattct acctgtagcc    9489
ctatcacctg ggccttttta ctgcagaatg acaagtgtca gcgagctagc aacagacata    9549
ggcttcatgc agtgctcctt ggagagcctc tgggtagcat ggctgtaatt cagaacctgg    9609
aaataaagct aagcattctg taactttccg agatgacttc agtggctcct gcctgcccat    9669
gtatttccag aaataggcaa gaggcttctg gtctcatagt cttaccttta ggataaaatc    9729
tggcctattt aaaagaaccc acagatttca agttatggtc agcctcagtt gtgcgctgga    9789
agccaattcg gcttgaaaga cactcccctc cttgggccca cagctgagct ttaggattga    9849
ggttagaaac ggcgtgatca cacctggaga tggtgctgag agctggcctc tgtccccact    9909
gagctgcagg gatcacaggg cccatcgatc tgagcatcct aggttcagga ggcttagttc    9969
ataccttccg tcccactgcc cctcaatcca ttgacttctt aaacattatt ctagcctaaa   10029
agtccatgat ccatccccac atagcaatgc tgtttctttt cttgcttttc ttccccaaac   10089
aactgatttt ggtctccacg gggaactctg gtaaaagct tccttgtgct tctgggtt    10149 gtgctctgct tggagggccc ttcttgtttc caggagaagg ggaaaaaaag atgagctttt   10209
tggtgccctt ttcatttgaa tgggtaagtt gtcattttgc tctaaaagga gatggagaga   10269
tgtcagcctt ggaggactgg gcaggcccag ggtttgggt aagtgatgca agttatggat   10329
gaacttctgg gaggcctgac ccaaatggtc ctctcttgca g ac   gtg aat gtg gac   10384
                                              Asp Val Asn Val Asp
                                                            260 cag cca gat gag aag tca atc att acc tat gtg gct act tac tac cat      10432
Gln Pro Asp Glu Lys Ser Ile Ile Thr Tyr Val Ala Thr Tyr Tyr His
    265                 270                 275 tac ttc tcc aag atg aag gcc ctg gcc gtg gaa ggc aag aga att ggc      10480
Tyr Phe Ser Lys Met Lys Ala Leu Ala Val Glu Gly Lys Arg Ile Gly
    280                 285                 290 aag gtactgtcca tgggcagtag gcataaaggc cagaggaggc ccggctgagg           10533
Lys
295
```

-continued

```
ggtcttactg ccctagtgca agggcagggt ggagctgcag gactgggcca gggaccctgt   10593
ggctgggact gtcacgtccc tgtcttctgc ctcccag gtg ctg gac cat gcc atg   10648
                                         Val Leu Asp His Ala Met
                                                             300
```

```
gag gca gag cgc ctg gtg gag aaa tac gag tcc ctg gcc tcg gag ctg   10696
Glu Ala Glu Arg Leu Val Glu Lys Tyr Glu Ser Leu Ala Ser Glu Leu
            305                 310                 315 ctg cag tgg atc gag caa acg atc gtg acc ctc aat gac cgg cag ttg   10744
Leu Gln Trp Ile Glu Gln Thr Ile Val Thr Leu Asn Asp Arg Gln Leu
        320                 325                 330 gcc aac tcc ctt agc ggg gtc cag aac cag ctg cag tcc ttc aac tcc   10792
Ala Asn Ser Leu Ser Gly Val Gln Asn Gln Leu Gln Ser Phe Asn Ser
    335                 340                 345 tac cgc acc gtg gag aag ccg ccc aa  gtaggtgtcc ctggggcccc          10838
Tyr Arg Thr Val Glu Lys Pro Pro Lys
350                 355
```

```
acccttccct gagctgtgct cccacgagag gaagcctaaa ttagcacagc cttcagggag   10898
ggaaatttgg cagtacataa atgcagtgga gatttcccac accagaagca tccaaacaac   10958
atagttgata caaaataaaa ttttttaatg attagtcgtt tttaaaaatc atgctgtggg   11018
ccgggcatgg tggctcacgc ctgtaatccc agcactttgg gaggccaagg cgggcgcatc   11078
accgagacca gtctggccaa catggtgaaa ccccatctct actgaggtcg ggagtttgag   11138
accagcctgg ccaacatggt gaaacccccgt ctccactaaa attacaaaaa aattagctgg   11198
gcatggtggc acacgcctgt catcccagct actcggagg ctgaggcagg agaaccacct   11258
gaacccggga gacagaggtt gcagtgagcc aagatcacgc cactgcactc caacctgggt   11318
gacagagcaa gactccgtct caaaaaacaa acaaacatgc tgtggaaatg attgctatga   11378
tgtgttgagt cagtgcgatc catcagataa gattactgat caggtgtcat ggcaacccaa   11438
tcctagcata ggatagaggg gactggacct gacaggcagg tcacaaccgg caacatgggt   11498
gtggctggta acgtgagaat tgcagaggtt cttatcattt cagtatttta gcaattaact   11558
gttccaagta tgtgattgct gttaggcaat tctgttcagt acctgccaaa acgtctgtgt   11618
ttatgctgtc atggagttct tttggagtta atatatatca gctctgaaac taatattagt   11678
ccagaaaaca attgtttcta tacattccag ggaatgattt aaggtgtacc ctttaaccta   11738
ggaagttgtc ttctggacat taaacaaaga tgtagcttca aggatgttta tcaacacaac   11798
cactagaaaa gaaaaataag tcatgggcag ccactgaaaa taatattaaa gaaatgcatt   11858
tattgacatg gaaaggtgtt catgaaaaat aagtgggga aataggttat aaaagaatta   11918
ttttggctgg gcaccgtggc tcatgcctgt aatcccagca cttgggagga ctgaggcggg   11978
tggatcactt gaggtcagga gtttgagacc agcctggcca gcatggtgaa accccatctc   12038
tactaaaaat acataaatta gccaggtgtg gtggtgcatg cctgtaatcc cagctactcg   12098
ggaggctgag gcaagagatt ggcttgaacc cgggaggcag agrttgcagc gaacccagat   12158
cgcaccactg cactccagcc tgggtgacaa agcaagactc tgtctcaaaa taaaataaaa   12218
tgatgttctt ttggttagcc catattttct ggcttccaca taaaaagttt atattgcttt   12278
tgtaagaaga aaagcaacac aggacaccca tttggaagag taaagagtcc ttgtgaccct   12338
cgtgggcttt aattctgacc ccaacccggc ctcctgcctc ag g ttt acc gag aaa   12393
                                                Phe Thr Glu Lys
                                                         360 ggg aac ttg gaa gtg ctg ctc ttc acc atc cag agc aag ctt cgg gcc   12441
Gly Asn Leu Glu Val Leu Leu Phe Thr Ile Gln Ser Lys Leu Arg Ala
```

-continued

|  |  |
|---|---|
| 365 370 375 | |
| aac aac cag aag gtc tac acg ccc cgc gag ggc cgg ctc atc tcg gac<br>Asn Asn Gln Lys Val Tyr Thr Pro Arg Glu Gly Arg Leu Ile Ser Asp<br>380 385 390 | 12489 |
| atc aac aag gtccgtggct gcccacaggc cacccaccct cagggcaggc<br>Ile Asn Lys<br>395 | 12538 |
| cctggcccag atgccttgca cacatcccca aacccggggc catgtcgacc ttcaccaagt | 12598 |
| tctactatct gctgcccccaa cttgaaactc gagcactctg cccagctgcc cacactgtgc | 12658 |
| cagatgtgat tctcccatcc tctcaggcac acggctccct gtcccttttgt ctgactctcc | 12718 |
| atacgaggtc acataaggaa attatgcccc aagttcctca gcttgttaaa cctgtcccca | 12778 |
| actcactatc ccttctttta ttttttcac aatattgtaa gattactaaa agtaaaaata | 12838 |
| aggttcgcac acagtcctgc aacacaaag gaatcagatg gtttccactg ttcgtgctcc | 12898 |
| ctccagtcct tttccagaag cttctacatg gcttcacaga ctcccagcgc tgccctgttt | 12958 |
| cctgtttcca cgcccaggcg tctcacccac tgcattccac ggatccacca gaccgagctt | 13018 |
| ccatgggact taccatgtgc ctccagcccc actgagccct ccccaccctg tcccttccac | 13078 |
| taaccctgtc cccaccccat ag gct tgg gag cgg ctg gag aag gcg gag cac<br>Ala Trp Glu Arg Leu Glu Lys Ala Glu His<br>400 405 | 13130 |
| gag cgt gag ctg gcc ctg cgc acc gag ctc atc cgc cag gag aag ctg<br>Glu Arg Glu Leu Ala Leu Arg Thr Glu Leu Ile Arg Gln Glu Lys Leu<br>410 415 420 | 13178 |
| gag cag ctg gcc gcc cgc ttc gac cgc aag gct gcc atg cgg gag acc<br>Glu Gln Leu Ala Ala Arg Phe Asp Arg Lys Ala Ala Met Arg Glu Thr<br>425 430 435 | 13226 |
| tgg ctc agc gag aac cag cgc ctc gtg tcc cag gtaggacttg aggctcctag<br>Trp Leu Ser Glu Asn Gln Arg Leu Val Ser Gln<br>440 445 450 | 13279 |
| gatgcttagg ctggtcagaa ctgggagaga dacagggtgg ataagaagcc ccgcgggtg | 13339 |
| gagagacaat gaaacacaaa atccgtcacc tgggtaaaaa ggcctagagg tccgggagcc | 13399 |
| aggggccaga gggtgggaca ggagagaggg ttggtgagac aggatggggg tgggatagag | 13459 |
| agggaactta gagccaccgc atggagctgg gatcttgcag gccaagtgcc ctgcaggaca | 13519 |
| gaggagcagg cagaggcact gtcccttggt ccccacacct cctctccctg cccccgacac | 13579 |
| ag gac aac ttt ggg ctg gag ctg gca gct gtc gag gca gca gta cgg<br>Asp Asn Phe Gly Leu Glu Leu Ala Ala Val Glu Ala Ala Val Arg<br>455 460 465 | 13626 |
| aag cac gaa gcc att gag acg gac atc gtg gcc tac agc ggc cgg gtg<br>Lys His Glu Ala Ile Glu Thr Asp Ile Val Ala Tyr Ser Gly Arg Val<br>470 475 480 | 13674 |
| cag gca gtg gac gcc gtg gct gca gag ctg gcc gcc gag cgc tac cac<br>Gln Ala Val Asp Ala Val Ala Ala Glu Leu Ala Ala Glu Arg Tyr His<br>485 490 495 | 13722 |
| gac atc aag cgc atc gcc gct cgg cag cac aac gtg gca cgg ctc tgg<br>Asp Ile Lys Arg Ile Ala Ala Arg Gln His Asn Val Ala Arg Leu Trp<br>500 505 510 | 13770 |
| gac ttc ttg cgg cag atg gtg gcc gcc cgg cgg gag cgg ctc ctc ctc<br>Asp Phe Leu Arg Gln Met Val Ala Ala Arg Arg Glu Arg Leu Leu Leu<br>515 520 525 | 13818 |
| aac ctg gag ctg cag aag gtg ttc cag gac ctg ctc tac ctc atg gac<br>Asn Leu Glu Leu Gln Lys Val Phe Gln Asp Leu Leu Tyr Leu Met Asp<br>530 535 540 545 | 13866 |
| tgg atg gaa gag atg aag gtaccagtga ggcgtgctgg gtgggtaag<br>Trp Met Glu Glu Met Lys | 13914 |

```
Trp Met Glu Glu Met Lys
            550 agtgatcaag agtcgagggg gccccacagt gggtgcgtcc gcccgtctgc tcggccgatc    13974 tctgtggagt gtgaaccagc acagggccct gtccccagtt gcagggaaca agtaaacag    14034 ggccctgtcc acatggggtt cgtgtccaca tggaggaggc tgatgacaaa acccacggac    14094 ctttccgtaa acaaaagagc aggggccata aaccactga tgaaactgga caggtgtggt    14154 gtgaggggct ggtcagacaa ggcctctgag aaaataccat ttaagccgag accagaatag    14214 tgccaggagc cagcacagag agctctcagg agagaatgtt ccgggcagaa ggaacagccg    14274 gcacaggccc tcggcctgga tcagcatggt gtgttcagga tcagaaggaa ggccggtggg    14334 ctgtgagcat gaggagtggg ggccatggac tgagatttgg gagggcacgg ccagcccact    14394 agggccttac aggcctggtc agggagtttg gattttattc aaagtaacat ggatccttta    14454 aagtgatttg aaggggccag cgcagtggc tcatgcctgt aatcccagct ctttgggagg    14514 ccaaggcagg cagatcactt gaggtcagga gttcaagacc agcctggcca acatggtgaa    14574 accccgtgtc tataaaaata cagaaattaa ccaggtgcgg tggtagcgca tgcctgtagt    14634 cccagctact caggaggctg agacagcaga atcgcttgaa cccaggaggc ggaggttgca    14694 gtgagccaag attgcaccac tgcactccag cctaggtgat agagcaagac tcagtcaaaa    14754 aaaaaaaaaa aaagcagyta ggcaaggtgg ctcacgccta taatcctaag actttgggag    14814 gccgaggcgg gcggatcacc tgaggtcagg agtccaagac cagcctggcc aacatggtga    14874 aaccccatct ctgctaaaaa tacaaaaatt agctgagtgt ggtggcacac gcctgtaatc    14934 ccagctagtc aggaggctga ggaaggagaa ttgcttggac ctgggaggtg gaggttgcag    14994 tgaactgaga ttgtgctact gcactccagc ctgcactaca ggagcgagac tccatctcaa    15054 aataaataaa taaataaagt gattagaagg ttttgagagg gggagagatt tgattgtacc    15114 ttatgtttgt aaaaaagtca ctttggctac tctgaagaag gcctgtgggc aggcagcatg    15174 acagcgagac cgttagaggt tgctgccatc ttccaggcgg gcagcggcta ggagggtgga    15234 ttggggagag atgtggaagg aaggctgctg ggtgctgggg cggagcggtg gcggcaggag    15294 ggtgtcgatg attctgaggc tgagaagatt agtcacagca aagcttccaa gagcaggagt    15354 tagttagaac attgttccac agcagggag ttcaggataa ggaggtcggg gtgccagggc    15414 agaactgggg tatctcaagt atgtgtgagc aagcaggttt ctcacctggg tgcaacacct    15474 ggggccgtgg agaagttgga agaaaaacgc agccaggtta cgcgcgtctgt gctcaggcgg    15534 gcatgtgcac ttcatgtgtg cctggcag ggc cgg ctg cag tct cag gac ctg    15586
                                Gly Arg Leu Gln Ser Gln Asp Leu
                                                555 ggc agg cac cta gca gga gtg gag gac ctg ctg cag ctg cac gag ctg        15634
Gly Arg His Leu Ala Gly Val Glu Asp Leu Leu Gln Leu His Glu Leu
560             565                 570                 575 gtg gag gca gac atc gcc gtg cag gcc gag agg gtg cgg gcc gtc agc        15682
Val Glu Ala Asp Ile Ala Val Gln Ala Glu Arg Val Arg Ala Val Ser
                580                 585                 590 gcc tct gcc ctg cgc ttc tgc aac cca ggg aaa g gtgagaagtc                15726
Ala Ser Ala Leu Arg Phe Cys Asn Pro Gly Lys
                595                 600 agcgaaggca ctgagaggg aggggctggg aaggagcaca tcaagagccg aggtggaagg        15786
gttgggaaac ctggggacgg gaaagatggt ggccaaacga tggtgactga gctaaagcca        15846
gggagggaag tccaagagag tgtggtgtgca gggagcagcc ggagggctgg gttaaggctc        15906
```

```
                                                          -continued
tgaccctctc ctgtgacttt ctcag ag tat aga cct tgc gac ccg cag ctg         15957
                                  Glu Tyr Arg Pro Cys Asp Pro Gln Leu
                                      605             610 gtg tcg gag cgg gtg gcc aag cta gag cag agc tat gag gca ctg tgc         16005
Val Ser Glu Arg Val Ala Lys Leu Glu Gln Ser Tyr Glu Ala Leu Cys
            615                 620                 625 gag ttg gca gcg gcg cgg cgg gcc cgg ctg gag gaa tca cgg cgg ctc         16053
Glu Leu Ala Ala Ala Arg Arg Ala Arg Leu Glu Glu Ser Arg Arg Leu
        630                 635                 640 tgg cgt ttc ctc tgg gag gtg ggt gaa gct gag gcc tgg gtg cgg gag         16101
Trp Arg Phe Leu Trp Glu Val Gly Glu Ala Glu Ala Trp Val Arg Glu
    645                 650                 655 cag cag cac ctc ctg gcc tca gcc gac acg ggc cga gac ctg acc ggt         16149
Gln Gln His Leu Leu Ala Ser Ala Asp Thr Gly Arg Asp Leu Thr Gly
660                 665                 670                 675 gcc ctc cgc ctg ctc aac aag cac aca gcc ctg cgg ggc gag atg agc         16197
Ala Leu Arg Leu Leu Asn Lys His Thr Ala Leu Arg Gly Glu Met Ser
                680                 685                 690 ggc cgg ctg ggg ccc ctg aag ctc acc ctg gag cag ggc cag cag ttg         16245
Gly Arg Leu Gly Pro Leu Lys Leu Thr Leu Glu Gln Gly Gln Gln Leu
            695                 700                 705 gtg gcc gag ggt cac cct ggg gca agc cag gcc tct gcc cgt gca gct         16293
Val Ala Glu Gly His Pro Gly Ala Ser Gln Ala Ser Ala Arg Ala Ala
        710                 715                 720 gaa ctc caa gcc cag tgg gag cgg cta gag gcc ctg gcc gag gag cgt         16341
Glu Leu Gln Ala Gln Trp Glu Arg Leu Glu Ala Leu Ala Glu Glu Arg
    725                 730                 735 gcc cag cgg ctg gcc caa gcc gcc agc ctc tac cag ttc cag gcc gat         16389
Ala Gln Arg Leu Ala Gln Ala Ala Ser Leu Tyr Gln Phe Gln Ala Asp
740                 745                 750                 755 gca aac gac atg gag gcc tgg ttg gtt gac gca ctg cgc ctg gtg tcc         16437
Ala Asn Asp Met Glu Ala Trp Leu Val Asp Ala Leu Arg Leu Val Ser
                760                 765                 770 agc ccc gag ctg ggg cac gac gag ttc tcc acg cag gct cta gcc agg         16485
Ser Pro Glu Leu Gly His Asp Glu Phe Ser Thr Gln Ala Leu Ala Arg
            775                 780                 785 cag cat cgg gcc ctg gag gag gag att cga agc cac cgg cca acc ctg         16533
Gln His Arg Ala Leu Glu Glu Glu Ile Arg Ser His Arg Pro Thr Leu
        790                 795                 800 gac gcc ttg agg gaa cag gca gca gcc ctg ccc ccc aca ctg agc cgc         16581
Asp Ala Leu Arg Glu Gln Ala Ala Ala Leu Pro Pro Thr Leu Ser Arg
    805                 810                 815 acg ccc gag gtg cag rgc cgg gtg ccc acc ctg gag cgg cac tac gag         16629
Thr Pro Glu Val Gln Xaa Arg Val Pro Thr Leu Glu Arg His Tyr Glu
820                 825                 830                 835 gag ctg cag gcc cgg gca ggc gag cga gcg cgg gcc ttg gag gca gcc         16677
Glu Leu Gln Ala Arg Ala Gly Glu Arg Ala Arg Ala Leu Glu Ala Ala
                840                 845                 850 ctg gcg ctc tac acc atg ctc agc gag gcc ggg gcc tgt gga ctc tgg         16725
Leu Ala Leu Tyr Thr Met Leu Ser Glu Ala Gly Ala Cys Gly Leu Trp
            855                 860                 865 gtg gag gag aag gag cag tgg ctc aac ggg ctg gcc ctg cct gaa cgc         16773
Val Glu Glu Lys Glu Gln Trp Leu Asn Gly Leu Ala Leu Pro Glu Arg
        870                 875                 880 ctg gag gac ctg gag gtc gtg cag cag ag gtaggcccct caggctccta           16822
Leu Glu Asp Leu Glu Val Val Gln Gln Arg
    885                 890 gtgggaccag ccttgggagg tgggggtggk ggggccagga tgtgggtggt gagtccctcc       16882
ataaacttcc tgcctcaccc ctttgagtct taatggttgt ccatttctag ttttaacaaa       16942
```

```
aaatgttaac catactcaca agtagagaca tttcaccaca aacccctcta cacccgtcac    17002
ccagattcag tcattgccaa catcttgctc tatttggttc tctgccctttt taaaaagcaa   17062 atccccaaga ttagcacatc cctcctacct tcttcagggt gtgcccttta agaaatacaa   17122
ggaagcggcc gggcacggtg gctcacacct gtaatcccag cactttggga ggccgaggca   17182
ggcggatcac gaggtcagga ggtcgagacc atcctggcta acatggtgaa acgctgtctc   17242
aactaaaaat acaaaaaatt agccgggcac agtgggggc gcctgtagtc ccagctactc    17302
gggaggctga ggcaggagac tggcatgaac ctgggaggcg gagcttgcag tgagccgaga   17362
tcgtgccact gctctccagc cttggcgaca gagcgagact gtctcaaaaa aaaaaaaaaa   17422
aaaaagaaaa gaaatacgag gaagcattct tacctacaat atattatttt caaattgtct   17482
gtgtggactt aaaatagctg aggctttgaa gttataaacc ttttagacag agacactaaa   17542
atagttttat ttacagaata aatcttcaaa tcatttattc aataataaat cttaaaaatt    17602
tttttataga accacaatac cattatcaca tagaacaaaa ttaggaatttc ttttttttt   17662 tgagatggag tctcactctg tcacccaggc tggagcgcag tggygcgatc tsggctcact   17722
gcatgctctg cctcccgggt tccagcgatt ctcctgcctc agcctcccaa gtagctggga   17782
ctacaggcac ccaccaccat gcccagctaa tttttttgtat ttttttatta gtagagacag   17842
ggtttcacca tgttagcgag gatggtctcg atctcctgac ctcgtgatcc acccggcttg   17902
gcctcccaaa gtactgggat tacaggcatg agccactgcg cygggtcagg aatttcttga   17962
tatgatctat gatcaatgtg taatcaaatt tcctggtgtt taaaaaaatr taattaggtc   18022
aggcctggtg gctcacacct gtaatcccag cactttggga ggccaaggca ggagtatcac   18082
ttgattccaa gagttcataa ccagcctggg caacatagtg agactccacc tctacaaaat   18142 tttttttta attagccagg catggtggca ggcgcctgta gtcccagcta ctggggaggc   18202
tgaggcagga ggattgcttg agcccagagg tcgaggctgc agtgagctga gatcgtgcca   18262
ctgcactcca acctgggtga cagagtaaga ccctgtctca aaaaaataaa taaaaataaa   18322
aatgtaatta aagatttttt ttagtttca aggtatccta atgtagaggt taacaaactg    18382 caaccccttgg gccaaatcca gcctgctgcc tgtttctgta aataaagttt tttttggttt   18442
tttttttttt tttttttttt gagacggagt cttgctctgt cccccaggct ggagtgcagk   18502
ggcacaatct tggctcactg caagctccgc cgcccgggtt cacgccattc tcctgcctca   18562
gcctcccaag tagctgggac tacaggcacc cgccaccaca cctggctaat ttttttgtatt   18622 tttagtagag acgaggtttc mccgtgttag ccaggatggt ctcgatctcc tgaccttgtg   18682
atccacccat ctcagcctcc caaagtgctg ggattacagg cgtgagccac catgcccggt   18742
ctgtaaataa agttttactg gaacagagct acactcgccc ttttgcgtat tgcccgtggc   18802
tgctttcagg ctacagcagc agggctgaat agttgccgca gcagctgcat ggctcacgaa   18862
gcctataata tttaccatca agcccttcac agaaaacatt tgcagaccct gccctattag   18922
aacatcaaat gtcggccagg cgaggtggct cacgcctgta atcccagcac tttgggaggc   18982
caaggcgggt ggagcatgag gtcaggagtt caagaccagc ctggccaaga tagtgaaaca   19042
cccgtctcca ccaaaaatac aaaaattagc taggcttggt ggcgggcacc tgtaatccca   19102
gctattcggg aagcggaggc agaaaattgc ttgaacccgg gaggcggagg ttgcartgag   19162
tcgagattgc accactacac tccagcctgg gtgacagagc gagactccat ctcaaaaaca   19222
aaacataaaa tgtccctgga agaagttatc cttcacattt tcatcactca gacaaatatt   19282
```

```
tttggttatt acttcattttt ctaacacata ttagtgggat gagacccaga taggcagcta    19342
agggggaagt cccaggaggc tgagcagctc tgataaaggg ttggcccat gccagggtct     19402 agtttgactt gtgtgtctgt tcctgacctt tacctttcac catcttttga gcatttctag    19462
cgatgacagt tattctgctt gttttgggg agttgtgggg tccttcctg atgcacagat      19522 actatgaacc tcataggctg agaggcagag agactcctgc agataagcct cctggtgaag   19582
gagacaccct cctgggtgtt taagagaggt ggacttaggg ggactgggca catcgctgcc   19642
tcccacaatt cacgcctggc tcttccaccc tctcag g ttc gag acc ctg gag cct   19697
                                        Phe Glu Thr Leu Glu Pro
                                                                895 gaa atg aac acc ctt gca gca caa atc acc gcg gtg aat gac att gcc      19745
Glu Met Asn Thr Leu Ala Ala Gln Ile Thr Ala Val Asn Asp Ile Ala
900                 905                 910                 915 gag cag tta ctg aag gcc aac ccc cca ggc aaa gac cgc att gtc aac      19793
Glu Gln Leu Leu Lys Ala Asn Pro Pro Gly Lys Asp Arg Ile Val Asn
            920                 925                 930 acc cag gag cag ctc aac cac ag  gtgggtttgg raggcagga ccrggaaact     19846
Thr Gln Glu Gln Leu Asn His Arg
                935 gacagaaaaa tgaagcaatg gggatggcag tgagaggcag gttttgtagg gcctggaagg    19906 gtggctacaa aggaggaagc aaaccagtct ggaatatgyt ggggaaggaa aaaggatgaa    19966 agagatgaga gaggggtca aggtggtctg aagcrgctgc tggccagaaa gggaggagtg    20026 aaggggagct accaagagag agagaagcag ggaagaagct tccaaacagg cctggccagg    20086 gcaggaagct gaaccttccc cctgctctca g g tgg cag cag ttt cgg cgt ctg    20139
                                    Trp Gln Gln Phe Arg Arg Leu
                                                        940   945 gca gac ggc aag aag gca gct ctc acc tca gcc ctg agc atc cag aac     20187
Ala Asp Gly Lys Lys Ala Ala Leu Thr Ser Ala Leu Ser Ile Gln Asn
            950                 955                 960 tac cac tta gag tgc acg gag acc cag gcc tgg atg aga gag aag acc     20235
Tyr His Leu Glu Cys Thr Glu Thr Gln Ala Trp Met Arg Glu Lys Thr
        965                 970                 975 aaa gtc atc gag tcc acc cag ggc cta ggc aac gat ctg gct ggg gtg     20283
Lys Val Ile Glu Ser Thr Gln Gly Leu Gly Asn Asp Leu Ala Gly Val
    980                 985                 990 ctg gcc ctg cag cgc aag ctg gcc ggc acg gag cgg gac ctg gag         20328
Leu Ala Leu Gln Arg Lys Leu Ala Gly Thr Glu Arg Asp Leu Glu
995                 1000                1005 gcc atc gcc gcc cgg gtg ggc gaa ctg act cga gag gca aat gcc         20373
Ala Ile Ala Ala Arg Val Gly Glu Leu Thr Arg Glu Ala Asn Ala
    1010                1015                1020 ctg gct gcc ggc cat ccc gct cag gca gyg gcc atc aac gcc cgg         20418
Leu Ala Ala Gly His Pro Ala Gln Ala Xaa Ala Ile Asn Ala Arg
1025                1030                1035 ctg aga gag gtg cag acc ggc tgg gag gac ctc agg gcc acc atg         20463
Leu Arg Glu Val Gln Thr Gly Trp Glu Asp Leu Arg Ala Thr Met
1040                1045                1050 cgg cgt cga gaa gag tcg ctg ggg gag gcg cgg cgg ctg cag gac         20508
Arg Arg Arg Glu Glu Ser Leu Gly Glu Ala Arg Arg Leu Gln Asp
1055                1060                1065 ttc ttg cgc agc ttg gat gac ttc cag gcc tgg cta ggc cgc act         20553
Phe Leu Arg Ser Leu Asp Asp Phe Gln Ala Trp Leu Gly Arg Thr
1070                1075                1080 cag act gct gtg gcc tct gaa gaa ggg ccg gcc acc ctg cct gag         20598
Gln Thr Ala Val Ala Ser Glu Glu Gly Pro Ala Thr Leu Pro Glu
1085                1090                1095
```

-continued

| | |
|---|---|
| gca gag gcc ctc ctg gcc caa cat gca gcc ctg cgg gga gag gtg<br>Ala Glu Ala Leu Leu Ala Gln His Ala Ala Leu Arg Gly Glu Val<br>1100                      1105                      1110 | 20643 |
| gag cgg gcc cag agc gag tat agc cgg ctg cga gcc ctg ggc gag<br>Glu Arg Ala Gln Ser Glu Tyr Ser Arg Leu Arg Ala Leu Gly Glu<br>1115                      1120                      1125 | 20688 |
| gag gtg acc cgg gac cag gct gac ccc cag tgc ctc ttc cta cga<br>Glu Val Thr Arg Asp Gln Ala Asp Pro Gln Cys Leu Phe Leu Arg<br>1130                      1135                      1140 | 20733 |
| cga ctg gag gcc ctg gga act ggc tgg gag gag ctg ggc cga<br>Gln Arg Leu Glu Ala Leu Gly Thr Gly Trp Glu Glu Leu Gly Arg<br>1145                      1150                      1155 | 20778 |
| atg tgg gag agc cgg caa ggt cgc ctg gcc cag gcc cac ggc ttc<br>Met Trp Glu Ser Arg Gln Gly Arg Leu Ala Gln Ala His Gly Phe<br>1160                      1165                      1170 | 20823 |
| cag gga ttc ctg cgg gat gct cgt cag gct gag ggc gtg ctc agc<br>Gln Gly Phe Leu Arg Asp Ala Arg Gln Ala Glu Gly Val Leu Ser<br>1175                      1180                      1185 | 20868 |
| agc cag gtgaaagtcc agggcaaagt cccaagcagg aggaagagca aagtagggac<br>Ser Gln<br>1190 | 20924 |
| ccggggaaat gtgaaggagc aggatgggca ggaaggacat gctagcaaaa tgggcagcr | 20984 |
| cagtggttca cacctgaaat tccagcactt tgggaggcca agtaggagg atcacttgag | 21044 |
| gctgagaata tccagaccaa cctgggcaac atggcaagac cttgtctcta caaaaaaatt | 21104 |
| tttttaagaa aatagaagaa tttttaaaa agaaaaatgg gagccagaca ggatggctca | 21164 |
| cacttgtact cccagtattt tgggaggccg aggcaggaga ataacttgag ctcaggagtt | 21224 |
| tgagaccagc ctgggcaaca tagtgagacc cccatctcta tgaaaaaaaa aaattaactg | 21284 |
| gacatggtgg tgcatgcctg tagctccagc tactggggag gctgaggctg gtggatcact | 21344 |
| ggagccagga gtttgaggct gcagtgagct atgatatgcc actgcactcc aacctgggcc | 21404 |
| acagaatgaa accctctctc aaaaaaaaga aaagaaaaa agaaggaaaa atgagaatga | 21464 |
| aaaagacgtg aatataattt actaaaactg actttagaag aaatagaaag cccagtttgt | 21524 |
| catgtaactg ttaaatggaa tcaggagcta aagtgagat agaacaggat tgggctggg | 21584 |
| gaatggaagg tccttcccac ccagcttccc tgtgactttc tgaggctccc atgctggctg | 21644 |
| gcagcctccc tgtcttcaga gctctctggg ctaccctccc tgtctgcttg ttggtcccta | 21704 |
| cctctcagat ttgcccctgg gtgggtccct cctagggggg tgaattgtgc tggggaaaat | 21764 |
| gagctgaatg tcatccctcc cacacag gaa tat gtt ctg tct cac acg gag<br>                                             Glu Tyr Val Leu Ser His Thr Glu<br>                                                                      1195 | 21815 |
| atg cca ggg aca ctc cag gct gct gat gct gcc att aaa aaa ctg<br>Met Pro Gly Thr Leu Gln Ala Ala Asp Ala Ala Ile Lys Lys Leu<br>1200                      1205                      1210 | 21860 |
| gag gac ttc atg agc acc atg gac gcc aat ggg gaa cgg atc cac<br>Glu Asp Phe Met Ser Thr Met Asp Ala Asn Gly Glu Arg Ile His<br>1215                      1220                      1225 | 21905 |
| ggg ctc ctg gag gct ggc cgc cag ctg gta tct gaa ggc aac atc<br>Gly Leu Leu Glu Ala Gly Arg Gln Leu Val Ser Glu Gly Asn Ile<br>1230                      1235                      1240 | 21950 |
| cac gcc gac aag att cgg gaa aag gca gac tcc att gag agg ag<br>His Ala Asp Lys Ile Arg Glu Lys Ala Asp Ser Ile Glu Arg Arg<br>1245                      1250                      1255 | 21994 |
| gtctgatgag gacagtccat gaattagggt tcccaggggg gaatcggaga aacagggtga | 22054 |

```
cctcaaagat aaacgtggca caggaaaccc acagatgggg caggagctga cagagaagta      22114
gaggggaaga actaagtggt tgggagagggc tgggagattc cacccccaac cagggctaaa     22174
aggaagtcag gattcctggg tagcctcatt gtgctcccgg aagcgttat tcccctagaa       22234 gaaatggagg ccccctaggtt agccaaaggg tcacaatcct ttcacagcaa attccagagt    22294
ttcacaagag ggtgtcgttc cag g cac  aag aag aat caa gac  gca gcg cag      22345
                          His  Lys Lys Asn Gln Asp  Ala Ala Gln
                                    1260              1265 caa ttt ctg ggc cgt ctt cgg  gac aac cgg gag cag  cag cat ttc          22390
Gln Phe Leu Gly Arg Leu Arg  Asp Asn Arg Glu Gln  Gln His Phe
    1270                1275                1280 ctg caa  gat tgt cac gag gtgaggctcc ctggggcccc gggatattcc              22438
Leu Gln  Asp Cys His Glu
     1285 ctagccatcc ctttctcacc ttgagcctag aataagtcca gcacaaggta ccggagactg      22498 tgagccccttt catggcttct tcccaaggcg cccacttctc ctggctcact gtggccctgc     22558 tttatgccc ccctctcccc tcccttggaa atgtccctgt tttatgtttg gtccag           22614
ctg aag ctc tgg atc gac gag aag atg ctg aca  gcc cag gac gtg           22659
Leu Lys Leu Trp Ile Asp Glu Lys Met Leu Thr  Ala Gln Asp Val
1290                1295                1300 tcc tat gac gag gcc cgc aac ctg cat act aag  tgg cag aag cac           22704
Ser Tyr Asp Glu Ala Arg Asn Leu His Thr Lys  Trp Gln Lys His
1305                1310                1315 cag gca ttc atg gcc gag ctg gct gcc aac aaa  gac tgg ctg gac           22749
Gln Ala Phe Met Ala Glu Leu Ala Ala Asn Lys  Asp Trp Leu Asp
1320                1325                1330 aag gtg gac aag gtgagcagtg ctgtgggggc tgcctctggg cagagtcccc            22801
Lys Val Asp Lys
1335 catggtacgg gggagggcct ggctccagga cgtggttttt gtcatggtta gagattgtgg      22861 ggttctggtg ccacagctcc atggtggaaa gttatggcct ctgggaaaca aacgtctttg      22921 ttggagacaa agagtgggac agtgagtcca gaaccttgat aaagtacaaa ttagcaggta     22981 gcgaaactgc agcctggatt taacgccata actgttcctg agttcaaagc aggatggtgc     23041 tcttcagcag gctctgcaaa ccttgtctgg aaagggcttg ggytggatgg tcaatatctg      23101 aggctttgca gtccaaacag tttctactac aactactcat ctctgtcgtt gtagtgcaaa     23161 agcagcctca gagaataart gaatgaatga acatggctgt ttcccaataa aactttattt     23221 gtaaaaacag gcagtgggcc agattacccc gtgggctgta tgtagtctgc caatccttat     23281 tttcgagtct tgccgtccct ggttcttggt ctcccaccca gctgttcctc aagagtcaag     23341 gacagataaa gctttatatc tgctcagcaa gtatccctac agaacatggt acgtgctcaa    23401 cagtctgcga ggcactgcag ggtctacgaa aagacacttt ccttttctca agggcatgat    23461 ggttgggaca aaaggagacc agtgtgcttt caagtgtttc cattcgttca gcaaatattt    23521 acttggtgct actatatcca aagcattgta ttaggccctg cgtggggtcc gaaagggatc     23581 ccatggtagg ctccaccytg aaggaacaac actgtagcca ggatatgagg catatatgca    23641 ggtagctaaa tcgaatccag agcagaatct gatgagtgct gtgagagtgg ccccgttgaa    23701 gcctggggaa taaggagaga ggagatatgg aaattctaga agcagcaaca tccagggcag    23761 tccatggagg atgagtagaa tttggacaag tggagatatg gaggaaaaga tgtttccagg    23821 tagagaaaac caaacagaaa accagtggta ggcagtgcct gtttgggagc aaggggggtga    23881 gtgagtccag cagcagcaca gaatgtgtgc agggccccat ggaagaagag gtgggagaga    23941
```

```
agccccggga agtcctgacc accacatgcg tgtgcttcca agtgttgatt gtgctcaggg    24001
ttgtgaagct acccaggcag tgctagcctt tgatgctctc catcctgaca gccacagcca    24061
cctgcaaaat ggcctgaagg cagtgtctgg gtttgtgttc ccctagaagc agaccctgaa    24121
acagtgattc tagggaggtg tccccgggaa tgatcagtag gggggtggag ccatgagaag    24181
ggacagaagt catgccagtt accccatgg  gcatcaggmg cccaaccctc atggggcatt    24241 ctgcggggt  gtagatggaa cacagaacac agcactctca cagccacggc acaaggatgc    24301
tgtgtgttta tccatcagct ccctgtctgt cactggttga gggctgcttc tgggcttgtt    24361
aactctgtgg ctcttccaat ttgccttcca cacagttcaa gagagcacac ttccctcacc    24421
accccagaca cagaaatcct caagcagaaa agctggaagt ggggaaacca ggtgggactc    24481
aacttgctat cactgaagtg aagagtaatg agttgagaaa tacaaaatga tggcaaataa    24541
ctcaagtcaa tgtgcagtgt ggtgccagaa accacaggca ccaaggaacc caaactaaag    24601
agagtgcaag ggcttcctcg ttgaaatgct gtttgagctg ggtcttgaag gaggagtggg    24661
gttcatcagc agtgagggaa cagcagttta aagggatt  taaacctccg tgaagagtgt    24721
gtcgataaga acacacaagg acttggaatt attgcccaca cttcaggtct ctactgcccg    24781
taaggcccct ggtctgctct cagcctctaa agttcaggct aatttgggca ctttgacatt    24841
ttctgtcctg ccttccag gaa ggg  cga gag ctc acc ctt  gag aag cca gag    24892
             Glu Gly  Arg Glu Leu Thr Leu  Glu Lys Pro Glu
                                                 1340            1345 ctg aaa gcc ctg gtg tcg  gag aag ctg aga gac  ctg cac agg cgc       24937
Leu Lys Ala Leu Val Ser  Glu Lys Leu Arg Asp  Leu His Arg Arg
1350                1355                 1360 tgg gac gag ctg gag acc  acc acc caa gcc aag  gcc cgc agc ctc       24982
Trp Asp Glu Leu Glu Thr  Thr Thr Gln Ala Lys  Ala Arg Ser Leu
1365                1370                 1375 ttt gat gcc aac cga gct  gag ctg ttt gcc cag  agc tgc tgt gcc       25027
Phe Asp Ala Asn Arg Ala  Glu Leu Phe Ala Gln  Ser Cys Cys Ala
1380                1385                 1390 ctg gag agc tgg ctg gag  agc ctg cag gcc cag  ctg cac tcg gat       25072
Leu Glu Ser Trp Leu Glu  Ser Leu Gln Ala Gln  Leu His Ser Asp
1395                1400                 1405 gac tac ggc aag gac ctc  acc agc gtc aac atc  ctg ctc aag aag       25117
Asp Tyr Gly Lys Asp Leu  Thr Ser Val Asn Ile  Leu Leu Lys Lys
1410                1415                 1420 cag cag gtgtgctgtg ggcctttgat ggggatggtg aacagcagaa gaaagggggct      25173
Gln Gln
1425 gcagctttca agatttggga ggccagctga ggcctggcag ataacacctt cactagcatt    25233 tcccagagtc atttctttgg gcagccagta tcagaatctc tagggatatg tcgcagtcag    25293 ggttagagtt aggagacaga ccccctaata atttgacgat gagaacttca gtaaaaagaa    25353 atattaatta ggccaggcac agtggctcat gcctgtaatc tcagcacttt gggaggccaa    25413 ggcaggcagg tcgcttgagg tcaggagttc aagaccagcc tggccaacat ggtgaaaccc    25473 cgtctctact aaaaatacaa aaattagcca ggcgtggtgg cgcacgcctg ttatcccagc    25533 tacttgggag gctgagggct gaggaggag  atagcttga  acccaggaga cagaggttgc    25593 agtgagccgt gatcatgcca tcgcactcca gcctgggcaa gcctctgtct caaaaaaaaa    25653 aacagaagta taaattagta aaaggtggta agagaactc  tatagcaggg gtcagaaaac    25713 ttttttcagt aaagcaccag atagtaaatt tttggggctt catgggtcgt aaggtctatg    25773 tcacagccct tcaactctgc ccttgtaagg aaaagcagct gcggattata tgtaaaataa    25833
```

```
ggggtatggc caggtgtggt ggctcacaca tgtaatccca cactttggg aggccgaggt    25893 ggccggatca cttgagtcca ggagttttga gactagcctg gcaacatgg caaaacccca    25953 tctctacaaa aactacaaaa attagctggg cgtggtggtg gtgtgtgcct gtagtcccag    26013
ctactcagga ggctgaggtg agaagattgt ttgagcctgg agagtcgagg ctgcagtggg    26073
ctgtgatcgt gccactgcac tgcagcctgg gtggcagagc gagacttgtc tcaaaaaatt    26133
ttttaaaaag gggtgcagct gtggtccaat aaaaacttta taaggctagg cagtgggctg    26193
gacttgctgg tccctgctct gaagaatgca gaatgggaag tgtagggagc agctgacacc    26253
tctggggttg aggagtcccc caggaaggag caagatggct gagtctcaga cctccttgga    26313
gagggcggag gcccactgaa tggcctggaa atttgctggg gtatcacagg ccagagcatg    26373
tctgaagcca gcaagccaag gctggccagc aggaagtggc cactagagtg cagcaaaact    26433
tgccagagag taagagccac cggatctctt gcgcactgtg gacagttttg ctgtaggagg    26493
aagaaaagca ccttggaacc gtggaatgcc ccacatctgc taggcattgt ggtgtccctc    26553
cagcgccctc tgctgacaag gcctagattg tgcctgctgg caaaggagga atgtttccag    26613
gggccagttc cagtgtctca aagcagggcc acgatggatt ggggatggag agacaatgaa    26673
ttgataatgg gcacagttat cacactaccc tggatttttt aatttcaatc ttttagattc    26733
gcgggtgtgg gtgcaggttt gttataagtt atattgtgtg atgctgaagt ttggggtgta    26793
attgaaccca tcaccatgt agtgagcaca gtacccaata gggattttt caacccctgc    26853 ccttggattc ttgtgcatat aaagttcgag atccactgat ccagcccatg aggggatgct    26913
ctccctgggt gagctgcagt gatgagcagc cacagtgggc tggatagaga ctggttggtg    26973
tctctgctgg gcatgaaggc ggaaatgcag agctaacatg tccttcctcc tggcggtttg    27033
```

| cag atg ctg gaa tgg gag atg gct gtg aga gag aag gag gtg gag | 27078 |
| Met Leu Glu Trp Glu Met Ala Val Arg Glu Lys Glu Val Glu | |
|     1430          1435             1440 | |

| gca atc cag gcc cag gyc aaa gca ctg gcc cag gag gac cag ggt | 27123 |
| Ala Ile Gln Ala Gln Xaa Lys Ala Leu Ala Gln Glu Asp Gln Gly | |
|     1445          1450             1455 | |

| gca ggg gag gtg gag aga acc tcg agg gcc gtg gag gag aag ttc | 27168 |
| Ala Gly Glu Val Glu Arg Thr Ser Arg Ala Val Glu Glu Lys Phe | |
|     1460          1465             1470 | |

| agg gcc ttg tgc cag ccc atg cgg gaa cgc tgc cgg cgc ctg cag | 27213 |
| Arg Ala Leu Cys Gln Pro Met Arg Glu Arg Cys Arg Arg Leu Gln | |
|     1475          1480             1485 | |

| gct tct cgc gag cag cac cag ttc cac cgc gat gtg gaa gat gag | 27258 |
| Ala Ser Arg Glu Gln His Gln Phe His Arg Asp Val Glu Asp Glu | |
|     1490          1495             1500 | |

| att gtgagtcact ggggccaagg acggcaagct gcccccagcc atgtggttct | 27311 |
| Ile | |

```
ccagcctccc tcctggatgc cagggagatg ccagcagggc tctattccct cttctctttg    27371
gcattgacca tctcccctat agggagactt ggagatgcct cccagaacca gagatgactg    27431
ttccccacac acagggcggt agccccaggt gtccccactc ccactaatca gtccctgctg    27491
cttgccttgc cctctgggcc tccactgacc ccctcttcct cttccag ttg tgg gtg     27547
                                                      Leu Trp Val
```

| aca gag cgg ctg ccc atg gcc agc tcc atg gag cat ggc aag gac | 27592 |
| Thr Glu Arg Leu Pro Met Ala Ser Ser Met Glu His Gly Lys Asp | |
| 1505          1510             1515 | |

| ctg ccc agc gtc cag ctt ctc atg aag aaa aac cag gtgaggcaga | 27638 |
| Leu Pro Ser Val Gln Leu Leu Met Lys Lys Asn Gln | |

```
                      1520              1525              1530
ggctgaaggc aaaagagaag ttcccaggag cctgcccaga cttggacgtg ttttttctta     27698
agaccaggcc cccctcgatg ctgagtgtaa ccctggactt cagtggctgt ctttcctcac     27758
cttgggaggg tgggtcctct cagtaggaga tagtggggc tgggcggctg acgggtgtta     27818
ccatcgcacc cccaggctag gagagggagc agaggaccca ggaaggagag aggcacaggg     27878
gtgaagggtg gtctccggga gcacgtgggg ctggggcagg actttcagca ttttctcttc     27938
tgtggccatg ggcag acc ctg cag aaa gag att cag ggc cat gag ccc          27986
                Thr Leu Gln Lys Glu Ile Gln Gly His Glu Pro
                                1535              1540 cgg atc gcg gac ctg agg gag cgg cag cgt gct cta ggt gca gca           28031
Arg Ile Ala Asp Leu Arg Glu Arg Gln Arg Ala Leu Gly Ala Ala
        1545              1550              1555 gca gca ggt cca gag ctg gct gag ctg cag gaa atg tgg aaa cgc           28076
Ala Ala Gly Pro Glu Leu Ala Glu Leu Gln Glu Met Trp Lys Arg
    1560              1565              1570 ctg ggc cac gag ctg gaa ctt cga ggg aag cga ctg gag gat gcc           28121
Leu Gly His Glu Leu Glu Leu Arg Gly Lys Arg Leu Glu Asp Ala
    1575              1580              1585 ctg cga gcc cag cag ttc tac cgc gat gcc gcc gag gcg gag gcc           28166
Leu Arg Ala Gln Gln Phe Tyr Arg Asp Ala Ala Glu Ala Glu Ala
    1590              1595              1600 tgg atg ggc gag cag gaa tta cac atg atg ggc cag gag aag gcc           28211
Trp Met Gly Glu Gln Glu Leu His Met Met Gly Gln Glu Lys Ala
    1605              1610              1615 aag gtgagggcca ggacagagcc cagtgtatgt gaccagttct gccctcccct            28264
Lys gacctgatgc tggatgccac tgtcccttcc cccag gat gag ctg agt gcc cag        28317
                                      Asp Glu Leu Ser Ala Gln
                                                  1620 gca gag gtg aag aag cac cag gtg ctr gag caa gcc ctg gcc gac           28362
Ala Glu Val Lys Lys His Gln Val Leu Glu Gln Ala Leu Ala Asp
1625              1630              1635 tac gcg cag acc atc cac cag ctg gcg gcc agc agc cag gac atg           28407
Tyr Ala Gln Thr Ile His Gln Leu Ala Ala Ser Ser Gln Asp Met
1640              1645              1650 att gac cac gag cac cca gag ag gtgggtgcag yggcagcccg                  28450
Ile Asp His Glu His Pro Glu Ser
1655              1660 gcccagcctg ggggtggagc cggctgcagg aacaggaagg tgcagggaat gtggagcctt     28510
cagtgctgtg tgcacggagc cttctagaaa gctggaacac agggtgggcg agctgttggg     28570
agactcagag ggacagggct ccacagaaca gaccggaggt cagagctaca cccctaagtc     28630
ccacagtgcc tccctcactc ttcttgcag c act cgg ata tcc atc cgc caa         28681
                                  Thr Arg Ile Ser Ile Arg Gln
                                                  1665 gcc cag gtg gac aag ctg tat gcc ggc ctg aag gag ctg gct gga           28726
Ala Gln Val Asp Lys Leu Tyr Ala Gly Leu Lys Glu Leu Ala Gly
1670              1675              1680 gag cgg cgg gag cgc ctg cag gag cac ctc cgg ctg tgc cag ctc           28771
Glu Arg Arg Glu Arg Leu Gln Glu His Leu Arg Leu Cys Gln Leu
1685              1690              1695 cgc cgc gag ctg gat gac ctg gaa cag tgg atc cag gag cgc gag           28816
Arg Arg Glu Leu Asp Asp Leu Glu Gln Trp Ile Gln Glu Arg Glu
1700              1705              1710 gtg gtg gcg gcc tcc cac gag ctg ggc cag gac tac gag cat gtg           28861
Val Val Ala Ala Ser His Glu Leu Gly Gln Asp Tyr Glu His Val
```

-continued

| | | | |
|---|---|---|---|
| 1715 | 1720 | 1725 | |
| act gtgagtgtag ggagggcacc cagctcagat caaccgtggg aagagtggag<br>Thr<br>1730 | | | 28914 |
| gacccacagg gagactagga cctagtccca ggcagagcac tgagggcta agggcaaga | | | 28974 |
| ccaggctgag caggcactgt cctcctggtt ttgaggtata tgatttgaag aggccgggca | | | 29034 |
| taggctcaca cctgtaatcc tagcaccttg ggaggctgag atgggaggat tgcttgagtc | | | 29094 |
| caggagttca agaccagcct gggcaacata gtgagaccc ccatctctac aaaaaaaatt | | | 29154 |
| tttttttatt agccaggcac agccgtgcat gcctgtaggc ccaactactt aggaggctga | | | 29214 |
| ggtgggagga tctcttgagc ctgggaggtc gacactgcag tgattgcgct agtgcactcc | | | 29274 |
| agagcaagac cctatcatct ctaaatacat acacacacac acaatttgaa gaattgtaca | | | 29334 |
| gaaaggggac atgaagctga gctgagacaa gggcaaacag gaaattatca ctcacctttt | | | 29394 |
| tcaacagaat tcaacaaaac ggagtatgat ccaccccccc gacagtttgg gggcttggac | | | 29454 |
| cctcagtcgt acagaaatat ggaccatagt tagggtatcc ttgtctgaag cctaagggtc | | | 29514 |
| ccaagcacct tgaaacgcct ttgctggggg tggagggagt ctgtcaaata cagggtcagt | | | 29574 |
| gggaagcagc tgcacctact ccttaaccac agggaagaaa cctgtcccgg ccccatgca | | | 29634 |
| gcggggagag gtgggttctg agtttggagt ggaggactcg ctccatcagg cagggaccac | | | 29694 |
| atcccctaac atcacggcat ggtctgtcca tctgcttcct ctaccag atg ctc cga<br>Met Leu Arg | | | 29750 |
| gac aaa ttc cga gag ttc tcc cgg gac aca agc acc atc ggt cag<br>Asp Lys Phe Arg Glu Phe Ser Arg Asp Thr Ser Thr Ile Gly Gln<br>1735 1740 1745 | | | 29795 |
| gag cgc gta gat agc gcc aat gcg ctg gcc aat ggg ctc att gct<br>Glu Arg Val Asp Ser Ala Asn Ala Leu Ala Asn Gly Leu Ile Ala<br>1750 1755 1760 | | | 29840 |
| ggg ggc cat gct gca cgg gcc acc gtg gcc gag tgg aag gac agt<br>Gly Gly His Ala Ala Arg Ala Thr Val Ala Glu Trp Lys Asp Ser<br>1765 1770 1775 | | | 29885 |
| ctc aay gag gcc tgg gct gac ctg ctt gag ctg ctg gac aca cgg<br>Leu Asn Glu Ala Trp Ala Asp Leu Leu Glu Leu Leu Asp Thr Arg<br>1780 1785 1790 | | | 29930 |
| ggt cag gtg ctg gcc gcg gcg tac gag ctg cag cgc ttc ctg cac<br>Gly Gln Val Leu Ala Ala Ala Tyr Glu Leu Gln Arg Phe Leu His<br>1795 1800 1805 | | | 29975 |
| ggg gca cgc caa gcc ctg gcg cgg gtg cag cac aag cag cag cag<br>Gly Ala Arg Gln Ala Leu Ala Arg Val Gln His Lys Gln Gln Gln<br>1810 1815 1820 | | | 30020 |
| ctt ccg gac ggg act ggc cgc gac ctc aac gct gcc gag gcc ctg<br>Leu Pro Asp Gly Thr Gly Arg Asp Leu Asn Ala Ala Glu Ala Leu<br>1825 1830 1835 | | | 30065 |
| cag cgc cga cac tgt gcc tac gag cat gac att cag gcc ctc agc<br>Gln Arg Arg His Cys Ala Tyr Glu His Asp Ile Gln Ala Leu Ser<br>1840 1845 1850 | | | 30110 |
| ccc cag gtctgaccca agcatgagga ggtgggggag cttagagga ggccatgggg<br>Pro Gln<br>1855 | | | 30166 |
| gaaatgccrg ggagagttcc caggagctag ggtagagctc agaaatgctg ggaggacggc | | | 30226 |
| actctttcga gggccatttc gagatgagga aattgctcca agaaaacatc tctgtttggc | | | 30286 |
| caggcgcggt ggctctcgcc tgtaatccca gcactttggg aggccgagga gggcggatca | | | 30346 |
| tctgagattg ggagttcgag accagcctga ccaacatgga gaaacccctt ctctactaaa | | | 30406 |

```
aatacaaaat tagccaggca tggtggcgca tgcctgtaat cctagctact caggaggctg   30466
aggcaggaga atcacttgaa cccaggaggc ggaggttgca gtgagctgag atccctccac   30526
tgcactccag cctgggcaac aagagcgaaa ctccgtctca aaaagaaaga aaacatctct   30586 ggcagggac atctagccac tgcattcaca cttttgatga caagcccct tgagagccca    30646 tgatgtcttc aggggttccc agtggccagg agactcttca tgctgcgcta aatcagcctg   30706
ttagtgcttc ccaggcttga gctctaggct cacactcagt aagcatggat ccttccttca   30766
accactagaa cccatcagcc cctgcctgaa tccccttttc aggctaagta gcacgttcta   30826
gcaatctcca aggtctatca catcctagac aggcctctga agttcaact ggccaatggc    30886 tcttttccag atcctccccc agttaagccc aggtgtctag atgagaccca acagggcaga   30946
gtgtggccag cccctgcctt catctttccc agcacccca ctccctggct cctcccctg    31006 cttctttggt gtgagacagg caggaggtga gagtggcagc caggactgag gcaggctgcg   31066
```
gctccttgga gtccccgct ctgcctgact ctgacccggg gctccgcag gtc cag cag   31124
                                                                                         Val Gln Gln gtg cag gac gac ggc cac cgg ctc cag aag gcc tac gct gga gac   31169
Val Gln Asp Asp Gly His Arg Leu Gln Lys Ala Tyr Ala Gly Asp
   1860                   1865                  1870 aag gct gag gag atc ggc cgc cac atg cag gcc gtg gcc gag gcc   31214
Lys Ala Glu Glu Ile Gly Arg His Met Gln Ala Val Ala Glu Ala
  1875               1880                 1885 tgg gcc cag ctt cag gga agc tct gcc gcc cgc cgg cag ctg ctg   31259
Trp Ala Gln Leu Gln Gly Ser Ser Ala Ala Arg Arg Gln Leu Leu
  1890               1895                 1900 ctg gac acc aca gac aag ttc cgc ttc ttc aag gct gtc cgg gaa   31304
Leu Asp Thr Thr Asp Lys Phe Arg Phe Phe Lys Ala Val Arg Glu
  1905               1910                 1915 ctg atg ctc tgg atg gat gag gtc aac ctg cag atg gat gcc cag   31349
Leu Met Leu Trp Met Asp Glu Val Asn Leu Gln Met Asp Ala Gln
  1920               1925                 1930 gag cgt ccc cg gtgagaatcc cagggctcag ggcctccacg ggttgtgtgg   31400
Glu Arg Pro Arg
  1935 ctgggctgtg atggggctgt gggcagcagg tgatgctgtt tctgcctccc cccag g     31456 gat gtg tcc tcc gcg gat cta gtc atc aag aac cag caa ggc atc   31501
Asp Val Ser Ser Ala Asp Leu Val Ile Lys Asn Gln Gln Gly Ile
        1940               1945                 1950 aag gca gag ata gag gcc cgg gca gac cgc ttc tcc tcc tgc atc   31546
Lys Ala Glu Ile Glu Ala Arg Ala Asp Arg Phe Ser Ser Cys Ile
        1955               1960                 1965 gac atg ggg aag gag ctg ctg gcc agg agc cac tat gcg gcc gag   31591
Asp Met Gly Lys Glu Leu Leu Ala Arg Ser His Tyr Ala Ala Glu
        1970               1975                 1980 gag gtgggtgagg cctggtggc cgggccattc tcactgtgca gtgctgaacg    31644
Glu

```
ctgacttctt ggtggctttc tgcttcctct cattctctct ttgcaagaaa cctttcattc   31704
tctcccctca gtgccattca cgggtttctc gcattctgga aatctctccc cagaaccgtc   31764
tgcctcttga catcagaaat cactggtcct gggccaggca tggtggctca cgcctgtaat   31824
cccagcactt tgggaggccc aggcgggcag atcacctgag gtcacgagtt cgagaccagc   31884
ctggcctcca tggttgtgt ggctgggctg tgatgaaaca tggtgaaacc ccrtttccac    31944
taaaaacaca aaaattagcc gggcgtggtg gcgggcacct gtaatcccag ctactcgag    32004 gctgaggcag gagaattgct tgaacctggg aggtggaggt tgcagtgagc tgagattgcg   32064
```

```
ccactgcatt ccagccttgg tgataagagc gaaactccgt ctcaaaaaaa agaaagaaag      32124
aaagaaatca cctgtccccc tggatgactc ccaggggcc gtggaaagat ctcacatcct       32184
ggtgctaact catatctctg cccccccgccc ccag atc tca  gag aag ctg tct       32236
                                      Ile Ser  Glu Lys Leu Ser
                                                1985 cag ctg cag gca cgg cgc  cag gag aca gct gag  aag tgg cag gag         32281
Gln Leu Gln Ala Arg Arg  Gln Glu Thr Ala Glu  Lys Trp Gln Glu
1990            1995                     2000 aag atg gac tgg ctt cag  ctg g gtgagctgcc aagggggccc caggccctgt        32333
Lys Met Asp Trp Leu Gln  Leu
2005                2010 ggggagtggg gggcatcctg caccctgtgg gttccagagt aggtgagact aggaaccctg      32393
ggtgtgaaac tcacgatgcc caatcttcgt gctgcctggc acagtctggg ggcagtggct     32453
ttctctgtgt ccctgttctt gaggttgccr tggccactgt gccctgccag tggccactct     32513
gacccaccat cttcctgcaa ccccygatcc tgccag tt   ttg gag gtg    ctt gtg   32566
                                            Val Leu Glu Val  Leu Val
                                                          2015 ttt gga aga  gat gca ggg atg gca  gag gcc tgg ctc tgc agc cag         32611
Phe Gly Arg  Asp Ala Gly Met Ala  Glu Ala Trp Leu Cys Ser Gln
     2020                2025                      2030 gag cca ctg  gtg cgc agc gct gag  ctg ggt tgc acg gtc  gac gaa        32656
Glu Pro Leu  Val Arg Ser Ala Glu  Leu Gly Cys Thr Val  Asp Glu
     2035                2040                      2045 gtt gag agc  ctc atc aag cgg cac  gag gcc ttc cag aag  tca gca        32701
Val Glu Ser  Leu Ile Lys Arg His  Glu Ala Phe Gln Lys  Ser Ala
     2050                2055                      2060 gtg gcc tgg  gag gag cga ttc tgt  gcg ctg gag aag  ctt act gcg        32746
Val Ala Trp  Glu Glu Arg Phe Cys  Ala Leu Glu Lys  Leu Thr Ala
     2065                2070                 2075 gtgagggaca caggacccg gatgcccact ccaacctgct ccctgacct gtgctggctt       32806 ctgcttggrg aagacatgtc ttctctcttc ccactgcacc agtggccccc agatgtgagc      32866
tgagagtgcc attgtcacca caccttaggg aggtgtcagt tccctggggt gatgccgaga     32926
caccttctcc cgctttgttt cttgtcccca ccatcttctc aaattctgtt ctcctcttat     32986
catatttcat caaattagag ttgagacatt tcagctctcc ctgtttccct ggccctctta     33046
cacgcaacct tctacacgct gaatgcagca ttttttgaca g cta gag gag      cgg    33099
                                             Leu Glu Glu      Arg
                                                           2080 gag aag gag  cga  aag aga aag agg  gag gag gag gag cgg cgg  aaa       33144
Glu Lys Glu  Arg  Lys Arg Lys Arg  Glu Glu Glu Glu Arg Arg  Lys
        2085                2090                     2095 cag ccg cct  gct  ccc gaa ccc aca gcc  agt gtg cct cca ggg    gac     33189
Gln Pro Pro  Ala  Pro Glu Pro Thr Ala  Ser Val Pro Pro Gly    Asp
        2100                2105                        2110 ctg gtg ggc  ggc  cag aca gct tct gac  acc acc tgg gac gg             33230
Leu Val Gly  Gly  Gln Thr Ala Ser Asp  Thr Thr Trp Asp Gly
        2115                2120                     2125 gtgagagcca ggatgcctgg gtaggaggag gcggctgagc ccaggccacc cagggactaa     33290
tgattctgtg ttgcctttgg tcatcccag a acc cag cca cgg cca     cca cca    33341
                                  Thr Gln Pro Arg Pro     Pro Pro
                                                     2130 tcc aca caa  gca ccc agt gtt aat  gga gtc tgc aca gat   gga gag       33386
Ser Thr Gln  Ala Pro Ser Val Asn  Gly Val Cys Thr Asp   Gly Glu
        2135                2140                     2145
```

```
ccc tca cag  gtgacccac tgtccctctg tgcccccatc ggagtcgtag           33435
Pro Ser Gln
        2150 cccctccacc cccgcacatc cttttacaga ttcttgtcct tgcag ccc ctg ctg gga 33492
                                                  Pro Leu Leu Gly caa cag aga ctt gag cac agc agc ttc ccc gaa  ggg ccg gtgagttccc  33541
Gln Gln Arg Leu Glu His Ser Ser Phe Pro Glu  Gly Pro
2155                    2160                 2165 ctgcaagtgt ggtgttgata actgtgaggc gaagggtcca gaggggtgg tgagtgcggg  33601 tgggggagta ctggggatgg gatgggagag ggcagaggct cacaggcagc ttgggggcag  33661
gaagaccaac tcctggacac ggagcttcct ggcacccagg ttagggatct cccgtctcaa  33721
cctttgacac tgacactgat tccccccag gga cct ggc  tca ggg gac gaa      33772
                                 Gly Pro Gly Ser Gly Asp Glu
                                                 2170 gcc aat ggg ccc cgg gga gag agg cag acc cgg  act cgg ggc ccg      33817
Ala Asn Gly Pro Arg Gly Glu Arg Gln Thr Arg  Thr Arg Gly Pro
2175                2180                     2185 gcc cca tct gca atg ccc cag agc agg tct acc  gag tca gcc cat      33862
Ala Pro Ser Ala Met Pro Gln Ser Arg Ser Thr  Glu Ser Ala His
2190                2195                     2200 gct gcc acc ctg ccg cct cga ggc cca gag cca  tct gcc cag gag      33907
Ala Ala Thr Leu Pro Pro Arg Gly Pro Glu Pro  Ser Ala Gln Glu
2205                2210                     2215 cag atg gag ggg atg ctg tgc cgc aag cag gag  atg gag gcc ttc      33952
Gln Met Glu Gly Met Leu Cys Arg Lys Gln Glu  Met Glu Ala Phe
2220                2225                     2230 ggg aag aag gct gcc aac ag  gtacagcctc tctggagcct gctctcagag      34002
Gly Lys Lys Ala Ala Asn Arg
2235                2240 ggcacttccc cagagcctct gcccagatag agggagggat gcccttaga gtacatcttc   34062 tgggcaaagg gtaggacttg ggaccagagc ggggcctcag ggaggacca gagggtgtga   34122 agaccgtggc ctaaagatgg gagcagaact ggaagtccta ggacacccaa gagggctcca   34182
ggttgcgggc gccactgagg ccggccagtc agcaccgcgt ccctcgcag g tcc tgg    34238
                                                       Ser Trp cag aac gtg tac tgt gtc ctg cgg cgt ggg agc ctc  ggc ttt tac      34283
Gln Asn Val Tyr Cys Val Leu Arg Arg Gly Ser Leu  Gly Phe Tyr
        2245                2250                 2255 aag gat gcc aag gca gcc agc gcg gga gtg cca tac  cac gga gaa      34328
Lys Asp Ala Lys Ala Ala Ser Ala Gly Val Pro Tyr  His Gly Glu
2260                2265                         2270 gtg cct gtc agc ctg gcc agg gcc cag ggc agc gtc  gcc ttt gat      34373
Val Pro Val Ser Leu Ala Arg Ala Gln Gly Ser Val  Ala Phe Asp
2275                2280                         2285 tac cga aag cgc aaa cat gtc ttc aag ctg gg gtaggaacag             34415
Tyr Arg Lys Arg Lys His Val Phe Lys Leu Gly
2290                2295 ggaacagtgc tctcgggatg ggaggagagt tgggagtgac acaggtgagc catgagtcag   34475
gtccagaggg aggggagttc ctgtaaggag cctgagtgga gtaaccaggc cagccacttg   34535
gggatagtgt agatgaggga ggcggagatt ctggttgtct ccacaccaag gggagcagga   34595
gaaccaagac ccaggcctga cggctgccaa tgtcaaggtg aaaaattacc cagggtggga   34655
aatccaaagg tagggatctg ggaagacctc caggggcctg tccctgcctg ccagcaagca   34715 gccgagcag gaggccgggg ctggggtgga agtgagctcc ccctgcctct ggggccagtc   34775
agaaaggatg tgcttctgca cagtctgggg aagctgaaga atgtgcagag cgtgtctggt   34835
```

```
ccggctctga gggctgcagc cagatgtccc agcctggtgt tgggtcatga ttacgctctc   34895
accagcagct acctggcaga tccggattct cagctctgcc ctgtggcctc tctctcccaa   34955 cag c tta cag gat gga aaa gaa tat tta ttc cag gcc aag gat gag       35001
    Leu Gln Asp Gly Lys Glu Tyr Leu Phe Gln Ala Lys Asp Glu
        2300            2305                2310 gtgagctgtc cttcgtgttc ctctctgtcc gtgccattcc agaagcttcc agctgcagac   35061
tccccttctt tccctgtcct ccctcttttt cctggtcttg tcctttgtgg taagactgga   35121
tgtgtgcgac ggccgcacca ggccgcactc cctgtctaag ccggccacat tctcctaata   35181
gcatgaaaca gtcagctcac tttctgcctc ctcctcttac acttccctgc tgtccactgc   35241
ggccaactca gcacagtgtc cttgaagctg attgagggtc tttccatcca cag gca      35297
                                                            Ala gag atg agc tcg tgg cta cgg gtg gtg aat gca gcc att gcc aca         35342
Glu Met Ser Ser Trp Leu Arg Val Val Asn Ala Ala Ile Ala Thr
2315            2320                2325 gcg tct tct gcc tct gga gag cct gaa gag ccg gtg gtg ccc agc         35387
Ala Ser Ser Ala Ser Gly Glu Pro Glu Glu Pro Val Val Pro Ser
2330            2335                2340 acc acc cgg ggc atg acc cgg gcc atg acc atg ccc cca gtg tca         35432
Thr Thr Arg Gly Met Thr Arg Ala Met Thr Met Pro Pro Val Ser
2345            2350                2355 ccc gtc ggg gct gag ggg cct gtt gtg ctc cgc agc aaa gac ggc         35477
Pro Val Gly Ala Glu Gly Pro Val Val Leu Arg Ser Lys Asp Gly
2360            2365                2370 aga gaa cga gag cga gaa aaa cgc ttc agc ttc ttt aag aag aac         35522
Arg Glu Arg Glu Arg Glu Lys Arg Phe Ser Phe Phe Lys Lys Asn
2375            2380                2385 aag tagttggggg caaggtccca ggccaactcc ctccctccgt tcaggaaact           35575
Lys
2390 gccagggaca gtcgacaggg accgccctct tgtcaggaca actgcctgct gctagggtct   35635 gttgccaagg tcaacccatc accaggaact gtcactgggg acgagtccat gttcccaagg   35695 rcagcccttc tcttctgctg tttaattcca gactggtggt gggacccagg taaccccctc   35755 tcccaccccc gccgacttct cccctttccc cagcctcgtg cctctgtccc tcaccacggt   35815 gtggacagtg ccgcaccctc aacataggcc atgtggggag tggctgcccc tgcctcaggg   35875 tcattctcct gccatgygag ggcactcgcc ttctgccttc tggttcctca ccctcagac    35935 cagccaggaa cctctcagag ctgaagcagg ccctggggga agaagtgcca gatgacagtc   35995 agaggcgcag gagccctccc tccccacccc caccctgtaa ctccagctgc cactccatct   36055 ccagytgctc tcaatggctt ccaggtgtgt tgtycgggga cagccaccgc cttgagtctg   36115 gccaaggagg tgattaaaca gctcagcttc tc                                 36147
```

<210> SEQ ID NO 2
<211> LENGTH: 2390
<212> TYPE: PRT
<213> ORGANISM: Homo sapiens
<220> FEATURE:
<221> NAME/KEY: MOD_RES
<222> LOCATION: (825)
<223> OTHER INFORMATION: Gly or Ser
<220> FEATURE:
<221> NAME/KEY: MOD_RES
<222> LOCATION: (1034)
<223> OTHER INFORMATION: Ala or Val
<220> FEATURE:
<221> NAME/KEY: MOD_RES

```
<222> LOCATION: (1446)
<223> OTHER INFORMATION: Ala or Val

<400> SEQUENCE: 2
```

| | | | | | | | | | | | | | | |
|---|---|---|---|---|---|---|---|---|---|---|---|---|---|---|
|Met|Ser|Ser|Thr|Leu|Ser|Pro|Thr|Asp|Phe|Asp|Ser|Leu|Glu|Ile|Gln
|1| | | |5| | | | |10| | | | |15|

Gly Gln Tyr Ser Asp Ile Asn Asn Arg Trp Asp Leu Pro Asp Ser Asp
            20                  25                  30

Trp Asp Asn Asp Ser Ser Ser Ala Arg Leu Phe Glu Arg Ser Arg Ile
            35                  40                  45

Lys Ala Leu Ala Asp Glu Arg Glu Ala Val Gln Lys Lys Thr Phe Thr
 50                      55                  60

Lys Trp Val Asn Ser His Leu Ala Arg Val Thr Cys Arg Val Gly Asp
 65                  70                  75                  80

Leu Tyr Ser Asp Leu Arg Asp Gly Arg Asn Leu Leu Arg Leu Leu Glu
                85                  90                  95

Val Leu Ser Gly Glu Ile Leu Pro Lys Pro Thr Lys Gly Arg Met Arg
                100                 105                 110

Ile His Cys Leu Glu Asn Val Asp Lys Ala Leu Gln Phe Leu Lys Glu
            115                 120                 125

Gln Lys Val His Leu Glu Asn Met Gly Ser His Asp Ile Val Asp Gly
130                 135                 140

Asn His Arg Leu Thr Leu Gly Leu Val Trp Thr Ile Ile Leu Arg Phe
145                 150                 155                 160

Gln Ile Gln Asp Ile Ser Val Glu Thr Glu Asp Asn Lys Glu Lys Lys
                165                 170                 175

Ser Ala Lys Asp Ala Leu Leu Leu Trp Cys Gln Met Lys Thr Ala Gly
                180                 185                 190

Tyr Pro Asn Val Asn Val His Asn Phe Thr Thr Ser Trp Arg Asp Gly
                195                 200                 205

Leu Ala Phe Asn Ala Ile Val His Lys His Arg Pro Asp Leu Leu Asp
210                 215                 220

Phe Glu Ser Leu Lys Lys Cys Asn Ala His Tyr Asn Leu Gln Asn Ala
225                 230                 235                 240

Phe Asn Leu Ala Glu Lys Glu Leu Gly Leu Thr Lys Leu Leu Asp Pro
                245                 250                 255

Glu Asp Val Asn Val Asp Gln Pro Asp Glu Lys Ser Ile Ile Thr Tyr
                260                 265                 270

Val Ala Thr Tyr Tyr His Tyr Phe Ser Lys Met Lys Ala Leu Ala Val
                275                 280                 285

Glu Gly Lys Arg Ile Gly Lys Val Leu Asp His Ala Met Glu Ala Glu
                290                 295                 300

Arg Leu Val Glu Lys Tyr Glu Ser Leu Ala Ser Glu Leu Leu Gln Trp
305                 310                 315                 320

Ile Glu Gln Thr Ile Val Thr Leu Asn Asp Arg Gln Leu Ala Asn Ser
                325                 330                 335

Leu Ser Gly Val Gln Asn Gln Leu Gln Ser Phe Asn Ser Tyr Arg Thr
                340                 345                 350

Val Glu Lys Pro Pro Lys Phe Thr Glu Lys Gly Asn Leu Glu Val Leu
                355                 360                 365

Leu Phe Thr Ile Gln Ser Lys Leu Arg Ala Asn Asn Gln Lys Val Tyr
                370                 375                 380

Thr Pro Arg Glu Gly Arg Leu Ile Ser Asp Ile Asn Lys Ala Trp Glu
385                 390                 395                 400

-continued

Arg Leu Glu Lys Ala Glu His Glu Arg Glu Leu Ala Leu Arg Thr Glu
            405                 410                 415
Leu Ile Arg Gln Glu Lys Leu Glu Gln Leu Ala Ala Arg Phe Asp Arg
        420                 425                 430
Lys Ala Ala Met Arg Glu Thr Trp Leu Ser Glu Asn Gln Arg Leu Val
        435                 440                 445
Ser Gln Asp Asn Phe Gly Leu Glu Leu Ala Ala Val Glu Ala Ala Val
    450                 455                 460
Arg Lys His Glu Ala Ile Glu Thr Asp Ile Val Ala Tyr Ser Gly Arg
465                 470                 475                 480
Val Gln Ala Val Asp Ala Val Ala Ala Glu Leu Ala Ala Glu Arg Tyr
                485                 490                 495
His Asp Ile Lys Arg Ile Ala Ala Arg Gln His Asn Val Ala Arg Leu
            500                 505                 510
Trp Asp Phe Leu Arg Gln Met Val Ala Ala Arg Arg Glu Arg Leu Leu
        515                 520                 525
Leu Asn Leu Glu Leu Gln Lys Val Phe Gln Asp Leu Leu Tyr Leu Met
    530                 535                 540
Asp Trp Met Glu Glu Met Lys Gly Arg Leu Gln Ser Gln Asp Leu Gly
545                 550                 555                 560
Arg His Leu Ala Gly Val Glu Asp Leu Leu Gln Leu His Glu Leu Val
                565                 570                 575
Glu Ala Asp Ile Ala Val Gln Ala Glu Arg Val Arg Ala Val Ser Ala
            580                 585                 590
Ser Ala Leu Arg Phe Cys Asn Pro Gly Lys Glu Tyr Arg Pro Cys Asp
        595                 600                 605
Pro Gln Leu Val Ser Glu Arg Val Ala Lys Leu Glu Gln Ser Tyr Glu
    610                 615                 620
Ala Leu Cys Glu Leu Ala Ala Ala Arg Arg Ala Arg Leu Glu Glu Ser
625                 630                 635                 640
Arg Arg Leu Trp Arg Phe Leu Trp Glu Val Gly Glu Ala Glu Ala Trp
                645                 650                 655
Val Arg Glu Gln Gln His Leu Leu Ala Ser Ala Asp Thr Gly Arg Asp
            660                 665                 670
Leu Thr Gly Ala Leu Arg Leu Leu Asn Lys His Thr Ala Leu Arg Gly
        675                 680                 685
Glu Met Ser Gly Arg Leu Gly Pro Leu Lys Leu Thr Leu Glu Gln Gly
    690                 695                 700
Gln Gln Leu Val Ala Glu Gly His Pro Gly Ala Ser Gln Ala Ser Ala
705                 710                 715                 720
Arg Ala Ala Glu Leu Gln Ala Gln Trp Glu Arg Leu Glu Ala Leu Ala
                725                 730                 735
Glu Glu Arg Ala Gln Arg Leu Ala Gln Ala Ala Ser Leu Tyr Gln Phe
            740                 745                 750
Gln Ala Asp Ala Asn Asp Met Glu Ala Trp Leu Val Asp Ala Leu Arg
        755                 760                 765
Leu Val Ser Ser Pro Glu Leu Gly His Asp Glu Phe Ser Thr Gln Ala
    770                 775                 780
Leu Ala Arg Gln His Arg Ala Leu Glu Glu Glu Ile Arg Ser His Arg
785                 790                 795                 800
Pro Thr Leu Asp Ala Leu Arg Glu Gln Ala Ala Leu Pro Pro Thr
                805                 810                 815

```
Leu Ser Arg Thr Pro Glu Val Gln Xaa Arg Val Pro Thr Leu Glu Arg
            820                 825                 830

His Tyr Glu Glu Leu Gln Ala Arg Ala Gly Glu Arg Ala Arg Ala Leu
        835                 840                 845

Glu Ala Ala Leu Ala Leu Tyr Thr Met Leu Ser Glu Ala Gly Ala Cys
    850                 855                 860

Gly Leu Trp Val Glu Glu Lys Glu Gln Trp Leu Asn Gly Leu Ala Leu
865                 870                 875                 880

Pro Glu Arg Leu Glu Asp Leu Glu Val Val Gln Gln Arg Phe Glu Thr
            885                 890                 895

Leu Glu Pro Glu Met Asn Thr Leu Ala Ala Gln Ile Thr Ala Val Asn
        900                 905                 910

Asp Ile Ala Glu Gln Leu Leu Lys Ala Asn Pro Pro Gly Lys Asp Arg
    915                 920                 925

Ile Val Asn Thr Gln Glu Gln Leu Asn His Arg Trp Gln Gln Phe Arg
930                 935                 940

Arg Leu Ala Asp Gly Lys Lys Ala Ala Leu Thr Ser Ala Leu Ser Ile
945                 950                 955                 960

Gln Asn Tyr His Leu Glu Cys Thr Glu Thr Gln Ala Trp Met Arg Glu
            965                 970                 975

Lys Thr Lys Val Ile Glu Ser Thr Gln Gly Leu Gly Asn Asp Leu Ala
        980                 985                 990

Gly Val Leu Ala Leu Gln Arg Lys Leu Ala Gly Thr Glu Arg Asp Leu
    995                 1000                1005

Glu Ala Ile Ala Ala Arg Val Gly Glu Leu Thr Arg Glu Ala Asn Ala
1010                1015                1020

Leu Ala Ala Gly His Pro Ala Gln Ala Xaa Ala Ile Asn Ala Arg Leu
1025                1030                1035                1040

Arg Glu Val Gln Thr Gly Trp Glu Asp Leu Arg Ala Thr Met Arg Arg
            1045                1050                1055

Arg Glu Glu Ser Leu Gly Glu Ala Arg Arg Leu Gln Asp Phe Leu Arg
        1060                1065                1070

Ser Leu Asp Asp Phe Gln Ala Trp Leu Gly Arg Thr Gln Thr Ala Val
    1075                1080                1085

Ala Ser Glu Glu Gly Pro Ala Thr Leu Pro Glu Ala Glu Ala Leu Leu
    1090                1095                1100

Ala Gln His Ala Ala Leu Arg Gly Glu Val Glu Arg Ala Gln Ser Glu
1105                1110                1115                1120

Tyr Ser Arg Leu Arg Ala Leu Gly Glu Glu Val Thr Arg Asp Gln Ala
            1125                1130                1135

Asp Pro Gln Cys Leu Phe Leu Arg Gln Arg Leu Glu Ala Leu Gly Thr
        1140                1145                1150

Gly Trp Glu Glu Leu Gly Arg Met Trp Glu Ser Arg Gln Gly Arg Leu
    1155                1160                1165

Ala Gln Ala His Gly Phe Gln Gly Phe Leu Arg Asp Ala Arg Gln Ala
1170                1175                1180

Glu Gly Val Leu Ser Ser Gln Glu Tyr Val Leu Ser His Thr Glu Met
1185                1190                1195                1200

Pro Gly Thr Leu Gln Ala Ala Asp Ala Ala Ile Lys Lys Leu Glu Asp
            1205                1210                1215

Phe Met Ser Thr Met Asp Ala Asn Gly Glu Arg Ile His Gly Leu Leu
        1220                1225                1230

Glu Ala Gly Arg Gln Leu Val Ser Glu Gly Asn Ile His Ala Asp Lys
```

-continued

```
            1235                1240                1245
Ile Arg Glu Lys Ala Asp Ser Ile Glu Arg Arg His Lys Lys Asn Gln
    1250                1255                1260
Asp Ala Ala Gln Gln Phe Leu Gly Arg Leu Arg Asp Asn Arg Glu Gln
1265                1270                1275                1280
Gln His Phe Leu Gln Asp Cys His Glu Leu Lys Leu Trp Ile Asp Glu
            1285                1290                1295
Lys Met Leu Thr Ala Gln Asp Val Ser Tyr Asp Glu Ala Arg Asn Leu
        1300                1305                1310
His Thr Lys Trp Gln Lys His Gln Ala Phe Met Ala Glu Leu Ala Ala
    1315                1320                1325
Asn Lys Asp Trp Leu Asp Lys Val Asp Lys Glu Gly Arg Glu Leu Thr
    1330                1335                1340
Leu Glu Lys Pro Glu Leu Lys Ala Leu Val Ser Glu Lys Leu Arg Asp
1345                1350                1355                1360
Leu His Arg Arg Trp Asp Glu Leu Glu Thr Thr Thr Gln Ala Lys Ala
            1365                1370                1375
Arg Ser Leu Phe Asp Ala Asn Arg Ala Glu Leu Phe Ala Gln Ser Cys
        1380                1385                1390
Cys Ala Leu Glu Ser Trp Leu Glu Ser Leu Gln Ala Gln Leu His Ser
    1395                1400                1405
Asp Asp Tyr Gly Lys Asp Leu Thr Ser Val Asn Ile Leu Leu Lys Lys
    1410                1415                1420
Gln Gln Met Leu Glu Trp Glu Met Ala Val Arg Glu Lys Glu Val Glu
1425                1430                1435                1440
Ala Ile Gln Ala Gln Xaa Lys Ala Leu Ala Gln Glu Asp Gln Gly Ala
            1445                1450                1455
Gly Glu Val Glu Arg Thr Ser Arg Ala Val Glu Glu Lys Phe Arg Ala
        1460                1465                1470
Leu Cys Gln Pro Met Arg Glu Arg Cys Arg Arg Leu Gln Ala Ser Arg
    1475                1480                1485
Glu Gln His Gln Phe His Arg Asp Val Glu Asp Glu Ile Leu Trp Val
    1490                1495                1500
Thr Glu Arg Leu Pro Met Ala Ser Ser Met Glu His Gly Lys Asp Leu
1505                1510                1515                1520
Pro Ser Val Gln Leu Leu Met Lys Lys Asn Gln Thr Leu Gln Lys Glu
            1525                1530                1535
Ile Gln Gly His Glu Pro Arg Ile Ala Asp Leu Arg Glu Arg Gln Arg
        1540                1545                1550
Ala Leu Gly Ala Ala Ala Ala Gly Pro Glu Leu Ala Glu Leu Gln Glu
    1555                1560                1565
Met Trp Lys Arg Leu Gly His Glu Leu Glu Leu Arg Gly Lys Arg Leu
    1570                1575                1580
Glu Asp Ala Leu Arg Ala Gln Gln Phe Tyr Arg Asp Ala Ala Glu Ala
1585                1590                1595                1600
Glu Ala Trp Met Gly Glu Gln Glu Leu His Met Met Gly Gln Glu Lys
            1605                1610                1615
Ala Lys Asp Glu Leu Ser Ala Gln Ala Glu Val Lys Lys His Gln Val
        1620                1625                1630
Leu Glu Gln Ala Leu Ala Asp Tyr Ala Gln Thr Ile His Gln Leu Ala
    1635                1640                1645
Ala Ser Ser Gln Asp Met Ile Asp His Glu His Pro Glu Ser Thr Arg
    1650                1655                1660
```

```
Ile Ser Ile Arg Gln Ala Gln Val Asp Lys Leu Tyr Ala Gly Leu Lys
1665                1670                1675                1680

Glu Leu Ala Gly Glu Arg Arg Glu Arg Leu Gln Glu His Leu Arg Leu
                1685                1690                1695

Cys Gln Leu Arg Arg Glu Leu Asp Asp Leu Glu Gln Trp Ile Gln Glu
            1700                1705                1710

Arg Glu Val Val Ala Ala Ser His Glu Leu Gly Gln Asp Tyr Glu His
    1715                1720                1725

Val Thr Met Leu Arg Asp Lys Phe Arg Glu Phe Ser Arg Asp Thr Ser
1730                1735                1740

Thr Ile Gly Gln Glu Arg Val Asp Ser Ala Asn Ala Leu Ala Asn Gly
1745                1750                1755                1760

Leu Ile Ala Gly Gly His Ala Ala Arg Ala Thr Val Ala Glu Trp Lys
                1765                1770                1775

Asp Ser Leu Asn Glu Ala Trp Ala Asp Leu Leu Glu Leu Leu Asp Thr
            1780                1785                1790

Arg Gly Gln Val Leu Ala Ala Ala Tyr Glu Leu Gln Arg Phe Leu His
    1795                1800                1805

Gly Ala Arg Gln Ala Leu Ala Arg Val Gln His Lys Gln Gln Gln Leu
1810                1815                1820

Pro Asp Gly Thr Gly Arg Asp Leu Asn Ala Ala Glu Ala Leu Gln Arg
1825                1830                1835                1840

Arg His Cys Ala Tyr Glu His Asp Ile Gln Ala Leu Ser Pro Gln Val
                1845                1850                1855

Gln Gln Val Gln Asp Asp Gly His Arg Leu Gln Lys Ala Tyr Ala Gly
            1860                1865                1870

Asp Lys Ala Glu Glu Ile Gly Arg His Met Gln Ala Val Ala Glu Ala
    1875                1880                1885

Trp Ala Gln Leu Gln Gly Ser Ser Ala Ala Arg Arg Gln Leu Leu Leu
1890                1895                1900

Asp Thr Thr Asp Lys Phe Arg Phe Phe Lys Ala Val Arg Glu Leu Met
1905                1910                1915                1920

Leu Trp Met Asp Glu Val Asn Leu Gln Met Asp Ala Gln Glu Arg Pro
                1925                1930                1935

Arg Asp Val Ser Ser Ala Asp Leu Val Ile Lys Asn Gln Gln Gly Ile
            1940                1945                1950

Lys Ala Glu Ile Glu Ala Arg Ala Asp Arg Phe Ser Ser Cys Ile Asp
    1955                1960                1965

Met Gly Lys Glu Leu Leu Ala Arg Ser His Tyr Ala Ala Glu Glu Ile
    1970                1975                1980

Ser Glu Lys Leu Ser Gln Leu Gln Ala Arg Arg Gln Glu Thr Ala Glu
1985                1990                1995                2000

Lys Trp Gln Glu Lys Met Asp Trp Leu Gln Leu Val Leu Glu Val Leu
                2005                2010                2015

Val Phe Gly Arg Asp Ala Gly Met Ala Glu Ala Trp Leu Cys Ser Gln
            2020                2025                2030

Glu Pro Leu Val Arg Ser Ala Glu Leu Gly Cys Thr Val Asp Glu Val
    2035                2040                2045

Glu Ser Leu Ile Lys Arg His Glu Ala Phe Gln Lys Ser Ala Val Ala
    2050                2055                2060

Trp Glu Glu Arg Phe Cys Ala Leu Glu Lys Leu Thr Ala Leu Glu Glu
2065                2070                2075                2080
```

```
Arg Glu Lys Glu Arg Lys Arg Lys Arg Glu Glu Glu Arg Arg Lys
            2085                2090                2095

Gln Pro Pro Ala Pro Glu Pro Thr Ala Ser Val Pro Pro Gly Asp Leu
        2100                2105                2110

Val Gly Gly Gln Thr Ala Ser Asp Thr Thr Trp Asp Gly Thr Gln Pro
        2115                2120                2125

Arg Pro Pro Pro Ser Thr Gln Ala Pro Ser Val Asn Gly Val Cys Thr
        2130                2135                2140

Asp Gly Glu Pro Ser Gln Pro Leu Leu Gly Gln Gln Arg Leu Glu His
2145                2150                2155                2160

Ser Ser Phe Pro Glu Gly Pro Gly Pro Gly Ser Gly Asp Glu Ala Asn
                2165                2170                2175

Gly Pro Arg Gly Glu Arg Gln Thr Arg Thr Arg Gly Pro Ala Pro Ser
            2180                2185                2190

Ala Met Pro Gln Ser Arg Ser Thr Glu Ser Ala His Ala Ala Thr Leu
        2195                2200                2205

Pro Pro Arg Gly Pro Glu Pro Ser Ala Gln Glu Gln Met Glu Gly Met
    2210                2215                2220

Leu Cys Arg Lys Gln Glu Met Glu Ala Phe Gly Lys Lys Ala Ala Asn
2225                2230                2235                2240

Arg Ser Trp Gln Asn Val Tyr Cys Val Leu Arg Arg Gly Ser Leu Gly
                2245                2250                2255

Phe Tyr Lys Asp Ala Lys Ala Ala Ser Ala Gly Val Pro Tyr His Gly
            2260                2265                2270

Glu Val Pro Val Ser Leu Ala Arg Ala Gln Gly Ser Val Ala Phe Asp
        2275                2280                2285

Tyr Arg Lys Arg Lys His Val Phe Lys Leu Gly Leu Gln Asp Gly Lys
        2290                2295                2300

Glu Tyr Leu Phe Gln Ala Lys Asp Glu Ala Glu Met Ser Ser Trp Leu
2305                2310                2315                2320

Arg Val Val Asn Ala Ala Ile Ala Thr Ala Ser Ser Ala Ser Gly Glu
                2325                2330                2335

Pro Glu Glu Pro Val Val Pro Ser Thr Thr Arg Gly Met Thr Arg Ala
            2340                2345                2350

Met Thr Met Pro Pro Val Ser Pro Val Gly Ala Glu Gly Pro Val Val
        2355                2360                2365

Leu Arg Ser Lys Asp Gly Arg Glu Arg Glu Arg Glu Lys Arg Phe Ser
    2370                2375                2380

Phe Phe Lys Lys Asn Lys
2385                2390

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctgccttcct gcttcacttt                                              20

<210> SEQ ID NO 4
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 4
tcatgacgag ctgacaaagc                                                 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccctgccaac tggtgtttag                                                 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggtccccttg gacactttc                                                  20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgcctgtctg tgttcctgag                                                 20

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcctccatct ttgtgtttgt tg                                              22

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acaccaggag ttcctgtcca                                                 20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 10
tgctccgagt gctattcctt                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ttggtgtggg tttcctcttc                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cactggtcca cctcctgtct                                              20

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gaacttctgg gaggcctga                                               19

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tccctgaagg ctgtgctaat                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cctcgtgggc tttaattctg                                              20

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 16
atgtgtgcaa ggcatctgg                                               19

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ccaccctgtc ccttccacta                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cccagttctg accagcctaa                                              20

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
agaggcactg tcccttggt                                               19

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gctggttcac actccacaga                                              20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gaaaaacgca gccaggttag                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 22
gctcttgatg tgctccttcc                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggctgggtta aggctctgac                                              20

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agggactcac cacccacat                                               19

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gctgcctccc acaattcac                                               19

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tccccattgc ttcatttttc                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggaagaagct tccaaacagg                                              20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
```
ccatcctgct ccttcacatt                                          20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tgcttgttgg tccctacctc                                          20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggtttcctgt gccacgttta                                          20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggttagccaa agggtcacaa                                          20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
acaaaaacca cgtcctggag                                          20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggctaatttg ggcactttga                                          20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cccctttctt ctgctgttca                                             20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gcggaaatgc agagctaaca                                             20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ggagatggtc aatgccaaag                                             20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tgtccccact cccactaatc                                             20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
aaaaacacgt ccaagtctgg                                             20

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ctgacgggtg ttaccatcg                                              19

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
agcactgaag gctccacatt                                             20

```
<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gaacagaccg gaggtcagag                                              20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ctgtgggtcc tccactcttc                                              20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
taacatcacg gcatggtctg                                              20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ccctagctcc tgggaactct                                              20

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cttggagtcc cccgctct                                                18

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
aagcagaaag ccaccaagaa                                              20
```

-continued

```
<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tcacatcctg gtgctaactc a                                              21

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cctactctgg aacccacagg                                                20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ccactctgac ccaccatctt                                                20

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
aagccagcac aggtcagg                                                  18

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ccctcttaca cgcaaccttc                                                20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gacccttcgc ctcacagtta                                                20
```

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ggttagggat ctcccgtctc                                          20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54 cccttttgccc agaagatgta                                         20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
agatgggagc agaactggaa                                          20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ctggcctggt tactccactc                                          20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
tacgctctca ccagcagcta                                          20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cgcacacatc cagtcttacc                                          20

<210> SEQ ID NO 59

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cagctcactt tctgcctcct                                                 20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
agagaggctg tggtcaggaa                                                 20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
agcgctacca cgacatcaag                                                 20

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ccctcgactc ttgatcactc tt                                              22

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gtggccaagc tagagcagag                                                 20

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cacctcccag aggaaacg                                                   18

<210> SEQ ID NO 65
<211> LENGTH: 39
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cacgacgttg taaaacgacg aactgggact taccaagct                              39

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gaactgggac ttaccaagcc                                                   20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ccaaagaagc ccctgtatca                                                   20

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
cctcagcttc acccacctc                                                    19

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
agcgctacca cgacatcaag                                                   20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
caggtcctcc actcctgcta                                                   20

<210> SEQ ID NO 71
<211> LENGTH: 20
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 71
gtgtcccagg acaactttgg                                                     20

<210> SEQ ID NO 72
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
atccagtcca ggttgaggag gagccgctcc                                          30

<210> SEQ ID NO 73
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ctcctcaacc tggactggat ggaagagatg                                          30

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ctccagggtg agcttcagg                                                      19

<210> SEQ ID NO 75
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ctcatctcag aagaggatct gagcagcacg ctgtcaccc                                39

<210> SEQ ID NO 76
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
cgcgggtacc accatggaac aaaaactcat ctcagaagag gatc                          44

<210> SEQ ID NO 77
<211> LENGTH: 19
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 77
gaggagcctc agcaggttg                                                   19
```

. . . . . . . . . . . . . . . . . . . . . . . . . . . . . . . . . .

IDENTIFICATION OF A GENE ASSOCIATED WITH SPINOCEREBELLAR ATAXIA TYPE 5 AND METHODS OF USE

CONTINUING APPLICATION DATA

This application claims the benefit of U.S. Provisional Application Ser. No. 60/655,172 filed Feb. 22, 2005, which is incorporated by reference herein.

GOVERNMENT FUNDING

The present invention was made with government support under Grant No. NS33958 and PO1 NS33718, awarded by the National Institutes of Health. The Government may have certain rights in this invention.

BACKGROUND

The dominant spinocerebellar ataxias (SCAs) are a heterogeneous group of neurodegenerative disorders characterized by incoordination of gait, limb, and eye movements, slurred speech and swallowing difficulties. Nine of the 11 known SCA mutations are microsatellite repeat expansions (Schols et al., Lancet Neurol 3, 291-304 (2004). In 1994, SCA5 was mapped to 11q13, a centromeric region with suppressed recombination (Ranum et al., Nature Genetics 8, 280-284 (1994). MRI and autopsy findings show cerebellar cortical atrophy, Purkinje cell loss and thinning of the molecular layer (Liquori et al., Spinocerebellar ataxia type 5 (SCA5) in Cerebellar Ataxias ed. M. Pandolfo, Cambridge University Press pp 445-450. in The Cerebellum and its Disorders (eds. Manto, M.U. & Pandolfo, M.) 445-450 (Cambridge University Press, Cambridge, 2002). Additional SCA5 families from France and Germany were reported with similar clinical and neuroradiological findings (Stevanin et al., Neurology 53, 1355-1357 (1999), and Burk et al., Neurology 62, 327-329 (2004)).

The significance of identifying ataxia genes provides an improved method for diagnosis of individuals with the disease and allows the possibility of prenatal/presymptomatic diagnosis for better classification of ataxias.

SUMMARY OF THE INVENTION

The invention relates to the newly discovered correlation between mutations in the protein β-III spectrin (encoded by the SPTBN2 gene) and the disease spinocerebellar ataxia type 5 (SCA5). It has been discovered that β-III spectrin mutations cause SCA5 in an 11-generation American kindred descended from President Lincoln's grandparents, and two additional families. β-III spectrin is highly expressed in Purkinje cells and has been shown to stabilize the glutamate transporter EAAT4 at the surface of the plasma membrane. Dramatic differences in EAAT4 and GluRδ2 were found by Western and cell fractionation in SCA5 autopsy tissue. Cell culture studies demonstrated that wildtype but not mutant β-III spectrin stabilizes EAAT4 at the plasma membrane. Spectrin mutations are a novel cause of ataxia and neurodegenerative disease that affect membrane proteins involved in glutamate signaling.

In one aspect, the present invention provides methods that include analyzing an SCA5 polynucleotide, and determining whether the SCA5 polynucleotide includes a mutation. The SCA5 polynucleotide can be obtained from a subject, where a subject at risk of having SCA5 has a mutation in an SCA5 polynucleotide, or a subject not at risk of having SCA5 does not have a mutation in an SCA5 polynucleotide. The subject may or may not display at least one symptom of ataxia. The SCA5 polynucleotide can be a genomic SCA5 polynucleotide or a processed SCA5 polynucleotide. The analyzing can include amplification of the SCA5 polynucleotide, hybridization of the SCA5 polynucleotide to a second polynucleotide, sequencing a portion of the SCA5 polynucleotide, or a combination thereof. The SCA5 polynucleotide may contain a mutation, and the mutation may be present in an exon. A mutation in an exon may result in an SCA5 polypeptide having an amino acid sequence different than SEQ ID NO:2. The type of mutation may be, for instance, a mutation in a nucleotide corresponding to exon 7 of the SCA5 polynucleotide, a mutation in a nucleotide corresponding to exon 12 of the SCA5 polynucleotide, a mutation in a nucleotide corresponding to exon 14 of the SCA5 polynucleotide, or a combination thereof.

The present invention also provides a method for identifying a subject not at risk for developing spinocerebellar ataxia type 5. The method includes analyzing nucleotides of SCA5 polynucleotide, and determining if the polynucleotide includes a mutation, wherein a subject not at risk of having SCA5 does not have a mutation in an SCA5 polynucleotide.

The SCA5 polynucleotide can be a genomic SCA5 polynucleotide or a processed SCA5 polynucleotide. The analyzing can include amplification of the SCA5 polynucleotide, hybridization of the SCA5 polynucleotide to a second polynucleotide, sequencing a portion of the SCA5 polynucleotide, or a combination thereof. The SCA5 polynucleotide may contain a mutation, and the mutation may be present in an exon. A mutation in an exon may result in an SCA5 polypeptide having an amino acid sequence different than SEQ ID NO:2. The type of mutation may be, for instance, a mutation in a nucleotide corresponding to exon 7 of the SCA5 polynucleotide, a mutation in a nucleotide corresponding to exon 12 of the SCA5 polynucleotide, a mutation in a nucleotide corresponding to exon 14 of the SCA5 polynucleotide, or a combination thereof.

The present invention further provides a method for identifying a subject at risk for developing spinocerebellar ataxia type 5. The method includes analyzing nucleotides of SCA5 polynucleotide, and determining if the polynucleotide includes a mutation, wherein a subject at risk of having SCA5 has a mutation in an SCA5 polynucleotide. The subject may or may not display at least one symptom of ataxia. The SCA5 polynucleotide can be a genomic SCA5 polynucleotide or a processed SCA5 polynucleotide. The analyzing can include amplification of the SCA5 polynucleotide, hybridization of the SCA5 polynucleotide to a second polynucleotide, sequencing a portion of the SCA5 polynucleotide, or a combination thereof. The SCA5 polynucleotide may contain a mutation, and the mutation may be present in an exon. A mutation in an exon may result in an SCA5 polypeptide having an amino acid sequence different than SEQ ID NO:2. The type of mutation may be, for instance, a mutation in a nucleotide corresponding to exon 7 of the SCA5 polynucleotide, a mutation in a nucleotide corresponding to exon 12 of the SCA5 polynucleotide, a mutation in a nucleotide corresponding to exon 14 of the SCA5 polynucleotide, or a combination thereof.

The present invention provides a method for determining whether a subject has spinocerebellar ataxia type 5 (SCA5). The method includes analyzing an SCA5 polynucleotide for a mutation, and determining whether the subject displays a symptom of SCA5, wherein having a mutation in an SCA5 polynucleotide and having a symptom of SCA5 indicates the subject has SCA5. The SCA5 polynucleotide can be a genomic SCA5 polynucleotide or a processed SCA5 polynucleotide. The analyzing can include amplification of the SCA5 polynucleotide, hybridization of the SCA5 polynucleotide to a second polynucleotide, sequencing a portion of the SCA5 polynucleotide, or a combination thereof. The SCA5 polynucleotide may contain a mutation, and the mutation may be present in an exon. A mutation in an exon may result in an SCA5 polypeptide having an amino acid sequence different than SEQ ID NO:2. The type of mutation may be, for instance, a mutation in a nucleotide corresponding to exon 7 of the SCA5 polynucleotide, a mutation in a nucleotide corresponding to exon 12 of the SCA5 polynucleotide, a mutation in a nucleotide corresponding to exon 14 of the SCA5 polynucleotide, or a combination thereof.

Also included in the present invention is a kit for detecting an SCA5 polynucleotide, including a primer pair that will amplify a portion of an SCA5 polynucleotide. The present invention also provides an isolated polynucleotide including a mutant of SEQ ID NO:1 or a portion thereof. The mutation present in the polynucleotide may be a mutation in a nucleotide corresponding to exon 7 of the SCA5 polynucleotide, a mutation in a nucleotide corresponding to exon 12 of the SCA5 polynucleotide, a mutation in a nucleotide corresponding to exon 14 of the SCA5 polynucleotide, or a combination thereof. The isolated polynucleotide may be 15 to 500 nucleotides. Also included is a vector including an isolated polynucleotide of the present invention, and a cell including the vector.

The terms "comprises" and variations thereof do not have a limiting meaning where these terms appear in the description and claims. Unless otherwise specified, "a," "an," "the," and "at least one" are used interchangeably and mean one or more than one.

BRIEF DESCRIPTION OF THE FIGURES

FIG. 6. Nucleotide sequence of a genomic SPTBN2 gene and amino acid sequence of SPTBN2 polypeptide. Exons are shown in capital letters, and introns are shown in small letters. The locations of single nucleotide polymorphisms (SNP) are underlined and the dbSNP rs# cluster id is shown above each SNP. rs5792396, presence or absence of a C; rs10702473, presence or absence of AAA; rs5792395, presence or absence of a G immediately before the underlined C; rs11286358, presence or absence an A. The sequence listing reflects the different nucleotides that can be present at each of the remaining SNPs.

DETAILED DESCRIPTION OF PREFERRED EMBODIMENTS OF THE INVENTION

Compositions

Figure 1:
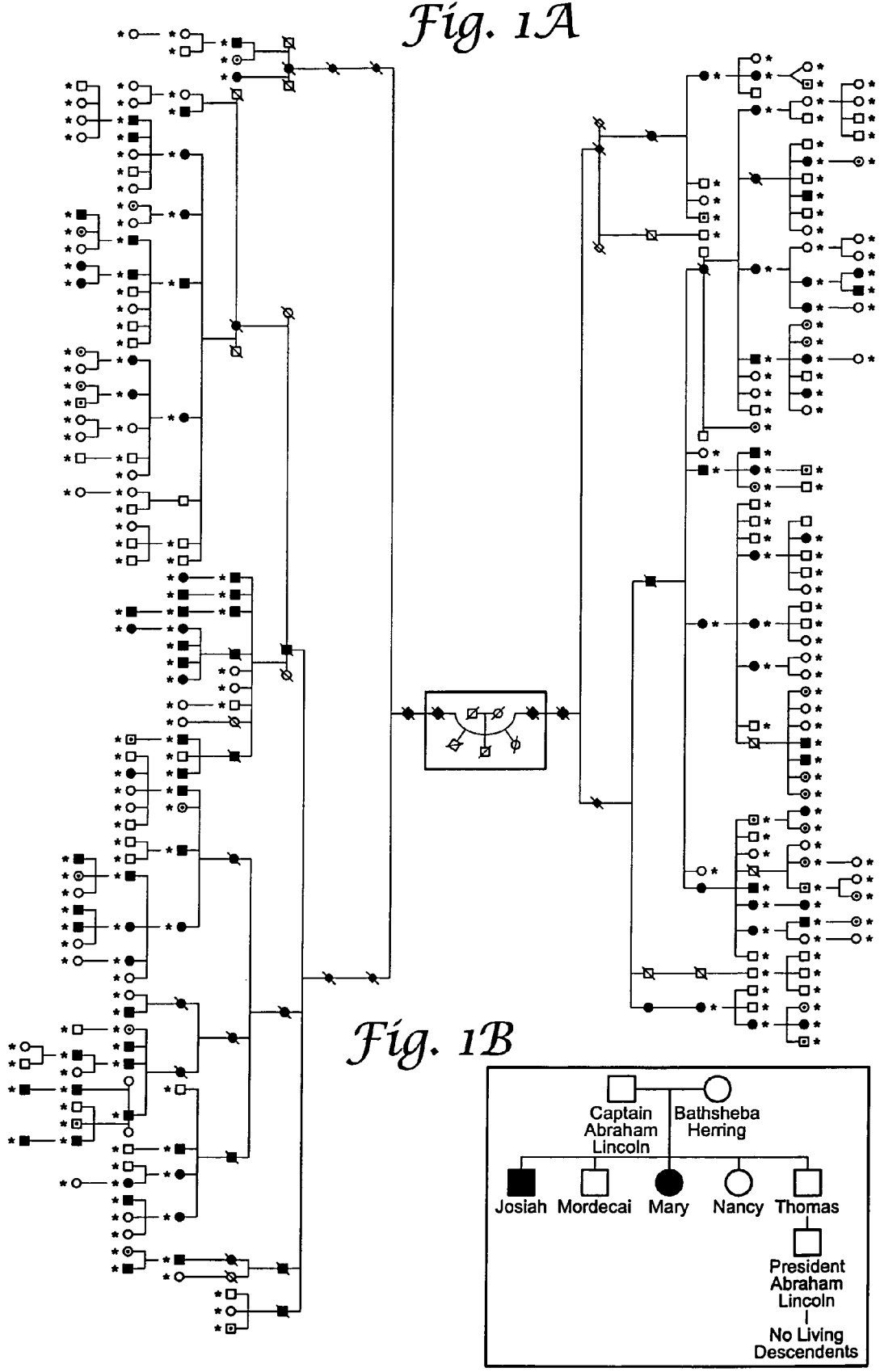
FIG. 1. Pedigree of the Lincoln SCA5 family. (a) An 11-generation SCA5 kindred descended from paternal grandparents of President Abraham Lincoln. Squares and circles represent males and females, respectively, shaded symbols represent affected individuals, symbols with a dot indicate obligate mutation carriers, and diagonal lines denote individuals who are deceased. The asterisks beneath the symbols indicate individuals whose blood samples were obtained for analysis. (b) Enlargement of a portion of the pedigree showing the common ancestry of the two branches and their relationship to President Lincoln. The pedigrees of the two branches are abbreviated, and the genders of Josiah and Mary and individuals in generations III, IV, V are masked in (a) to preserve confidentiality.

The present invention includes polynucleotides associated with SCA5, polypeptides encoded by the polynucleotides, and methods for identifying such polynucleotides and polypeptides. As used herein, the term "polynucleotide" refers to a polymeric form of nucleotides of any length, either ribonucleotides or deoxynucleotides. A polynucleotide may include nucleotide sequences having different functions, including for instance coding sequences such as exons, and non-coding sequences such as introns, regulatory sequences, and the like. A polynucleotide can be obtained directly from a natural source, or can be prepared with the aid of recombinant, enzymatic, or chemical techniques. A polynucleotide can be linear or circular in topology, and can be, for example, a portion of a vector, such as an expression or cloning vector, or a fragment. Polynucleotides can be single-stranded or double-stranded, and the sequence of the second, complementary strand is dictated by the sequence of the first strand. The term "polynucleotide" is therefore to be broadly interpreted as encompassing a single stranded nucleic acid polymer, its complement, and the duplex formed thereby. "Complementarity" of polynucleotides refers to the ability of two single-stranded polynucleotides to base pair with each other, in which an adenine on one polynucleotide will base pair with a thymidine (or uracil, in the case of RNA) on the other, and a cytidine on one polynucleotide will base pair with a guanine on the other. Two polynucleotides are complementary to each other when a nucleotide sequence in one polynucleotide can base pair with a nucleotide sequence in a second polynucleotide. For instance, 5'-ATGC and 5'-GCAT are fully complementary, as are 5'-GCTA and 5'-TAGC.

As used herein, the term "polypeptide" refers broadly to a polymer of two or more amino acids joined together by peptide bonds. The term "polypeptide" also includes molecules which contain more than one polypeptide joined by a disulfide bond, or complexes of polypeptides that are joined together, covalently or noncovalently, as multimers (e.g., dimers, tetramers). Thus, the terms peptide, oligopeptide, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring.

A polynucleotide or polypeptide may be isolated. An "isolated" polypeptide or polynucleotide means a polypeptide or polynucleotide that has been removed from its natural environment. A polypeptide or polynucleotide may be purified, i.e., essentially free from any other polypeptide or polynucleotide and associated cellular products or other impurities. A "purified" polypeptide or polynucleotide is one that is at least 60% free, preferably 75% free, and most preferably 90% free from other components with which they are naturally associated. Polypeptides and nucleotides that are produced outside the organism in which they naturally occur, e.g., through chemical or recombinant means, are considered to be isolated and purified by definition, since they were never present in a natural environment.

A polynucleotide of the present invention, referred to herein interchangeably as an SCA5 polynucleotide and an SPTBN2 polynucleotide, is a polynucleotide originating from the long arm of human chromosome 11 (11q13), between the microsatellite markers KADSCA5-184 and D11S970. An SCA5 polynucleotide may be genomic or processed. A genomic SCA5 polynucleotide includes a polynucleotide that encodes an unprocessed preRNA (i.e., an RNA molecule that includes both exons and introns), and the preRNA. When placed under the control of appropriate regulatory sequences, a genomic SCA5 polynucleotide produces an mRNA. The boundaries of a genomic SCA5 polynucleotide are generally determined by a transcription initiation site at its 5' end and a transcription terminator at its 3'end. A genomic SCA5 polynucleotide typically includes introns and exons. A regulatory sequence is a polynucleotide that regulates expression of a genomic sequence to which it is operably linked. A non-limiting example of a regulatory sequence includes promoters. "Operably linked" refers to a juxtaposition wherein the components so described are in a relationship permitting them to function in their intended manner. A regulatory sequence is "operably linked" to a genomic sequence when it is joined in such a way that expression of the genomic sequence is achieved under conditions compatible with the regulatory sequence.

An example of a genomic SCA5 polynucleotide is shown in FIG. 6 (SEQ ID NO: 1). Other examples are disclosed at Genbank accession number NM_006946 and AB008567. A genomic SCA5 polynucleotide typically includes 37 exons, and encodes a polypeptide of 2,390 amino acids (Stankewich et al., Proc. Nat. Acad. Sci. USA, 95:14158-14163 (1998)), an example being SEQ ID NO:2. This polypeptide is often referred to in the art as βIII spectrin. A processed SCA5 polynucleotide is the mRNA originating from transcription of the genomic SCA5 polynucleotide followed by removal of the nucleotides corresponding to the introns. An example of a processed SCA5 polynucleotide is SEQ ID NO:1 without the nucleotides corresponding to the introns. A processed SCA5 polynucleotide also includes a DNA polynucleotide derived from the mRNA, for instance a cDNA. Furthermore, an SCA5 polynucleotide of the present invention also includes the complements of a genomic or processed SCA5 polynucleotide.

An SCA5 polynucleotide of the present invention includes one or more mutations. The SCA5 polynucleotide depicted at SEQ ID NO:1 is an example of a normal non-mutated genomic SCA5 polynucleotide, also referred to herein as a wildtype genomic SCA5 polynucleotide. Likewise, a wild-type processed SCA5 polynucleotide has a nucleotide sequence as depicted in SEQ ID NO:1 without the sequences corresponding to the introns. Several single nucleotide polymorphisms (SNPs) have been identified in normal SCA5 polynucleotides. The locations of these SNPs are shown in FIG. 6. The presence of a SNP in an SCA5 polynucleotide is not considered to be a mutation. One skilled in the art will understand that additional SNPs are likely to be discovered on an ongoing basis, and at an increasing rate, especially in view of the recent sequencing of the human genome. Any change in nucleotide sequence of an SCA5 polynucleotide when compared to SEQ ID NO:1 is considered to be a mutation.

A mutation may exist in nucleotides corresponding to a 5' upstream region, a 5' untranslated region (UTR), an exon, an intron, a 3' UTR, or a 3' downstream region. A mutation may influence the amount of polypeptide produced by an SCA5 polynucleotide, for instance by altering transcription of the genomic SCA5 polynucleotide, or altering (such as destabilizing) translation of the mRNA. A mutation may alter the amino acid sequence of an SCA5 polypeptide. Examples of mutations include, for instance, deletions, insertions, duplications, and point mutations. A mutation may result in, for instance, a frameshift, an amino acid substitution, insertion or deletion of amino acids, and/or premature termination of translation through the presence of a stop codon.

In some aspects, a mutation in an SCA5 polynucleotide is in an exon, and results in an amino acid sequence that is altered when compared to the amino acid sequence depicted at SEQ ID NO:2. As is well known, many mutations to a nucleotide sequence encoding a polypeptide can result in a silent mutation, i.e., the nucleotide mutation has no effect on the amino acid sequence. Due to the third-base degeneracy present in a codon, the base in the third position of a codon is often not significant, and a change in the third nucleotide of a codon often does not result in a different amino acid. For instance, the codon AAA and AAG both encode the amino acid lysine. A mutation in an SCA5 polynucleotide can result in an SCA5 polypeptide having altered activity. Altered activities include decreased stabilization of EAAT4 at the plasma membrane of Purkinje cells.

It is expected that mutations can be present in essentially any location of an SCA5 polynucleotide, preferably a location that corresponds to an exon. For instance, a mutation can be in a region encoding the amino terminal domain of an SCA5 polypeptide, such as the actin-binding domain, or in one of the spectrin repeat domains including, but not limited to, the third spectrin repeat domain. Without intending to be limiting, several mutations have been detected in SCA5 polynucleotides. For instance, mutations have been detected in the sequences corresponding to exon 7, including the sequences spanning nucleotides 7654-7769, and specifically a T to C (A to G on the non-coding strand) at nucleotide 7755. Mutations have been detected in the sequences corresponding to exon 12, including the sequences spanning 13582-13884, and specifically a deletion of nucleotides 13,823-13,861 or 13,827-13,865. Mutations have also been detected in the sequences corresponding to exon 14, including the sequences spanning nucleotides 15932-16802, and specifically a deletion of nucleotides 16010-16024.

The present invention also includes shorter polynucleotides that correspond to a portion of a genomic or processed SCA5 polynucleotide. In some aspects the shorter polynucleotides are referred to herein as primers and probes. A polynucleotide of this aspect of the invention has a nucleotide sequence that is complementary to a nucleotide sequence of a genomic SCA5 polynucleotide, or the complement thereof. In some embodiments, a polynucleotide of this aspect of the invention includes consecutive nucleotides selected from nucleotides 1-159, 160-316, 317-5418, 5419-5570, 5571-6004, 6005-6178, 6179-6992, 6993-7084, 7085-7228, 7229-7309, 7310-7653, 7654-7769, 7770-10370, 10371-10483, 10484-10630, 10631-10818, 10819-12380, 12381-12498, 12499-13100, 13101-13259, 13260-13581, 13582-13884, 13885-15562, 15563-15716, 15717-15931, 15932-16802, 16803-19678, 19679-19816, 19817-20117, 20118-20874, 20875-21791, 21792-21994, 21995-22317, 22318-22408, 22409-22614, 22615-22761, 22762-24859, 24860-25123, 25124-27036, 27037-27261, 27262-27538, 27539-27628, 27629-27953, 27954-28214, 28215-28399, 28300-28430, 28431-28659, 28660-28864, 28865-29741, 29742-30116, 30117-31115, 31116-31360, 31361-31455, 31456-31594, 31595-32218, 32219-32303, 32304-32549, 32550-32746, 32747-33087, 33088-33230, 33231-33319, 33320-33395, 33396-33480, 33481-33531, 33532-33751, 33752-33972, 33973-34231, 34232-34405, 34406-34958, 34959-35001, 35002-35294, 35295-35525, 35526-36147 of SEQ ID NO:1, or the complements thereof. Also included are portions of these polynucleotides, wherein the portion is at least 100 consecutive nucleotides, at least 200 consecutive nucleotides, at least 300 consecutive nucleotides, at least 400 consecutive nucleotides, or at least 500 consecutive nucleotides. Other polynucleotides of this aspect of the invention include the polynucleotides depicted at Table 1 (SEQ ID NOs:3 to 77), or the complements thereof. In some embodiments, a polynucleotide of this aspect of the invention includes a mutation. For instance, a polynucleotide can include nucleotides 13773-13822 and 13867-13917 (i.e., reflects one of the American mutations described in detail herein), include nucleotides 13777-13826 and 13867-13920 (i.e., reflects one of the American mutations described in detail herein), include nucleotides 15879-15929 and 16803-16853 (i.e., reflects the French mutation described in detail herein), or the complements thereof. Typically, a polynucleotide of this aspect of the invention has at least about 95% sequence identity, preferably at least about 97% sequence identity, most preferably, about 100% sequence identity with the target sequence to which the primer hybridizes.

Also included in the present invention are primer pairs. As used herein, the term "primer pair" means two oligonucleotides designed to flank a region of a polynucleotide to be amplified. The polynucleotide to be amplified can be referred to as the template polynucleotide. In some aspects, the template polynucleotide is a genomic SCA5 polynucleotide. Methods for amplifying a polynucleotide are discussed herein. One primer is complementary to nucleotides present on one strand at one end of a template polynucleotide and another primer is complementary to nucleotides present on the other strand at the other end of the template polynucleotide. For example, in some aspects the primers of a primer pair may be used to amplify nucleotides corresponding to one or more exons, or nucleotides corresponding to a portion of an exon. When the template polynucleotide is obtained from genomic DNA, one or both of the primers of the primer pair may be complementary to nucleotides corresponding to an intron. Examples of primer pairs are disclosed at Table 1, and those skilled in the art will recognize that other primer pairs can be easily made using the sequence present at SEQ ID NO:1 and routine methods. A polynucleotide of this aspect of the invention includes, in increasing order of preference, at least 15 consecutive nucleotides, at least 18 consecutive nucleotides, at least 20 consecutive nucleotides, at least 24 consecutive nucleotides, or at least 27 consecutive nucleotides. Typically, a polynucleotide of this aspect of the invention has at least about 95% sequence identity, preferably at least about 97% sequence identity, most preferably, about 100% sequence identity with the target sequence to which the primer hybridizes.

A polynucleotide of the invention can be inserted in a vector. A vector is a replicating polynucleotide, such as a plasmid, phage, or cosmid, to which another polynucleotide may be attached so as to bring about the replication of the attached polynucleotide. Construction of vectors containing a polynucleotide of the invention employs standard ligation techniques known in the art. See, e.g., Sambrook et al, *Molecular Cloning: A Laboratory Manual.*, Cold Spring Harbor Laboratory Press (1989). A vector can provide for further cloning (amplification of the polynucleotide), i.e., a cloning vector, or for expression of the polypeptide encoded by the coding region, i.e., an expression vector. The term vector includes, but is not limited to, plasmid vectors, viral vectors, cosmid vectors, or artificial chromosome vectors. Typically, a vector is capable of replication in a bacterial host, for instance *E. coli*. Preferably the vector is a plasmid. Selection of a vector depends upon a variety of desired characteristics in the resulting construct, such as a selection marker, vector replication rate, and the like. Suitable host cells for cloning or expressing the vectors herein are prokaryote or eukaryotic cells. The vector may contain an entire SCA5 polynucleotide, or a portion thereof, for instance, a region of nucleotides corresponding to an exon, an intron, or a combination thereof. The present invention also includes cells containing a polynucleotide of the invention inserted in a vector, and cells containing a polypeptide encoded by a polynucleotide of the invention inserted in a vector.

The present invention also includes SCA5 polypeptides containing one or more mutations. The SCA5 polypeptide depicted at SEQ ID NO:2 is an example of a normal non-mutated genomic SCA5 polypeptide, also referred to herein as a wildtype SCA5 polypeptide. Several single nucleotide polymorphisms (SNPs) have been identified in normal SCA5 polypeptides that result in a different amino acid sequence. The locations of these SNPs are shown in FIG. 6. The presence of an altered amino acid sequence due to a SNP in an SCA5 polypeptide is not considered to be a mutation. Any change in amino acid sequence of an SCA5 polypeptide when compared to SEQ ID NO:2 is considered to be a mutation, and is a polynucleotide of the present invention. A mutation can result in an SCA5 polypeptide containing a mutation in the amino terminal domain, such as the actin-binding domain, in one of the spectrin repeat domains including, but not limited to, the third spectrin repeat domain, or in the carboxy terminal domain.

Methods of Use

The identification of a genomic sequence that is associated with a disease allows for improved diagnosis of the disease. The present invention discloses that a mutation in an SCA5 polynucleotide is associated with the disease spinocerebellar ataxia type 5 (SCA5). The present invention includes methods for detecting a polynucleotide of the present invention, such as an SCA5 polynucleotide including a mutation in an SCA5 polynucleotide, methods for identifying a subject not at risk for developing SCA5, and methods for identifying a subject that has or is at risk for developing SCA5. The methods of the present invention typically include analyzing an SCA5 polynucleotide, generally a portion of an SCA5 polynucleotide, and determining whether the SCA5 polynucleotide comprises a mutation.

As used herein, "at risk" describes a subject having an SCA5 polynucleotide that contains a mutation. Preferably, the mutation is present in a nucleotide corresponding to an exon. Preferably, the mutation results in an SCA5 polypeptide having an amino acid sequence that is different than the amino acid sequence disclosed at SEQ ID NO:2. More than one mutation may be present. An at risk subject includes an individual who may be manifesting at least one symptom of SCA5, as well as a subject who may develop at least one symptom of SCA5 in the future. Symptoms of SCA5 include incoordination of gait, limb, and eye movements, slurred speech and swallowing difficulties. The evaluation of such symptoms is routine and easily accomplished by a person of ordinary skill. A subject that does not have an SCA5 polynucleotide containing a mutation as described herein is expected to not display symptoms of SCA5 during his or her lifetime, and is considered to be "not at risk."

The methods of the present invention include analyzing an SCA5 polynucleotide, and determining whether the SCA5 polynucleotide includes a mutation. The source of polynucleotides is typically a biological sample that includes genomic DNA and/or processed RNA. As used herein, a "biological sample" refers to a sample of material (solid or fluid) obtained from an individual, including but not limited to, for example, blood, plasma, serum, or tissue. A biological sample may be treated to obtain polynucleotides, for instance, DNA or RNA.

A subject can be a rat, mouse, human, chimpanzee, or gorilla, preferably human. The SCA5 polynucleotide that is analyzed may be an entire SCA5 polynucleotide, and is typically a portion of an SCA5 polynucleotide.

The present invention provides methods for analyzing an SCA5 polynucleotide, including at least a portion of an SCA5 polynucleotide. In one aspect, the method includes amplifying nucleotides of an SCA5 polynucleotide of a subject to form amplified polynucleotides, preferably including amplified nucleotides that correspond to an exon, and detecting the amplified polynucleotides. Preferably, nucleotides are amplified by PCR. In PCR, a molar excess of a primer pair is added to a biological sample that includes polynucleotides, preferably genomic DNA. The primers are extended to form complementary primer extension products which act as template for synthesizing the desired amplified polynucleotides. The conditions for amplifying a polynucleotide by PCR vary depending on the nucleotide sequence of primers used, and methods for determining such conditions are routine in the art.

Various types of amplification techniques are known and used routinely, such as allele-specific PCR, cold PCR, hot PCR, reverse-transcriptase PCR, and the like. These and other amplification techniques are known in the art and are used routinely. In view of the disclosure of SEQ ID NO:1, the skilled person can easily adapt an amplification technique to be used in identifying mutations in an SCA5 polynucleotide. Examples of primers that can be used in the methods of the present invention include those depicted in Table 1 (SEQ ID NOs:3-77).

After amplification, the sizes of the amplified polynucleotides may be determined, for instance by gel electrophoresis, and compared. The amplified polynucleotides can be visualized by staining (e.g., with ethidium bromide) or labeling with a suitable label known to those skilled in the art, including radioactive and nonradioactive labels. Typical radioactive labels include $^{33}$P. Nonradioactive labels include, for example, ligands such as biotin or digoxigenin as well as enzymes such as phosphatase or peroxidases, or the various chemiluminescers such as luciferin, or fluorescent compounds like fluorescein and its derivatives. Optionally, the nucleotide sequence of an amplified polynucleotide can be determined.

In another aspect of the methods for analyzing an SCA5 polynucleotide containing a mutation, polynucleotide probes are used that hybridize to a polynucleotide. As used herein, "hybridizes," "hybridizing," and "hybridization" means that a probe forms a noncovalent interaction with a target polynucleotide under standard conditions. Standard hybridizing conditions are those conditions that allow a probe to hybridize to a target polynucleotide. Such conditions are readily determined for a probe and the target polynucleotide using techniques well known to the art, for example see Sambrook et al. *Molecular Cloning: A Laboratory Manual;* Cold Spring Harbor Laboratory: New York (1989). Preferred probes useful in the present invention hybridize to a target polynucleotide by using prehybridization in a hybridization buffer, preferably RAPID-HYB buffer (Amersham, Piscataway, N.J.), at 60° for 1 hour, and hybridization overnight at 60° C. Preferably, at least 4×10$^7$ counts per minute (cpm) total of the labeled probe is used in the hybridization. When the probe used is at least about 200 nucleotides, the wash conditions used are: 2 washes for 5 minutes each at room temperature in a solution containing 2×SSC (one liter of 20×SSC contains 175.3 grams NaCl and 88.2 grams sodium citrate, pH 7.0) and 0.05% sodium dodecyl sulfate (SDS), followed by 2 to 3 washes for 30 minutes each at 52° in a solution containing 0.15×SSC and 0.1% SDS. Other hybridization conditions for use when the probe is at least about 200 nucleotides use the same prehybridization and hybridization conditions as described above, but the wash conditions used are: 2 washes for 5 minutes each at room temperature in a solution containing 2×SSC and 0.05% SDS, followed by 1 wash for 15 minutes at 50° C. in a solution containing 0.15×SSC and 0.1% SDS, followed by 1 wash for 10 minutes at 50° C. in a solution containing 0.15× SSC and 0.1% SDS. When the probe used is about 20 to about 22 nucleotides, the same prehybridization and hybridization conditions described above are used, but the wash conditions used are: two 15 minute washes at 45° C. in 2×SSC and 0.1% SDS. The nucleotide sequence of a target DNA molecule is generally a sequence complementary to the probe. The hybridizing probe may contain 1 to 10 nonhybridizing nucleotides, preferably no greater than 5, more preferably no greater than 2 nonhybridizing nucleotides, that do not interfere with forming the noncovalent interaction. The nonhybridizing nucleotides of a probe may be located at an end or within the hybridizing probe. Thus, a probe does not have to be complementary to all the nucleotides of the target DNA sequence as long as there is hybridization under standard hybridization conditions.

In one embodiment of this aspect of the invention, the methods include digesting genomic DNA of a subject with a restriction endonuclease to obtain polynucleotides, and probing the polynucleotides under hybridizing conditions with a detectably labeled probe. The digestion of genomic DNA with endonucleases is routine in the art, and numerous endonucleases are known. Typically, the polynucleotides resulting from digestion are fractionated, for instance by gel electrophoresis, denatured to yield single stranded polynucleotides, and then exposed to the probe under hybridizing conditions. The probe that has hybridized to the polynucleotide is then detected, and the size of the hybridized polynucleotide may then be determined. The presence or absence of the mutation can be inferred by the approximate molecular weight of the detected polynucleotide. The presence of a mutation indicates the person has or is at risk, and the absence of a mutation indicates the person is not at risk.

Other methods can be used to analyze an SCA5 polynucleotide. Examples include, but are not limited to, ligase-mediated detection techniques (Landegren, U.S. Pat. No. 4,988, 617), fluorescent in situ hybridization (Stokke, U.S. Pat. No. 5,633,365 and Pinkel, U.S. Pat. No. 5,665,549), direct DNA sequencing, PFGE analysis, Southern or Northern blotting, single-stranded conformation analysis (SSCA), RNAse protection assay, allele-specific oligonucleotide (Wallace, U.S. Pat. No. 5,639,611), dot blot analysis, denaturing gradient gel electrophoresis (Borresen, U.S. Pat. No. 5,190,856), RFLP (Helentjaris, U.S. Pat. No. 5,324,631) and PCR-SSCP. Methods for detecting and quantifying gene sequences, such as mutated genes and oncogenes, in for example biological fluids are described in Sorenson (U.S. Pat. No. 5,496,699).

The present invention also provides a kit for identifying whether a subject as at risk or not at risk for developing SCA5. The kit includes the primers and/or probes discussed above in a suitable packaging material in an amount sufficient for at least one assay. Optionally, other reagents such as buffers and solutions needed to practice the invention are also included. Optionally, other reagents such as buffers and solutions needed to practice the invention are also included. As used herein, the phrase "packaging material" refers to one or more physical structures used to house the contents of the kit. The packaging material is constructed by well known methods, generally to provide a sterile, contaminant-free environment. The packaging material may have a label which indicates that the polynucleotides can be used for identifying whether a subject is at risk or not at risk for developing SCA5. In addition, the packaging material contains instructions indicating how the materials within the kit are employed. As used herein, the term package or container refers to a receptacle such as glass, plastic, paper, foil, and the like, capable of holding within fixed limits the primers and/or probes. Thus, for example, a package can be a plastic vial used to contain milligram quantities of a primer pair. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

The present invention is illustrated by the following examples. It is to be understood that the particular examples, materials, amounts, and procedures are to be interpreted broadly in accordance with the scope and spirit of the invention as set forth herein.

EXAMPLES

Materials and Methods

Human subjects. All participating subjects and control individuals referred to this study signed an informed consent form as approved by the Human Subjects Committee at the University of Minnesota or by the participating institutions. Unrelated control DNA samples were obtained from the CEPH panel and from healthy North Americans (n=500). DNA was extracted from peripheral venous blood using the Puregene kit (Gentra Systems, Plymouth, Minn.).

Generation of chromosome-separated cell lines. Mouse/human hybrid cell lines haploid for the affected or normal copy of chromosome 11 were generated at GMP Genetics (Waltham, Mass.) by fusing mouse E2 cells with human lymphoblastoid cells from an affected American family member, as previously described (Papadopoulos et al., Nat Genet 11, 99-102 (1995). In brief, lymphoblast cells from an affected individual were electrofused to mouse E2 cells and HAT plus geneticin was used to select against unfused E2 and lymphoblast cells, respectively. The surviving colonies were expanded and clones containing only a single copy of the affected or normal chromosome 11 were selected by typing microsatellite markers that spanned the SCA5 region.

Screening of microsatellite repeat markers in the SCA5 region. Microsatellite repeat markers were amplified by PCR using a [$\gamma$-$^{33}$P] ATP tagged primer. Products were separated on 4% denaturing polyacrylamide gels and visualized by autoradiography. Genotyping of the single affected chromosome allowed for the exclusion of repeat-expansion mutations in non-polymorphic markers. The E2 mouse DNA was used as a negative control to confirm the amplified product was specific to human but not mouse DNA. All polymorphic markers were subsequently used to determine the affected haplotypes for each of the SCA5 families.

Construction of BAC libraries from an affected SCA5 haploid cell line and shotgun DNA sequencing. An incomplete Hind III digestion was performed on DNA from the haploid cell line containing the affected chromosome 11 and introduced into the pIndigoBAC-5 vector (Epicentre, Madison, Wis.), which was then used to prepare a BAC library of approximately 352,000 recombinant clones. The BAC libraries were screened by PCR using microsatellite markers and positive BAC clones were subsequently isolated by hybridization. Lark Technologies Inc. (Houston, Tex.) performed the shotgun sequencing and assembly. In brief, shotgun libraries were constructed for three BACs (VI-C2, VI-C11, IV-H4), which spanned the region of haplotype conservation between the American and French SCA5 families, by subcloning the fragmented DNA into the pUC57 vector. Sequencing reactions of the three shotgun libraries were performed and subsequently analyzed on ABI3730xl DNA sequencers. The sequence data was assembled using the Phred-Phrap-Consed software (Gordon et al., Genome Res 8, 195-202 (1998)and was subsequently BLASTED against specific genes using data available online through the UCSC Genome Bioinformatics and National Center for Biotechnology Information internet sites.

SPTBN2 gene sequencing in SCA5 families and mutation screening in controls. Genomic DNA of affected French and German SCA5 patients was used to amplify SPTBN2 exons by PCR and the resulting products were sequenced. After the American and French mutations were identified, family members and 1,000 control chromosomes were screened for these deletion mutations by PCR. PCR was performed by labeling the 5' end of each forward primer with [$\gamma$-$^{33}$P] ATP. The resulting products were separated on 4% denaturing polyacrylamide gels and visualized by autoradiography. Allele-specific PCR analysis was used to screen for the German missense mutation. Two forward primers, one containing an altered nucleotide (C) at its 3'-end and the other containing a 19 bp-tail at its 5'-end, were used in a single reaction to amplify both the mutant (shorter product) and normal (longer product) alleles, respectively. The resulting products were separated on 4% agarose gels and visualized by ethidium bromide. PCR was subsequently performed on unrelated 1,000 control chromosomes to screen for the German mutation. The PCR primer sequences and conditions used for SPTBN2 sequencing and mutation screening are shown in Table 1.

TABLE 1

Primer sequences and PCR conditions.
Primer sequences and PCR conditions
for SPTBN2 sequencing

| Exon(s) | Sequence (5'-3') | Ta | Mg | size (bp) |
|---|---|---|---|---|
| exon1-2 | Forward: CTGCCTTCCTGCTTCACTTT Reverse: TCATGACGAGCTGACAAAGC | 54 | 1 | 468 |
| exon3 | Forward: CCCTGCCAACTGGTGTTTAG Reverse: GGTCCCCTTGGACACTTTTC | 54 | 1 | 282 |
| exon4 | Forward: TGCCTGTCTGTGTTCCTGAG Reverse: TCCTCCATCTTTGTGTTTGTTG | 54 | 1 | 395 |
| exon5-6 | Forward: ACACCAGGAGTTCCTGTCCA Reverse: TGCTCCGAGTGCTATTCCTT | 54 | 1 | 495 |
| exon7 | Forward: TTGGTGTGGGTTTCCTCTTC Reverse: CACTGGTCCACCTCCTGTCT | 54 | 1 | 248 |
| exon8-9 | Forward: GAACTTCTGGGAGGCCTGA Reverse: TCCCTGAAGGCTGTGCTAAT | 54 | 1 | 568 |

TABLE 1-continued

Primer sequences and PCR conditions.
Primer sequences and PCR conditions
for SPTBN2 sequencing

| Exon(s) | Sequence (5'-3') | Ta | Mg | size (bp) |
|---|---|---|---|---|
| exon10 | Forward: CCTCGTGGGCTTTAATTCTG Reverse: ATGTGTGCAAGGCATCTGG | 54 | 1 | 228 |
| exon11 | Forward: CCACCCTGTCCCTTCCACTA Reverse: CCCAGTTCTGACCAGCCTAA | 54 | 1 | 244 |
| exon12 | Forward: AGAGGCACTGTCCCTTGGT Reverse: GCTGGTTCACACTCCACAGA | 54 | 1 | 464 |
| exon13 | Forward: GAAAAACGCAGCCAGGTTAG Reverse: GCTCTTGATGTGCTCCTTCC | 54 | 1 | 279 |
| exon14 | Forward: GGCTGGGTTAAGGCTCTGAC Reverse: AGGGACTCACCACCCACAT | 57 | 1 | 990 |
| exon15 | Forward: GCTGCCTCCCACAATTCAC Reverse: TCCCCATTGCTTCATTTTTC | 54 | 1 | 234 |
| exon16 | Forward: GGAAGAAGCTTCCAAACAGG Reverse: CCATCCTGCTCCTTCACATT | 54 | 1 | 895 |
| exon17 | Forward: TGCTTGTTGGTCCCTACCTC Reverse: GGTTTCCTGTGCCACGTTTA | 54 | 1 | 395 |
| exon18-19 | Forward: GGTTAGCCAAAGGGTCACAA Reverse: ACAAAAACCACGTCCTGGAG | 54 | 1 | 593 |
| exon20 | Forward: GGCTAATTTGGGCACTTTGA Reverse: CCCCTTTCTTCTGCTGTTCA | 54 | 1 | 354 |
| exon21 | Forward: GCGGAAATGCAGAGCTAACA Reverse: GGAGATGGTCAATGCCAAAG | 54 | 1 | 395 |
| exon22 | Forward: TGTCCCCACTCCCACTAATC Reverse: AAAAACACGTCCAAGTCTGG | 54 | 1 | 233 |
| exon23-24 | Forward: CTGACGGGTGTTACCATCG Reverse: AGCACTGAAGGCTCCACATT | 54 | 1 | 712 |
| exon25 | Forward: GAACAGACCGGAGGTCAGAG Reverse: CTGTGGGTCCTCCACTCTTC | 61 | 2 | 328 |

TABLE 1-continued

Primer sequences and PCR conditions.
Primer sequences and PCR conditions
for SPTBN2 sequencing

| Exon(s) | Sequence (5'-3') | Ta | Mg | size (bp) |
|---|---|---|---|---|
| exon26 | Forward: TAACATCACGGCATGGTCTG Reverse: CCCTAGCTCCTGGGAACTCT | 54 | 1 | 498 |
| exon27-28 | Forward: CTTGGAGTCCCCCGCTCT Reverse: AAGCAGAAAGCCACCAAGAA | 54 | 1 | 599 |
| exon29 | Forward: TCACATCCTGGTGCTAACTCA Reverse: CCTACTCTGGAACCCACAGG | 61 | 3 | 201 |
| exon30 | Forward: CCACTCTGACCCACCATCTT Reverse: AAGCCAGCACAGGTCAGG | 54 | 1 | 300 |
| exon31-33 | Forward: CCCTCTTACACGCAACCTTC Reverse: GACCCTTCGCCTCACAGTTA | 54 | 1 | 541 |
| exon34 | Forward: GGTTAGGGATCTCCCGTCTC Reverse: CCCTTTGCCCAGAAGATGTA | 54 | 1 | 374 |
| exon35 | Forward: AGATGGGAGCAGAACTGGAA Reverse: CTGGCCTGGTTACTCCACTC | 54 | 1 | 392 |
| exon36 | Forward: TACGCTCTCACCAGCAGCTA Reverse: CGCACACATCCAGTCTTACC | 59 | 2 | 243 |
| exon37 | Forward: CAGCTCACTTTCTGCCTCCT Reverse: AGAGAGGCTGTGGTCAGGAA | 57 | 1 | 998 |

Primer sequences and PCR conditions for
SPTBN2 mutation screening

| Mutation | Sequence (5'-3') | Ta | Mg | size (bp) |
|---|---|---|---|---|
| For E532_M544del (American mutation) | Forward: AGCGCTACCACGACATCAAG Reverse: CCCTCGACTCTTGATCACTCTT | 54 | 1 | 222 (normal) 183 (mutant) |
| For L629_R634delinsW (French mutation) | Forward: GTGGCCAAGCTAGAGCAGAG Reverse: CACCTCCCAGAGGAAACG | 61 | 2 | 105 (normal) 90 (mutant) |
| For L253P (German mutation) | Forward: CACGACGTTGTAAAACGACGAA CTGGGACTTACCAAGCT (for normal) Forward: | 55 | 1.5 | 177 (normal) 158 |

-continued

Primer sequences and PCR conditions for
SPTBN2 mutation screening

| Mutation | Sequence (5'-3') | Ta | Mg | size (bp) |
|---|---|---|---|---|
| | GAACTGGGACTTACCAAGCC (for mutant) Reverse: CCAAAGAAGCCCTGTATCA | | | (mutant) |

Primer sequences and PCR condition for RT-PCR
analysis of the American SCA5 deletion

| Purpose | Sequence (5'-3') | Ta | Mg | size (bp) |
|---|---|---|---|---|
| For first-strand synthesis | CCTCAGCTTCACCCACCTC | | | |
| PCR-primer in exon 12 | Forward: AGCGCTACCACGACATCAAG | 54 | 1 | 227 (normal) |
| PCR-primer in exon 13 | Reverse: CAGGTCCTCCACTCCTGCTA | | | 188 (mutant) |

Primer sequences and PCR conditions to generate
a β-III spectrin construct with the American
SCA5 deletion

| Purpose | Sequence (5'-3') | Ta | Mg | size (bp) |
|---|---|---|---|---|
| To generate a PCR fragment including the American SCA5 deletion* | SPΔ39.1f: GTGTCCCAGGACAACTTTGG SPΔ39-1r: ATCCAGTCCAGGTTGAGGAGGA GCCGCTCC | 54 | 1 | 260 |
| | SPΔ39-2f: CTCCTCAACCTGGACTGGATGG AAGAGATG SPΔ39-2r: CTCCAGGGTGAGCTTCAGG | 54 | 1.5 | 486 |
| To introduce a myc-tag to the N-terminal coding region | myc-f1: CTCATCTCAGAAGAGGATCTGA GCAGCACGCTGTCACCC | 55 | 1 | 303 (f1-r) |
| | myc-f2: CGCGGGTACCACCATGGAACAA AAACTCATCTCAGAAGAGGATC myc-r: GAGGAGCCTCAGCAGGTTG | 55 | 1 | 328 (f2-r) |

Ta: annealing temperature (° C.)
Mg: MgCl₂ (mM)
*After PCR with SPΔ39 primer sets 1 and 2, a third PCR was performed at 54° C. with 1.5 mM MgCl₂ by SPΔ39-1f and SPΔ39-2r primers.

RT-PCR analysis. RNA was harvested from ~100 mg of cerebellar autopsy tissue from an American SCA5 patient and a control individual using TRIzol (Invitrogen, Carlsbad, Calif.). First-strand synthesis was performed using the Invitrogen SuperScript™ First-Strand Synthesis System for RT-PCR kit (Invitrogen, Carlsbad, Calif.) and a SPTBN2 gene specific primer from exon 14. PCR primers flanking the American SCA5 deletion region were located in exons 12 and 13, respectively. The products were separated on a 2% agarose gel and visualized with ethidium bromide. The primers and conditions for RT-PCR analysis of the American SCA5 deletion are shown in Table 1.

Immunohistochemistry. The autopsy tissue from an American SCA5 family member and a control individual, without neurological disease, and brains from control and SCA1 B05 transgenic mice were embedded in paraffin, and 5µm sections were prepared. These sections were incubated in 0.3% $H_2O_2$ for 30 min to bleach endogenous peroxidase activity, then heated by a steamer in 10 mM citrate buffer at pH 6.0. Sections were blocked in 5% normal serum, derived from animals in which the secondary antibodies had been made. Slides were incubated at 4° C. overnight with β-III spectrin or EAAT4 antibodies (Santa Cruz Biotechnology, Santa Cruz, Calif.) diluted at 1:500 or 1:100, respectively. Positive staining was visualized by the avidin-biotin-peroxidase complex method (Vector, Burlingame, Calif.) with diaminobenzidine as the chromogen and counterstained with hemotoxylin.

Immunoblot analysis. Cerebellar tissue from an SCA5 American family member, human control, murine control and SCA1 B05 transgenic mice were used for Western analysis. Tissue was extracted with a Polytron homogenizer in RIPA lysis buffer (1×PBS, 1% Nonidet P-40, 0.5% sodium deoxycholate, 0.1% SDS, 100µg/ml PMSF, 50 KIU/ml aprotinin, 1 mM sodium orthovanadate). To ensure the efficiency of protein extraction, the same cerebellar tissues were re-extracted in a stronger lysis buffer containing 8M urea, 4% SDS, 0.125M Tris-HCl (pH 6.8),12mM EDTA, 3% β-mercaptoethanol, and 1× protease inhibitors (Complete, Roche, Indianapolis, Ind.). To determine if EAAT4 was decreased in amount beyond that expected due to Purkinje cell loss, the amount of protein loaded was normalized relative to the Purkinje cell specific protein calbindin. After solubilization, samples were separated by SDS-PAGE and transferred to a nitrocellulose membrane and incubated at 4° C. overnight with EAAT4 or calbindin (Sigma-Aldrich, Saint Louis, Mo.) antibodies diluted at 1:200 or 1:6,000, respectively. The immunoblot was visualized with horseradish peroxidase-conjugated secondary antibody and enhanced chemiluminescence (Amersham Biosciences, Uppsala, Sweden).

Subcellular fractionation. Subcellular fractionation analysis was performed as described elsewhere (Lee et al., Neuropharmacology 41, 680-692 (2001) with slight modifications. Briefly, cerebellar tissues (500 mg each) from American SCA5 and control autopsy brains were resuspended by Polytron homogenization in 5 ml of buffered sucrose (0.32M sucrose, 5 mM Tris (pH 7.5), 0.5 mM $CaCl_2$, 1 mM $MgCl_2$, and 1× protease inhibitors (Complete, Roche, Indianapolis, Ind.). Tissue was sheared by passage through an 18-gauge needle repeatedly, and the lysate was pelleted at 500×g for 10 min (P1 fraction). The supernatant (S1) was separated into two 0.5-ml aliquots and all aliquots were centrifuged at 10,500×g for 15 min. For one of the aliquots, the supernatant (S2) and pellet (P2) were isolated. For the other aliquot, the pellets from the 10,500×g spin (P2) were resuspended and hypotonically lysed by the addition of 50 µl of ice-cold $H_2O$ (with 1× protease inhibitors) and passage through an 18-gauge needle 10 times. This mixture was then centrifuged at 25,000×g for 20 min, generating LS1 (supernatant) and LP1 (pellet) fractions. All pelletable fractions (P1, P2, and LP1) were resuspended in a lysis buffer containing 8M urea, 4% SDS, 0.125M Tris-HCl (pH 6.8), 12 mM EDTA, 3% β-mercaptoethanol, and 1× protease inhibitors. All resulting fractions were then analyzed by SDS-PAGE and Western blotting. Antibodies against proteins examined in subcellular fractionation analysis were used at the following dilutions:

EAAT4 (1:200), GluRδ2 (1:1,000, BD Biosciences, San Jose, Calif.), and clathrin light chain (1:1,000, Synaptic Systems, Goettingen, Germany).

Cloning of EAAT4 and β-III spectrin constructs, cell culture and transfection. Standard techniques were used in the construction of the β-III spectrin control and deletion constructs and the EAAT4-GFP construct. Briefly, a full-length SPTBN2 pBluescript cDNA clone (KIAA0302, Kazusa DNA Research Institute) was re-cloned into the mammalian expression vector pcDNA3.1 (Invitrogen, Carlsbad, Calif.) and modified by PCR using overlapping primer sets (set1: SPΔ39-1f and SPΔ391r, and set 2: SPΔ39-2f and SPΔ39-2r). The American family deletion was created by generating separate PCR products (SPAΔ39 primer sets 1 and 2) followed by a third PCR reaction (primers SPΔ39-1f and SPΔ39-2r) to generate the 39bp deletion mutation (SP-Δ39) found in the American kindred. These PCR products were then subcloned using BsmB I and Age I digestion. Subsequently, a myc-tag was introduced into both the wildtype (SP-WT) and mutant constructs immediately downstream of the ATG start codon by PCR (myc-f1 and myc-r, followed by myc-f2 and myc-r primers) and then subcloned using Kpn I and Pml I digestion. Sequencing was performed to verify the integrity of the tag and the entire cDNA and coding errors were fixed using the QuikChange II XL Site-Directed Mutagenesis Kit (Stratagene, La Jolla, Calif.). The primer sequences and PCR conditions to generate the β-III spectrin constructs are shown in Table 1.

The EAAT4-GFP construct was generated using primers containing the appropriate restriction enzyme recognition sites and an overlap extension PCR-based strategy. Resulting EAAT4 PCR products were cloned into the Eukaryotic expression vector pEGFP-C2 (Clontech), and coding regions were confirmed by sequencing. HEK293 cells were transfected (0.5 μg/dish) using FuGene 6 (Roche, Indianapolis, Ind.) following standard protocols. Cells were plated directly on glass bottom culture dishes (MatTek, Ashland, Mass.) and imaged 24 hours after transfection.

TIRF microscopy and analysis. Light from an ion laser was introduced into an inverted epifluorescence microscope (IX81, Olympus) and the light was focused at the back focal plane of a TIRFM objective lens (PlanApo 60×/1.45NA, Olympus). The transfected cells on the glass coverslip were maintained at 37° C. using a temperature controller (Harvard apparatus) and pH 7.4 by 10 mM Hepes. Images were collected by an EM-charge-coupled-device camera (Olympus) operated with Metamorph 6.3 (Universal Imaging). Time laps images were acquired every 450 msec. Analysis, including tracking (the single projection of different images) and area calculations, were performed using Metamorph. Each diffraction spot was filtered twice (High pass filter >3 pixel) and (Low pass filter <30 pixel). EAAT4 lateral movement images where superimposed to a single image to measure the total area of the transporter movement, while total trafficking distance of diffraction spots was calculated using the Metamorph tracking module.

Results

Figure 2:
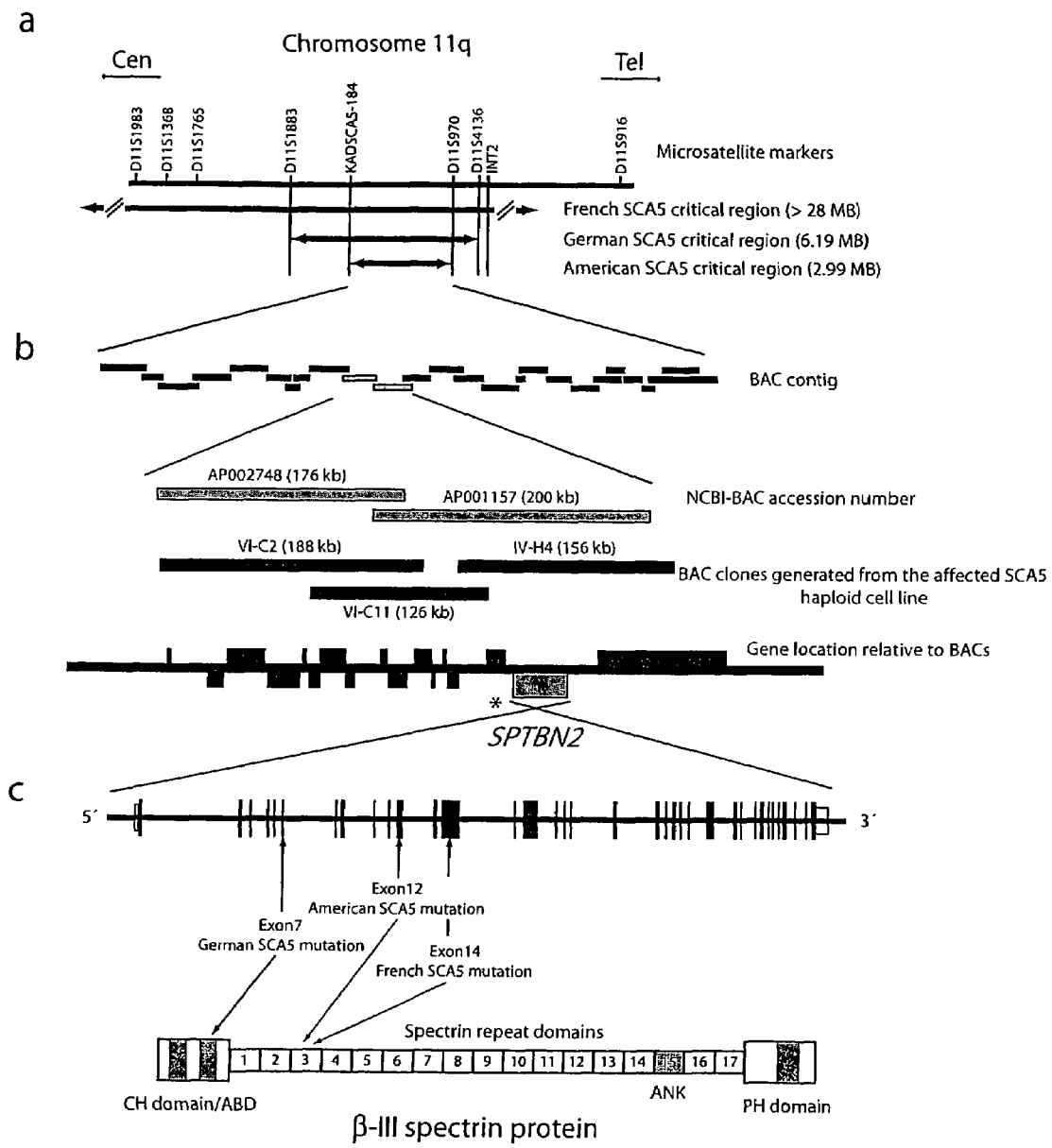
FIG. 2. Mapping and cloning of the SCA5 mutations. (a) Critical regions defined by recombination events in the three SCA5 families are indicated by black arrows. The boundaries of the French critical region are not defined because no recombination events were found among affected family members. Markers defining recombination events, along with other published markers are shown. (b) BAC map spanning the SCA5 region. A panel of 445 novel di-, tri-, tetra-, and penta-nucleotide repeat markers were used to refine the SCA5 region and search for haplotype conservation between the families. Chromosome-separated cell lines haploid for the affected or the normal chromosome 11 were generated from an affected American family member and used in this screen to directly and unambiguously define the affected haplotype. The enlarged BACs, highlighted in gray, span a 255 kb region of haplotype conservation between the American and French families, containing 11 novel polymorphic STR markers and 8 SNPs (size and NCBI accession number noted). The three BACs generated from the affected SCA5 haploid cell line are depicted in black along with their relative position and size. The approximate sizes and locations of genes present on the SCA5 specific BAC clones are illustrated by black blocks. The block shaded in gray represents the gene SPTBN2. (c) Illustration of SPTBN2 gene (top) and protein structure (bottom). The relative size and location of the 3'/5'-UTR and exons are represented by clear and solid squares, respectively. Locations of the three mutations are indicated by arrows on the gene and protein diagrams. β-III spectrin is a 2,390 amino acid protein that is highly homologous to the four other human β-spectrin proteins. Known domains in the protein are specified along with the seventeen spectrin repeats. The calponin-homology (CH)/actin binding domain (ABD), ankyrin binding domain (ANK), and pleckstrin-homology domain (PH) are shaded in gray. The functional unit of spectrin is typically a non-covalently-joined tetrameric complex consisting of two alpha and two beta spectrin subunits. An asterisk (*) indicates that the direction of SPTBN2 transcription relative to chromosome 11q is reversed.

The American family has two major branches that descend from the paternal grandparents of President Abraham Lincoln (FIG. 1). SCA5, referred to as "Lincoln Disease" by family members, is found among the descendents of President Lincoln's paternal uncle Josiah and aunt Mary, indicating that one of President Lincoln's paternal grandparents carried the SCA5 mutation. These two branches of the family are shown in FIG. 1. Clinical evaluations and DNA collection were performed on 299 family members, including 90 affecteds (onset 4-68 yrs). Because the disease in some individuals is relatively mild and the clinical status of the President, his father Thomas, and Thomas's descendants (all deceased since 1960) are unknown, the prior probability that the President inherited the SCA5 mutation is 25%. Recombinations were used to refine the critical region to 2.99 megabases containing ~100 genes (FIG. 2a). Haplotype comparisons between families identified a 255 kb region of possible conservation between the American and French families. Although this haplotype was also found in 3/84 (3.5%) control chromosomes, this region was prioritized because of the possibility that this conservation resulted from a common ancestral mutation. DNA from an affected chromosome-separated cell line known to contain the American SCA5 mutation, was used to construct a BAC library and clone contig of the region and shotgun sequencing of patient-derived BAC clones (VI-C2, VI-C11, and IV-H4) spanning the area of haplotype conservation (FIG. 2b) was performed.

Figure 3D:
FIG. 3. The three SCA5 mutations and μ-III spectrin expression. PCR analysis and the corresponding genotype for the three SCA5 families are illustrated for each mutation. Sequence electropherograms and the corresponding amino acid sequence are also shown. (a) American SCA5 mutation. The PCR analysis generated a 222 bp normal allele and a 183 bp deleted allele (nucleotides 13780-13884 and 15563-15577 of SEQ ID NO:1 are depicted, as are the amino acids 517-556 of SEQ ID NO:2). The sequence of SCA5 BAC DNA is shown with the deletion mutation relative to control (nucleotides AACCTGGACTGG, which correspond to nucleotides 13819-13826 and 13899-13869, or nucleotides 13819-13822 and 13862-13869, depending on the location of the deletion) and the amino acids Asn Leu Asp Trp (amino acids 530-531 and 545-546 of SEQ ID NO:2). The two arrows indicate the two possible deletion sites, and the corresponding 39-base deletions including one of the two flanking TGGA tetranucleotides is underlined. The two TGGA tetranucleotides flanking the American deletion are reminiscent of the deletions caused by slipped-mispairing (Krawczak et al., Hum Genet 86, 425-441 (1991). (b) French SCA5 mutation. The [γ-$^{33}$P] ATP-labeled PCR generated a 105 bp normal allele and a 90 bp deleted allele (nucleotides 15973-16092 of SEQ ID NO:1 are depicted, as are the amino acids 617-656 of SEQ ID NO:2). Sequence of the heterozygous PCR products are shown: nucleotides 16004-16016 (normal allele) and nucleotides 16004-16009 and 16025-16031 (mutant allele) of SEQ ID NO:1. Sequence of the deletion specific PCR product is shown: nucleotides 16003-16009 and 16025-16032 of SEQ ID NO:1 and amino acids Cys Glu Trp Ala Arg (SEQ ID NO:78). Arrows indicate the site of the mutation and the 15-base deletion is underlined. (c) German SCA5 mutation. The T to C base change is depicted (SEQ ID NO:79), as is the conversion of leucine to proline (SEQ ID NO:80). The allele-specific PCR produced a 177 bp normal allele and a 158 bp mutation allele. Amino acid sequence comparisons, of a region containing the German SCA5 mutation (L253P), of five human beta spectrins (SEQ ID NOs:81-85) and beta spectrins from other species (SEQ ID NOs:86-92) are shown. The leucine residue (marked with arrow) which is mutated in the German family is conserved in all five of human beta spectrin proteins and evolutionarily conserved in multiple species. Amino acid alignments were performed with Clustal W (available online through the World Wide Web at, for instance, the Kyoto University Bioinformatics Center). While previously reported polymorphisms were also found in each family, these mutations were the only unreported differences, and the only changes that would alter the corresponding protein. (d) RT-PCR analysis of American SCA5 and control cerebellar tissues. The normal SPTBN2 amplified product is 227 bp and the product containing the deletion is 188 bp. There was no amplification in the RT- or no RNA control lanes. SCA5-cbl RT+, cerebellum from SCA5autopsy with reverse transcriptase; SCA5-cbl RT−, cerebellum from SCA5 autopsy without reverse transcriptase (control and should not see product); Cont-cbl RT+, cerebellum from Normal autopsy with reverse transcriptase; CONT-cbl RT−, Cerebellum from normal autopsy without reverse transcriptase (control and should not see product). (e) Immunohistochemistry of control and American SCA5 cerebellar tissues. Sections were stained with an antibody raised against the N-terminal portion of the β-III spectrin (Santa Cruz Biotechnology, Santa Cruz, Calif.), and visualized at 200× magnification. Enlarged images of the Purkinje cells are also shown (630×). Purkinje cell loss, dendritic atrophy and significant thinning of the molecular layer are seen in SCA5 compared to control.

A 39-base pair deletion was found in exon 12 of the β-III spectrin gene (SPTBN2) which causes an in-frame 13 amino-acid deletion (p.E532_M544del) within the third of 17 spectrin repeats (FIG. 2c,3a, Table 2). The mutation, which is detectable by PCR (FIG. 3a), was found in all 90 affected individuals (age of exam 7-80 yrs, mean 45 yrs) and 35 presymptomatic carriers (age of exam 13-67 yrs, mean 34 yrs).

TABLE 2

Summary of DNA sequence variations of exons found in 3 BAC regions.

| Genes | Status | No of exons | No of seq. variations | Exon# | NCBI SNP ID |
|---|---|---|---|---|---|
| MRPL11 | Reviewed | 5 | 0 | — | — |
| PELI3 | Provisional | 8 | 2 | exon 6 | rs2277302 |
|  |  |  |  | exon 8 | rs3179961 |
| DPP3 | Reviewed | 18 | 3 | exon 4 | rs11550299 |
|  |  |  |  | exon 17 | rs1671063 |
|  |  |  |  | exon 17 | rs2305535 |
| BBS1 | Reviewed | 17 | 4 | exon 4 | rs2298806 |
|  |  |  |  | exon 14 | rs3816492 |
|  |  |  |  | exon 17 | rs8432 |
|  |  |  |  | exon 17 | rs3741360 |
| AK126268 | Predicted | 1 | 2 | exon 1 | rs7116921 |
|  |  |  |  | exon 1 | rs7116940 |
| ZDHHC24 | Provisional | 3 | 1 | exon 1 | rs2305534 |
| ACTN3 | Reviewed | 21 | 7 | exon 14 | rs1671064 |
|  |  |  |  | exon 15 | rs2305537 |
|  |  |  |  | exon 15 | rs1815739 |
|  |  |  |  | exon 16 | rs618838 |
|  |  |  |  | exon 16 | rs7924602 |
|  |  |  |  | exon 18 | unregistered[a] |
|  |  |  |  | exon 19 | rs540874 |
| CTSF | Reviewed | 13 | 4 | exon 2 | rs2075791 |
|  |  |  |  | exon 6 | rs545009 |
|  |  |  |  | exon 13 | rs572846 |
|  |  |  |  | exon 13 | rs4576 |
| FLJ10786 | Predicted | 1 | 0 | — | — |
| CCS | Reviewed | 8 | 1 | exon 8 | rs1127145 |
| RBM14[b] | Validated | 3 | 0 | — | — |
| MGC15912[b] | Predicted | 1 | 0 | — | — |
| LOC440048[b] | Model | 3 | 1 | exon 3 | rs670900 |
| RBM4[b] | Provisional | 5 | 0 | — | — |
| RBM30 | Predicted | 4 | 0 | — | — |
| SPTBN2 | Provisional | 37 | 1[c] | exon 14 | rs4930388 |
| FLJ22531 | Predicted | 6[d] | 0 | — | — |

[a]synonymous SNP (AGG → AGA: Arg774)
[b]found sequence gap between contigs
[c]except for pathogenic SCA5 mutations
[d]exons7-17 not included in IV-H4 BAC Although the American and French families share a common haplotype, the 39-bp American deletion was not found in the French family. Similar to the American family, the French family has a short in-frame deletion in the same spectrin repeat consisting of a 15-base pair deletion in exon 14 (c.1886_-1900del; p.L629_R634delinsW) (FIG. 2c, 3b). With the exception of the insertion of a tryptophan, this deletion does not disrupt the remainder of the open-reading frame (FIG. 3b). The French mutation was found in all six available affected individuals and one apparently presymptomatic carrier (age 24).

Figure 3E:
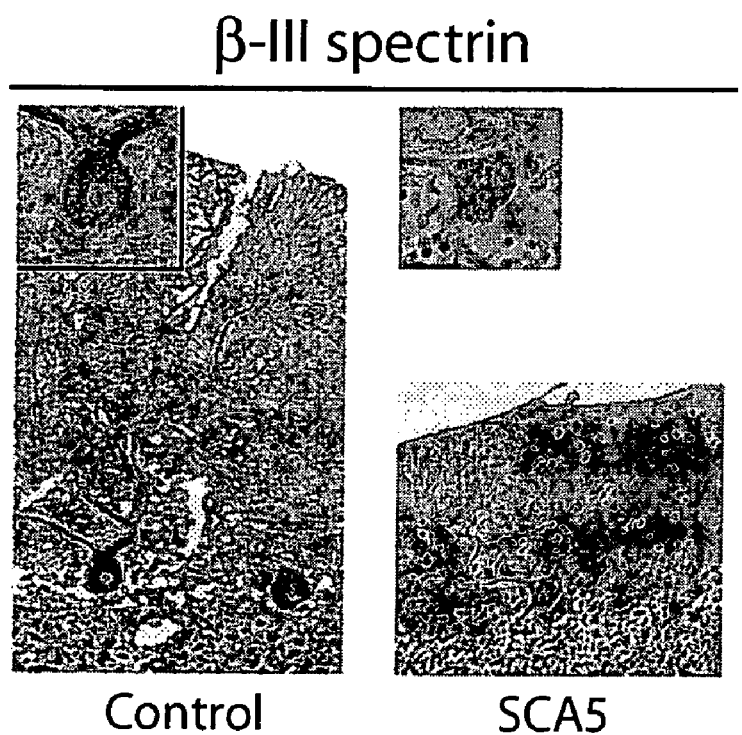

In the German family a T to C transition mutation (c.758T>C) in exon 7 that causes a leucine to proline change (p.L253P) (FIG. 2c, 3c) was found in the calponin-homology domain containing the actin/ARP1 binding site. This region is highly conserved with the leucine 253 residue found in all five human β-spectrin proteins as well as chimp, mouse, rat, dog and fly (FIG. 3c). The German mutation co-segregated with the disease in 12 available affected individuals. None of the three SCA5 mutations were found on 1,000 control chromosomes.

β-III spectrin, a 2,390 amino-acid protein highly expressed in Purkinje cells (Ohara et al., Brain Res Mol Brain Res 57, 181-192 (1998)), (Stankewich et al., Proc. Natl. Acad. Sci. USA 95, 14158-14163 (1998)), was originally described as a protein associated with Golgi and vesicle membranes (Stankewich et al., Proc. Natl. Acad. Sci. USA 95, 14158-14163 (1998)) and has been reported to bind to the dynactin subunit ARP1, suggesting a possible role in transport (Holleran et al., J. Biol Chem 276, 36598-36605 (2001)). Another function of β-spectrin is the stabilization of membrane proteins (Parkinson et al., Nat Genet 29, 61-65 (2001)); notably β-III spectrin stabilizes the Purkinje cell specific glutamate transporter EAAT4 (Jackson et al., Nature 410, 89-93 (2001)). RT-PCR analysis shows both normal and deleted β-III spectrin transcripts are expressed in affected cerebellar autopsy tissue (FIG. 3d) with immunohistochemistry showing staining of Purkinje cell bodies, dendrites and axons in both SCA5 and control cerebella, with marked Purkinje cell loss in SCA5 (FIG. 3e).

Figure 4:
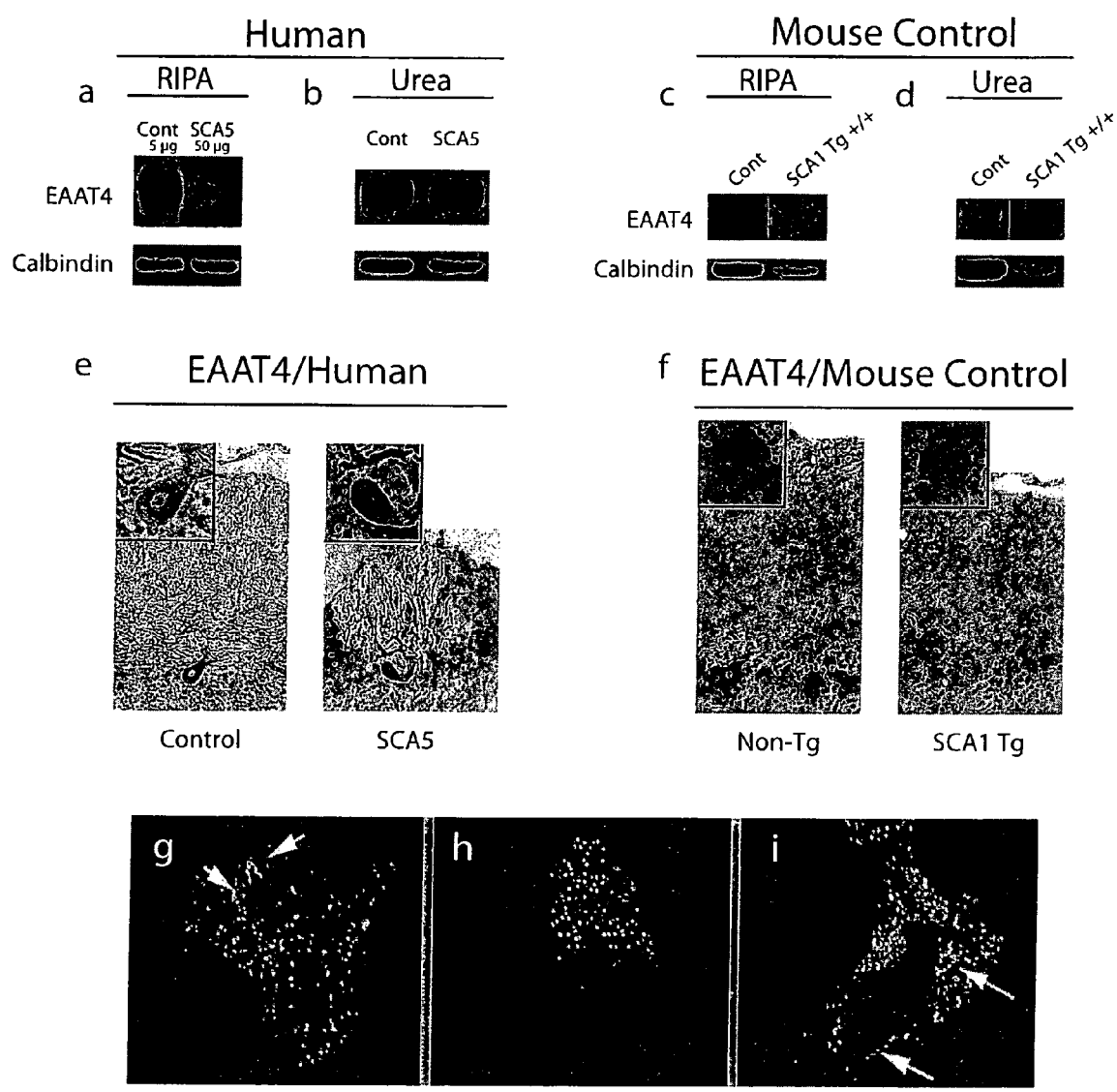
FIG. 4. Western, immunohistochemistry and TIRF microscopy: effects of mutant β-III spectrin on EAAT4. EAAT4 immunoblot comparisons of lysates extracted with RIPA buffer (a, c) or 8M urea and 4% SDS (b, d). EAAT4 and calbindin are both highly expressed in Purkinje cells, with little or no expression in other cells within the cerebellar cortex. When possible, samples were normalized for Purkinje cell loss with calbindin. Markedly less EAAT4 relative to the calbindin control was extracted from human SCA5 cerebella compared to control tissue in the RIPA extracts (a) but similar levels of EAAT4 were found in the harsher 8M urea, 4% SDS buffer (b). As a control, we examined murine extracts from homozygous 12 week old SCA1 B05 mice but did not observe similar increases in EAAT4 in the urea vs. the RIPA extracts (c, d). EAAT4 immunohistochemistry of American SCA5 (e), murine SCA1 (f) and corresponding human and murine controls. Sections were stained with EAAT4 antibody, and visualized at 200× magnification. Enlarged images of the Purkinje cells are also depicted (630×). Darker EAAT4 staining was observed in the SCA5 Purkinje cell bodies (representative sample) but not in Purkinje cells from SCA1 transgenic mice or controls. (g-i) EAAT4 fast lateral trafficking is modulated by β-III spectrin interaction. (g) A superimposed image shows the total lateral movement of EAAT4 when expressed with an empty vector in HEK293 cells (arrows). (h) EAAT4 was co-transfected with wildtype β-III spectrin and no lateral fast movement was seen. (i) EAAT4 was co-transfected with mutant β-III spectrin containing the 39 bp SCA5 deletion and fast movement was seen again (arrows).

Western analysis was performed on cerebellar autopsy tissue to investigate whether the 39-bp spectrin deletion mutation affects EAAT4. Protein levels of EAAT4 in SCA5 cerebellum extracted by Radio-Immunoprecipitation Assay (RIPA) buffer were dramatically reduced relative to calbindin, a Purkinje cell specific control (FIG. 4a). Surprisingly, when using a harsher extraction buffer (8M urea and 4% SDS), approximately equal ratios of EAAT4/calbindin were seen in SCA5 and control (FIG. 4b) suggesting EAAT4 solubility or distribution is affected by mutant β-III spectrin.

Decreased EAAT4 transcript levels have been previously reported in SCA1 transgenic mice prior to Purkinje cell loss (Lin et al., Nat Neurosci 3, 157-163 (2000)), suggesting that loss or dysfunction of EAAT4 may be a common downstream molecular change. To determine if the extractability differences of EAAT4 in SCA5 is a non-specific change caused by Purkinje cell degeneration, EAAT4 extractability was examined in SCA1 transgenic mice with significant Purkinje cell loss (FIG. 4c,4d). Consistent with previous reports reduced levels were found of EAAT4 by Western and in contrast to SCA5, EAAT4 levels were similarly reduced in RIPA and Urea extracts. EAAT4 immunostaining of remaining Purkinje cells in SCA5 showed a consistent thinning of the dendritic arbor and darker staining of the cell body (FIG. 4e), while SCA1 transgenic animals showed uniform but lighter staining (FIG. 4f). These results indicate that the redistribution of EAAT4 in SCA5 is not caused by Purkinje cell degeneration and that EAAT4 is likely altered by different mechanisms in SCA1 and SCA5.

Figure 5:
FIG. 5. Subcellular distribution of EAAT4 and GluRδ2. Subcellular fractionation of cerebellar homogenates from human SCA5 and control autopsy tissue was analyzed by Western blots with EAAT4 and GluRδ2, and as a control, clathrin light chain antibodies. P1 nuclear pellet; S1 postnuclear supernatant; P2 crude synaptosomal fraction; S2 supernatant of the crude synaptosomal fraction; LP1 pellet obtained after lysis of synaptosomes.

To further examine EAAT4 and to determine if mutant spectrin also causes changes in other membrane bound Purkinje cell proteins, subcellular fractionations of cerebellar tissue and subsequent Western analyses were performed (FIG. 5). Total protein loaded in the P1 and S1 fractions was determined by BCA protein assays, with the following amounts of protein in the respective lanes: P1 control (40.5 µg), S1 control (5.5 µg), P1 SCA5 (71.4 µg), S1 SCA5 (3.9 µg). Protein loading was also estimated by normalization of the Western blot membranes to clathrin light chain, a broadly expressed control protein known to cycle on and off plasma and vesicle membranes and to be abundant in membrane rich pelletable fractions. As expected, considerable enrichment of clathrin was observed in the predicted nuclear (P1), crude synaptosomal (P2), and enriched synaptosomal (LP1) fractions. More protein was loaded in SCA5 vs. control in the P1 (71.4 vs 40.5 µg), P2 and LP1 fractions (see clathrin loading control) with slightly less protein in the SCA5 S1 (3.9 vs 5.5 µg) fraction compared to control. Subcellular fractionations of EAAT4 and GluRδ2 from SCA5 cerebellar extracts differ from control cerebellum. For example, because more protein was loaded in SCA5 P2 and LP1 fractions vs. control P2 and LP1 fractions (determined by clathrin), if EAAT4 in the SCA5 and control homogenates were fractionating in the same way, more EAAT4 would be expected in the overloaded SCA5 P2 and LP1 fractions. However, dramatically less EAAT4 is found in these SCA5 synaptosomal rich fractions (P2, LP1). Similar redistribution of the GluRδ2 are found with markedly less than predicted amounts of GluRδ2 in the SCA5 P2 and LP1 fractions compared to control P2 and LP1. In contrast to control, the synaptic membrane proteins EAAT4 and GluRδ2 were not enriched in the synaptosomal fractions in SCA5 tissue, suggesting that mutant β-III spectrin affects the cellular localization of these proteins.

To further characterize the physiological effects of mutant β-III spectrin on EAAT4 a series of controlled cell culture experiments were performed. HEK293 cells were transfected with eGFP-EAAT4 and total internal reflection fluorescence (TIRF) microscopy was used to follow the lateral movement of the glutamate transporter on the cell's membrane. The glutamate transporters normally alternated within seconds between two main states: periods of rapid movement on the cell's membrane and restricted motion within a sub-micrometer area (FIGS. 4g-i). When EAAT4 was expressed along with an empty control vector, almost 40% of the EAAT4 diffraction spots were actively moving at or near the plasma membrane (~4 microns), while the slow moving diffraction spots were typically restricted to movements in a fixed small area (less than 1 micron) (FIG. 4g, Table 3). To further investigate the physiological relevance of the interaction between EAAT4 and wildtype β-III spectrin, EAAT4 was co-transfected with β-III spectrin and followed the trafficking of EAAT4. Consistent with previous biochemical studies (Jackson et al., Nature 410, 89-93 (2001)), co-expression of wildtype β-III spectrin stabilized EAAT4 with only 5% of diffraction spots moving at or near the membrane, and none showing large lateral movements (>4 microns) (FIG. 4h, Table 1). However, in the presence of mutant β-III spectrin with the 39 bp deletion, the stabilization of EAAT4 was lost, and the transporter was highly motile with many lateral movements over 4 microns observed (FIG. 4i, Table 3). To confirm the specific interaction between EAAT4 and β-III spectrin, β-III spectrin was co-transfected with EAAT3, another glutamate transporter also expressed in Purkinje cells. Neither wildtype (Table 3) nor mutant β-III spectrin had any substantial effect on EAAT3 stability. The lack of an effect on EAAT3 does not exclude the possibility that mutant β-III spectrin affects other membrane proteins. These studies however, provide evidence that mutant β-III spectrin can disrupt the stability of EAAT4 and because altered expression of EAAT4 on the membrane is known to increase Purkinje cells to injury/degeneration it therefore may contribute to Purkinje cell degeneration in SCA5 (Welsh et al., Adv Neurol 89, 331-359 (2002)). Table 3. Mutant β-III spectrin alters lateral trafficking of glutamate transporters. TIRF microscopy of HEK293 cells was performed and digital movies of the imaged cells were evaluated using Metamorph. Each diffraction spot was analyzed separately. For each condition 3-6 different experiments were recorded from different dishes and different days. The results are mean±SD.

| construct | Total diffraction spots analyzed | % of diffraction spots not moving |
|---|---|---|
| eGFP-EAAT4 + empty vector | 685 | 62.0 ± 8.7 |
| eGFP-EAAT4 + wildtype β-III spectrin | 122 | 94.2 ± 9.7 |
| eGFP-EAAT4 + mutant β-III spectrin | 375 | 67.5 ± 4.4 |
| eGFP-EAAT3 + empty vector | 547 | 61.0 ± 11.2 |
| eGFP-EAAT3 + wildtype β-III spectrin | 337 | 58.7 ± 5.4 |

We report a novel mutational mechanism for spinocerebellar ataxia with the identification of three separate mutations in the β-III spectrin gene (SPTBN2) responsible for SCA5. The American and French families have similar but separate in-frame deletions within the third spectrin repeat, and are likely to disrupt the highly ordered triple-alpha-helical structure of the repeat changing the overall shape of the tetrameric alpha-beta-spectrin complex. Although it is possible that some feature of the shared haplotype between the American and French families led to similar microdeletions, it appears more likely that the shared haplotypes are coincidence as this haplotype is found on 3.5% of control chromosomes. The German family has a missense mutation in the calponin-homology domain, which may disrupt the ability of spectrin to bind to the actin cytoskeleton and similarly affect the stabilization of membrane proteins or cause alterations in transport by disrupting binding to ARP1 and the dynein motor complex (Holleran et al., J. Biol. Chem 276, 36598-36605)).

The cell fractionation studies suggest that mutant β-III spectrin (39 bp deletion) affects localization of the synaptosomal proteins EAAT4 and GluRδ2. Interestingly, EAAT4 is also affected in SCA1 transgenic mice with the downregulation of transcript levels (Lin et al., Nat Neurosci 3, 157-163 (2000)) and (Serra et al., Hum Mol Genet 13, 2535-2543 (2004)). Further evidence for the possible role of EAAT4 in ataxia comes from intracisternal antisense knockdown experiments in rats which resulted in progressive ataxia (Raiteri et al., Prog Neurobiol 68, 287-309 (2002)). In addition, mutations in GluRδ2 cause ataxia in both lurcher and hotfoot mice (Lalouette et al., Genomics 50, 9-13 (1998)) and (Zuo et al., Nature 388, 769-773 (1997)). Loss of EAAT4 and GluRδ2 at the plasma membrane in SCA5 could lead to glutamate signaling abnormalities, which over time could cause Purkinje cell death in SCA5.

The reported interaction of spectrin with the dynactin-dynein motor complex suggests that SCA5 mutations could affect protein trafficking as in other neurodegenerative diseases. These disorders include a dominantly inherited motor neuron disease caused by mutations in p150$^{Glued}$, a subunit of dynactin (DCTN1) (Puls et al., Nat Genet 33, 455-456 (2003)) and a motor neuronopathy caused by missense mutations in the mouse dynein heavy chain gene (Dnchc1)(Hafezparast et al., Science 300, 808-812 (2003)). In Huntington disease, alterations of the huntingtin/HAP1/p150$^{Glued}$ complex induce transport deficits and loss of neurotrophic support contributing to neuronal toxicity (Gauthier et al., Cell 118, 127-138 (2004)), and axonal transport defects are found in Alzheimer's patients and murine models (Stokin et al., Science 307, 1282-1288)).

Identifying additional mutations in SPTBN2 that cause ataxia in families with unknown mutations will provide further insight into the functions of β-III spectrin and the molecular mechanisms of neurodegenerative diseases. Specifically, it will be of interest to determine if mutations in SPTBN2 also cause SCA20, a clinically distinct form of ataxia whose critical region includes SPTBN2 (Knight et al., Brain 127, 1172-1181 (2004)). It will also be important to determine if mutations in SPTBN5 or SPTBN1, which map to the SCA11 and SCA25 critical regions respectively, also cause ataxia (Worth et al., Am J Hum Genet 65, 420-426 (1999)) and Stevanin et al., Ann Neurol 55, 97-104 (2004)). Consistent with the possibility that the β-spectrins may play additional roles in disease, dominantly inherited mutations in a beta spectrin homologue cause an uncoordinated phenotype (unc-70) in C. elegans (Park et al., Genetics 113, 821-852 (1986)) and recessive mutations in the mouse spectrin beta 4 gene (Spnb4), an orthologue of human beta-IV spectrin (SPTBN4), cause a progressive ataxia with hind limb paralysis, deafness and tremor in quivering mice (qv) (Parkinson et al., Nat Genet 29, 61-65 (2001)).

The current estimate of 28 dominant ataxia loci provides an opportunity to use human genetics to define the fundamental causes and common molecular pathways underlying this group of neurodegenerative diseases (Schols et al., Lancet Neurol 3, 291-304 (2004)). Interestingly, down-regulation of both β-III spectrin and EAAT4 transcripts found by microarray analysis in two murine ataxia models, SCA1 transgenic and staggerer mice (Gold et al., Neuron 40, 1119-1131 (2003)) suggests the convergence pathogenic mechanisms triggered by distinct mutations. The identification of SCA5 mutations in a gene encoding a well known cytoskeletal protein will allow testing of specific hypotheses of disease pathogenesis involving destabilization of membrane proteins, glutamate dysregulation and vesicle trafficking deficits which will provide insight into the downstream molecular mechanisms common to SCA5 and other neurodegenerative diseases.

The history of ataxia in the Lincoln family raises the question of whether President Abraham Lincoln carried the SCA5 mutation. Historical descriptions suggest that the President had an uneven gait—an early sign of ataxia. On Mar. 27, 1861, William Russell a reporter for the London Times wrote of Lincoln "Soon afterwards there entered, with a shambling, loose, irregular, almost unsteady gait, a tall, lank, lean man . . . " The identification of the SCA5 mutation makes it possible to unequivocally determine if President Lincoln carried the mutation using preserved artifacts containing his DNA. In 1991, the identification of a Marfan's gene sparked debate concerning the testing of President Lincoln's DNA to determine whether his tall stature could have resulted from that disease (McKusick., Nature 352, 279-281 (1991)). Unlike for Marfan's syndrome, the Lincoln family history indicates President Lincoln was at risk of developing SCA5. Determining President Lincoln's status relative to SCA5 would be of historical interest, and would increase public awareness of ataxia and neurodegenerative disease.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method of determining whether a human subject is at risk for spinocerebellar ataxia type 5 (SCA5), the method comprising:
   providing a nucleic acid sample obtained from the human subject; and
   analyzing the nucleic acid sample for a deletion of nucleotides 13823-13861 or 13827-13865 of SEQ ID NO:1;
   wherein deletion of nucleotides 13823-13861 or 13827-13865 of SEQ ID NO:1 is indicative of the human subject being at risk for SCA5.

2. The method of claim 1 wherein the nucleic acid sample comprises an SCA5 polynucleotide.

3. The method of claim 2 wherein the analyzing comprises hybridization.

4. The method of claim 2 wherein the SCA5 polynucleotide is a genomic SCA5 polynucleotide.

5. The method of claim 2 wherein the SCA5 polynucleotide is a processed SCA5 polynucleotide.

6. The method of claim 2 wherein the analyzing comprises amplification of the SCA5 polynucleotide.

7. The method of claim 2 wherein the analyzing comprises sequencing a portion of the SCA5 polynucleotide.

8. The method of claim 6 wherein the amplification comprises primers AGAGGCACTGTCCCTTGGT (SEQ ID NO:19) and GCTGGTTCACACTCCACAGA (SEQ ID NO:20).

9. The method of claim 2 further comprising determining whether the SCA5 polynucleotide comprises a mutation in exon 7, in exon 14, or a combination thereof;
   wherein the mutation in exon 7 comprises a change of a T to a C at nucleotide 7755 of SEQ ID NO:1; and
   wherein the mutation in exon 14 comprises a deletion of nucleotides 16010-16024 of SEQ ID NO:1.

* * * * *